(12) United States Patent
Litvack et al.

(10) Patent No.: US 9,161,778 B2
(45) Date of Patent: Oct. 20, 2015

(54) SYSTEM AND METHOD FOR TRANSAPICAL ACCESS AND CLOSURE

(71) Applicant: Entourage Medical Technologies, Inc., Menlo Park, CA (US)

(72) Inventors: Frank Litvack, Los Angeles, CA (US); John F. Shanley, Emerald Hills, CA (US); Alan E. Shluzas, San Carlos, CA (US); Stephen H. Diaz, Palo Alto, CA (US); Gary Steese-Bradley, San Jose, CA (US)

(73) Assignee: ENTOURAGE MEDICAL TECHNOLOGIES, INC., Menlo Park, CA (US)

( * ) Notice: Subject to any disclaimer, the term of this patent is extended or adjusted under 35 U.S.C. 154(b) by 172 days.

(21) Appl. No.: 13/725,897

(22) Filed: Dec. 21, 2012

(65) Prior Publication Data

US 2014/0100604 A1    Apr. 10, 2014

Related U.S. Application Data

(63) Continuation of application No. 13/640,041, filed as application No. PCT/US2011/040085 on Jun. 10, 2011, now Pat. No. 9,044,267.

(60) Provisional application No. 61/361,365, filed on Jul. 2, 2010, provisional application No. 61/354,177, filed on Jun. 11, 2010.

(51) Int. Cl.
*A61B 1/00*    (2006.01)
*A61B 17/34*    (2006.01)
(Continued)

(52) U.S. Cl.
CPC ......... *A61B 17/3468* (2013.01); *A61B 17/0057* (2013.01); *A61B 17/0401* (2013.01);
(Continued)

(58) Field of Classification Search
CPC ........... A61B 17/0057; A61B 17/0469; A61B 2017/00247
USPC ................................... 606/151, 213; 600/184
See application file for complete search history.

(56) References Cited

U.S. PATENT DOCUMENTS

| 67,545 A | 8/1867 | Hodgins |
|---|---|---|
| 919,138 A | 4/1909 | Drake et al. |

(Continued)

FOREIGN PATENT DOCUMENTS

| CN | 1997318 A | 7/2007 |
|---|---|---|
| WO | 00/60995 | 10/2000 |

(Continued)

OTHER PUBLICATIONS

International Search Report mailed Sep. 29, 2011, in related International Application No. PCT/US2011/040085, filed Jun. 10, 2011., (3 pages).

(Continued)

*Primary Examiner* — Victor Nguyen
(74) *Attorney, Agent, or Firm* — David C. Lundmark

(57) ABSTRACT

Embodiments are described for creating and closing tissue access ports, such as transapical access ports, which involve placement of an introducer across the subject tissue structure, and deployment of a controllable port closure device assembly configured to remain in place with a ratcheting mechanism, and to hold the tissue surrounding the previous access port location closed against a sealing disc with proximal and distal strut assemblies, after the introducer has been removed.

15 Claims, 99 Drawing Sheets

(51) Int. Cl.
*A61B 17/00* (2006.01)
*A61B 17/04* (2006.01)
*A61B 17/06* (2006.01)
*A61B 17/22* (2006.01)
*A61B 17/30* (2006.01)
*A61B 19/00* (2006.01)

(52) U.S. Cl.
CPC ... *A61B17/0469* (2013.01); *A61B 2017/00243* (2013.01); *A61B 2017/00247* (2013.01); *A61B 2017/00579* (2013.01); *A61B 2017/00592* (2013.01); *A61B 2017/00601* (2013.01); *A61B 2017/00606* (2013.01); *A61B 2017/00619* (2013.01); *A61B 2017/00623* (2013.01); *A61B 2017/00637* (2013.01); *A61B 2017/00654* (2013.01); *A61B 2017/0414* (2013.01); *A61B 2017/0427* (2013.01); *A61B 2017/0464* (2013.01); *A61B 2017/0472* (2013.01); *A61B 2017/0496* (2013.01); *A61B 2017/06009* (2013.01); *A61B 2017/06023* (2013.01); *A61B 2017/06042* (2013.01); *A61B 2017/06076* (2013.01); *A61B 2017/06176* (2013.01); *A61B 2017/22067* (2013.01); *A61B 2017/22069* (2013.01); *A61B 2017/306* (2013.01); *A61B 2017/3425* (2013.01); *A61B 2017/3445* (2013.01); *A61B 2017/3484* (2013.01); *A61B 2017/3488* (2013.01); *A61B 2019/5206* (2013.01); *A61B 2019/5234* (2013.01)

(56) References Cited

U.S. PATENT DOCUMENTS

| | | |
|---|---|---|
| 1,538,271 A | 5/1926 | Biro |
| 4,204,541 A | 5/1980 | Kapitanov |
| 4,641,652 A | 2/1987 | Hutterer et al. |
| 5,269,809 A | 12/1993 | Hayhurst et al. |
| 5,356,424 A | 10/1994 | Buzerak et al. |
| 5,665,109 A | 9/1997 | Yoon |
| 5,709,692 A | 1/1998 | Mollenauer et al. |
| 5,709,694 A | 1/1998 | Greenberg et al. |
| 5,782,844 A | 7/1998 | Yoon et al. |
| 5,810,851 A | 9/1998 | Yoon |
| 5,820,631 A | 10/1998 | Nobles |
| 5,947,983 A | 9/1999 | Solar et al. |
| 6,015,416 A | 1/2000 | Stefanchik et al. |
| 6,626,917 B1 | 9/2003 | Craig |
| 6,663,633 B1 | 12/2003 | Pierson, III |
| 7,104,949 B2 | 9/2006 | Anderson et al. |
| 7,125,411 B2 | 10/2006 | Guanche |
| 7,637,918 B2 | 12/2009 | Dant |
| 7,695,432 B2 | 4/2010 | Scheyer |
| 7,749,237 B2 | 7/2010 | Chan |
| 7,776,059 B2 | 8/2010 | Craig |
| 7,871,367 B2 | 1/2011 | Anderson et al. |
| 8,216,230 B2 | 7/2012 | Hauck et al. |
| 8,500,757 B2 | 8/2013 | Miraki et al. |
| 8,556,963 B2 | 10/2013 | Tremulis et al. |
| 2003/0055313 A1 | 3/2003 | Anderson et al. |
| 2003/0204195 A1 | 10/2003 | Keane et al. |
| 2004/0030382 A1 | 2/2004 | St. Goar et al. |
| 2004/0092966 A1 | 5/2004 | Nobles et al. |
| 2004/0133220 A1 | 7/2004 | Lashinski et al. |
| 2004/0176802 A1 | 9/2004 | Skiba et al. |
| 2004/0220596 A1 | 11/2004 | Frazier et al. |
| 2004/0260344 A1 | 12/2004 | Lyons et al. |
| 2005/0021057 A1 | 1/2005 | St. Goar et al. |
| 2005/0187568 A1 | 8/2005 | Klenk et al. |
| 2005/0267524 A1 | 12/2005 | Chanduszko |
| 2006/0009800 A1 | 1/2006 | Christianson et al. |
| 2006/0106415 A1 | 5/2006 | Gabbay |
| 2006/0200199 A1 | 9/2006 | Bonutti et al. |
| 2006/0282088 A1 | 12/2006 | Ryan |
| 2006/0287661 A1 | 12/2006 | Bolduc et al. |
| 2007/0112422 A1 | 5/2007 | Dehdashtian |
| 2007/0118151 A1 | 5/2007 | Davidson |
| 2007/0198057 A1 | 8/2007 | Gelbart et al. |
| 2007/0276437 A1 | 11/2007 | Call et al. |
| 2008/0086168 A1 | 4/2008 | Cahill |
| 2009/0012545 A1 | 1/2009 | Williamson, IV et al. |
| 2009/0093809 A1 | 4/2009 | Anderson et al. |
| 2009/0209909 A1 | 8/2009 | Tanaka et al. |
| 2009/0240264 A1 | 9/2009 | Tuval et al. |
| 2009/0275960 A1 | 11/2009 | Provenza et al. |
| 2010/0087854 A1 | 4/2010 | Stopek et al. |
| 2010/0305609 A1 | 12/2010 | Cartledge |
| 2011/0028995 A1 | 2/2011 | Miraki et al. |
| 2012/0059395 A1 | 3/2012 | Kehdy et al. |
| 2012/0116418 A1 | 5/2012 | Belson et al. |
| 2012/0136200 A1 | 5/2012 | Miraki |
| 2012/0143226 A1 | 6/2012 | Belson et al. |
| 2012/0150223 A1* | 6/2012 | Manos et al. .......... 606/232 |

FOREIGN PATENT DOCUMENTS

| | | |
|---|---|---|
| WO | 02/078571 | 10/2002 |
| WO | 2005/102181 | 11/2005 |
| WO | 2007/098212 | 8/2007 |
| WO | 2009117435 | 9/2009 |

OTHER PUBLICATIONS

Written Opinion mailed Sep. 29, 2011, in related International Application No. PCT/US2011/040085, filed Jun. 10, 2011, (6 pages).

"Communication under Rule 71(3) EPC mailed on Dec. 17, 2013", for European Patent Application No. 10779621.1 filed on Nov. 9, 2010, (6 pages).

"PCT International Search Report and Written Opinion", forms PCT/ISA 210, 220 and 237, dated Mar. 5, 2012, for PCT/US2011/052404, filed Sep. 20, 2011, Applicant Entourage Medical Technologies, (26 pages).

"PCT International Search Report and Written Opinion for PCT/US2010/056084", Applicant Entourage Medical Technologies, LLC., Forms PCT/ISA/210, 220, 237, dated May 16, 2011, (11 pages).

* cited by examiner

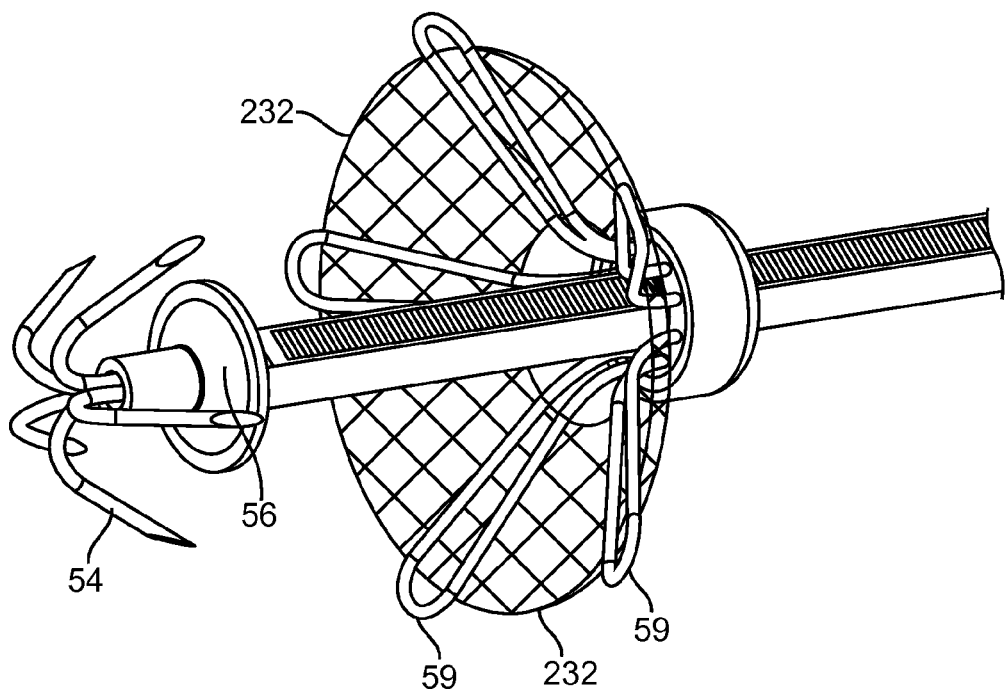
FIG. 3J-i
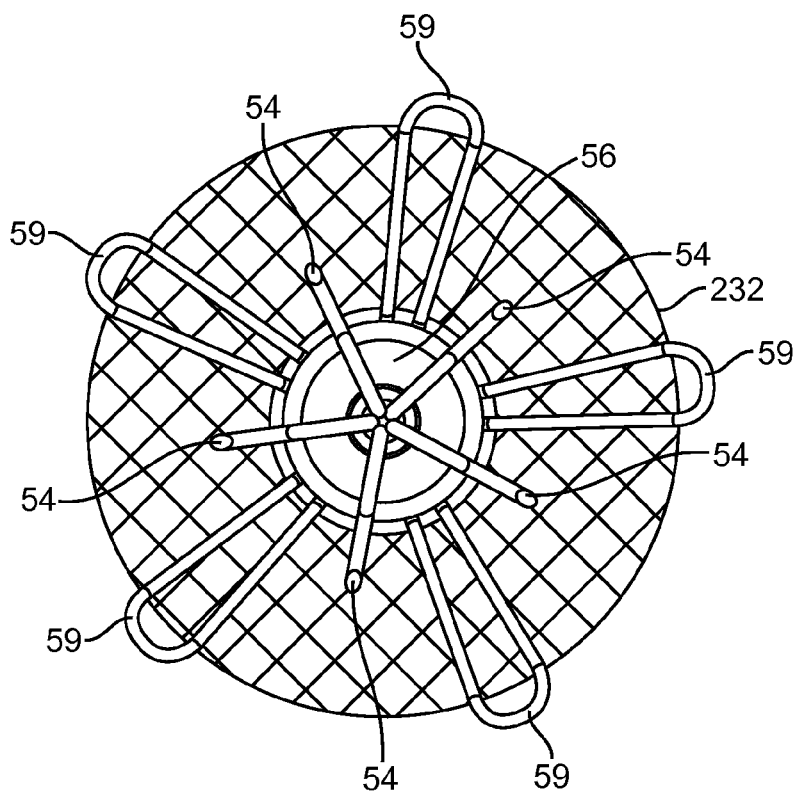
FIG. 3J-ii

SYSTEM AND METHOD FOR TRANSAPICAL ACCESS AND CLOSURE

RELATED APPLICATION DATA

This application is a continuation of U.S. patent application Ser. No. 13/640,041 filed on Oct. 8, 2012 which is a U.S. National Stage filing under 35 U.S.C. §371 of International Application No. PCT/US2011/040085, filed Jun. 10, 2011, which claims priority to U.S. Provisional Application Nos. 61/354,177, filed Jun. 11, 2010 and 61/361,365 filed Jul. 2, 2010. Priority to the aforementioned applications is hereby expressly claimed in accordance with 35 U.S.C. §§119, 120, 365 and 371 and any other applicable statutes.

FIELD OF THE INVENTION

The present invention relates generally to devices and methods for performing cardiovascular procedures, and more specifically to access and closure technologies pertinent to transapical cardiac diagnostic and interventional procedures.

BACKGROUND

Minimally invasive diagnostic and interventional procedure prevalence in US and foreign hospitals continues to increase, as does the demand for certain procedures which involve placement of relatively large devices into targeted locations within tissue structures of criticality. Procedures such as aortic valve replacement conventionally have been addressed with open surgical procedures which are highly invasive. More recently, such procedures have been attempted using natural lumen (i.e., through large blood vessels after an initial surgical transcutaneous or percutaneous access to such vessels) access and delivery systems. Referring to FIG. 1, such systems typically are configured, for example, to reach the aortic valve (12) location inside of the heart (2) from an antegrade approach, which generally requires navigating instrumentation through three of the four chambers of the beating heart (the right atrium 22, left atrium 8, and left ventricle 20, by way of the mitral valve 10 and atrial septum), or from a retrograde approach, which generally requires navigating instrumentation along the aortic arch, from the descending aorta (4) to the ascending aorta (6) and adjacent the aortic valve (12). Each of these approaches presents certain clinical challenges to the surgical team, some of which may be avoided by using what is referred to as a transapical approach, whereby the surgeon creates transcutaneous access to the region around the apex of the heart (26) with a surgical thoracotomy, followed by direct access to the left ventricle (20) using a needle or other device aimed to access the left ventricle (20) around the left ventricular apex (24), which may be followed by one or more dilating instruments to create a temporary access port to the left ventricle. Aspects of a conventional access procedure are illustrated in FIG. 2, wherein a needle device (34) is puncturing the muscular heart wall (30) to gain access to the left ventricle (20) around the location of the left ventricular apex (24). Also shown is a guidewire (36) which may be advanced (38) toward and through the aortic valve (12) to assist with diagnostic and interventional aspects of the procedure. Using these and other instruments such as dilators, this left ventricular access port may be utilized, for example, to replace an aortic valve if bleeding and tissue damage around the access port can be successfully mitigated during such procedure. Subsequent to such a procedure, the instrumentation needs to be removed and the access port closed, usually leaving a prosthetic valve or portion thereof behind. The successful closure of a transapical wound on a beating heart of a patient is obviously of high criticality to such a procedure, as is the minimization of loss of blood. Conventional transapical closure techniques typically involve the placement of small sutures to create a purse-string type effect to close the wound as the instrumentation is withdrawn, and it may be very difficult to repeatably create acceptable closures using these techniques without a larger thoracotomy or improved instrumentation. In other words, one of the key challenges to transapical intervention remains transapical wound closure. Indeed, it is believed that transapical access may provide enhanced stability and control during procedures such as aortic valve replacement, due to the fact that the operator may have a relatively direct mechanical connection with the pertinent instrumentation, relative to the connection that he may have using, for example, an antegrade or retrograde vascular approach with more compliant catheter type tools. For this reason, it is even more desirable to successfully address the challenges of transapical access and closure.

SUMMARY OF THE INVENTION

One embodiment is directed to an apparatus for closing a defect in a tissue wall, comprising a base member having a proximal end and a distal end and a seal member disposed therebetween, the proximal end being configured to be manually manipulated by an operator; wherein the seal member defines an outer seal margin defining an outer seal diameter; a first plurality of bendable strut members coupled to the distal end of the base member and configured to occupy a collapsed configuration when bent in place toward the base member, and an expanded configuration when unrestrained; wherein in the collapsed configuration, each of the bendable strut members project out from a coupling junction with the distal portion of the base member, sweep toward the proximal end of the base member, and bend toward the outer seal margin; a proximal hub member movably coupled to the base member and advanceable along a length of the base member; and a second plurality of bendable strut members coupled to the proximal hub member and configured to occupy a collapsed configuration when bent in place toward the base member, and an expanded configuration when unrestrained; wherein in the collapsed configuration, each of the bendable strut members project out from a coupling junction with the proximal hub member and sweep toward the distal end of the base member. The apparatus further may comprise a tubular delivery member defining a delivery lumen through which the base member, first plurality of bendable strut members in a collapsed configuration, proximal hub member, and second plurality of bendable strut members in a collapsed configuration may be advanced by inserting the base member relative to the tubular delivery member. The tubular delivery member may have an outer diameter configured to be inserted through a defect created in the tissue wall, such that the base member may be further inserted to place the first plurality of bendable strut members past the tissue wall, out of the delivery lumen, and into the expanded configuration of the first plurality of bendable strut members. The first plurality of bendable strut members, upon expansion to the expanded configuration, may occupy an expanded shape having a larger diameter than that of the tubular delivery member. The base member may comprise an elongate shape with movement-controlling features configured to controllably resist movement of the proximal hub member relative to the base member. The outer seal margin may have a substantially circular shape. The first plurality of bendable strut members may comprise two or more elongate members with proximal ends fixedly coupled to the distal end of the base member in a cantilevered anchoring configuration, and distal ends that are free to move subject to the cantilevered proximal anchoring configuration. The distal ends of the bendable strut members may be sharpened. The bendable strut members comprising the plurality may be substantially equally radially distributed about a longitudinal axis of the distal end of the base member. The first plurality of bendable strut members may comprise one pair of bendable strut members. The first plurality of bendable strut members may comprise three or more bendable strut members. The first plurality of bendable strut members may comprise nitinol alloy. The second plurality of bendable strut members may comprise two or more elongate members with proximal ends fixedly coupled to the proximal hub member in a cantilevered anchoring configuration, and distal ends that are free to move subject to the cantilevered proximal anchoring configuration. The distal ends of the bendable strut members may be sharpened. The second plurality of bendable strut members may comprise two or more elongate members with proximal ends fixedly coupled to the proximal hub member in a cantilevered anchoring configuration, and distal ends which are joined in an atraumatic loop configuration. The second plurality of bendable strut members may comprise nitinol alloy. The apparatus may further comprise a cannula defining an interior lumen and having an outer diameter, wherein the interior lumen is sized to movably accommodate the tubular delivery member, and wherein the outer diameter is sized to be insertable through the defect created in the tissue wall. The apparatus may further comprise a fabric member coupled to the second plurality of bendable strut members and configured to spread loads which may be applied to said strut members by adjacent tissue structures.

DETAILED DESCRIPTION

Figure 3A:
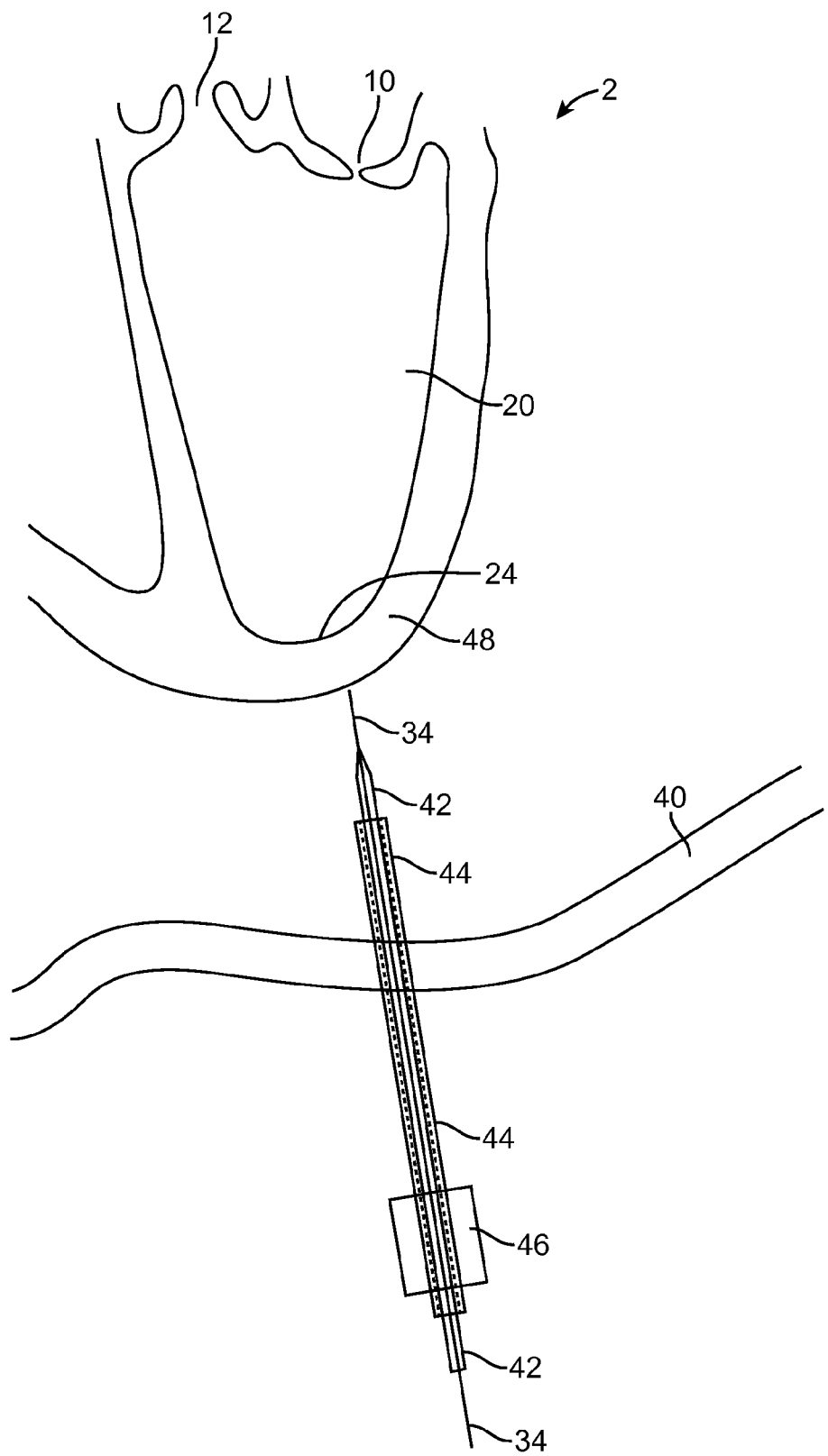
FIGS. 3A to 3Z-3 illustrate various aspects of various embodiments of a system for creating transapical access for a diagnostic and/or interventional procedure, and closing following such procedure.
Figure 3B:
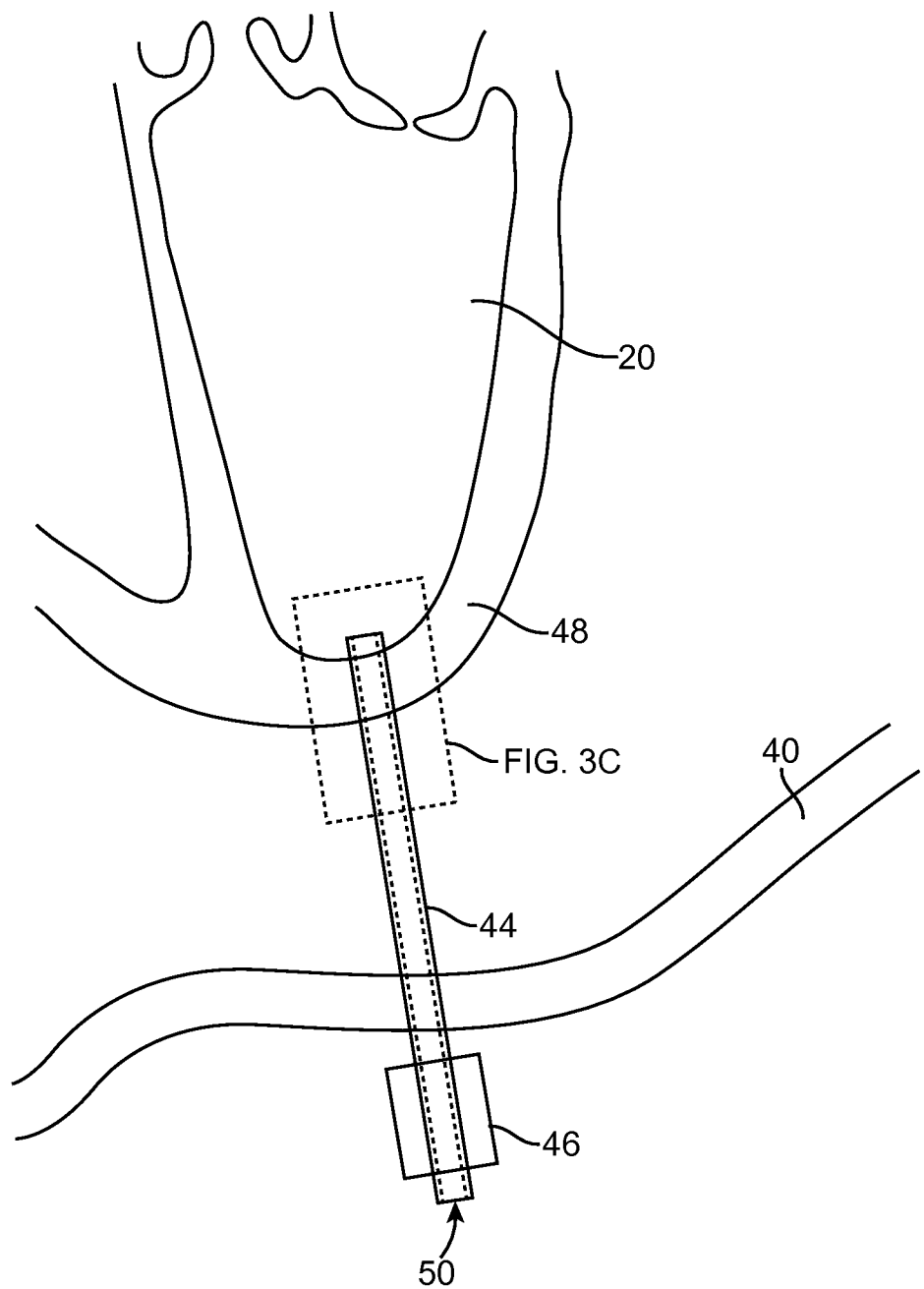
Figure 3C:
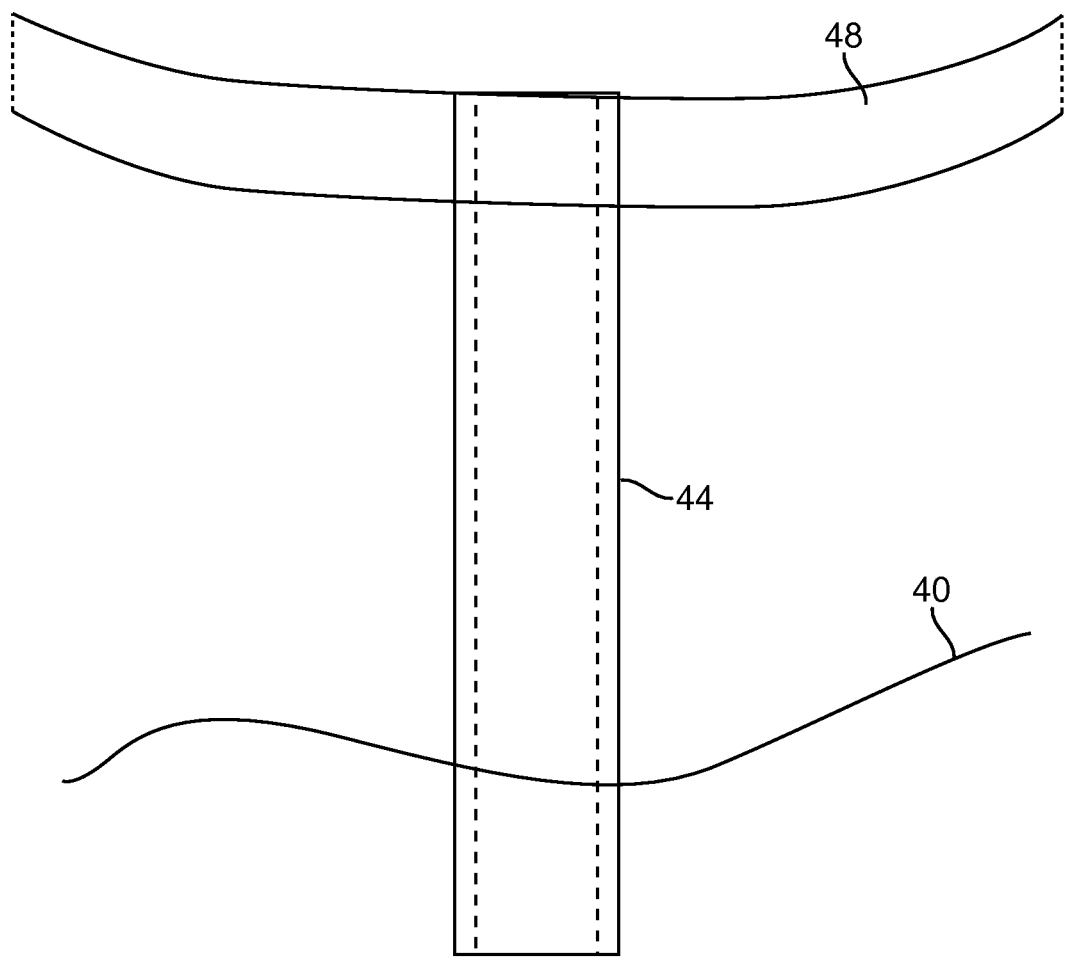
Figure 3D:
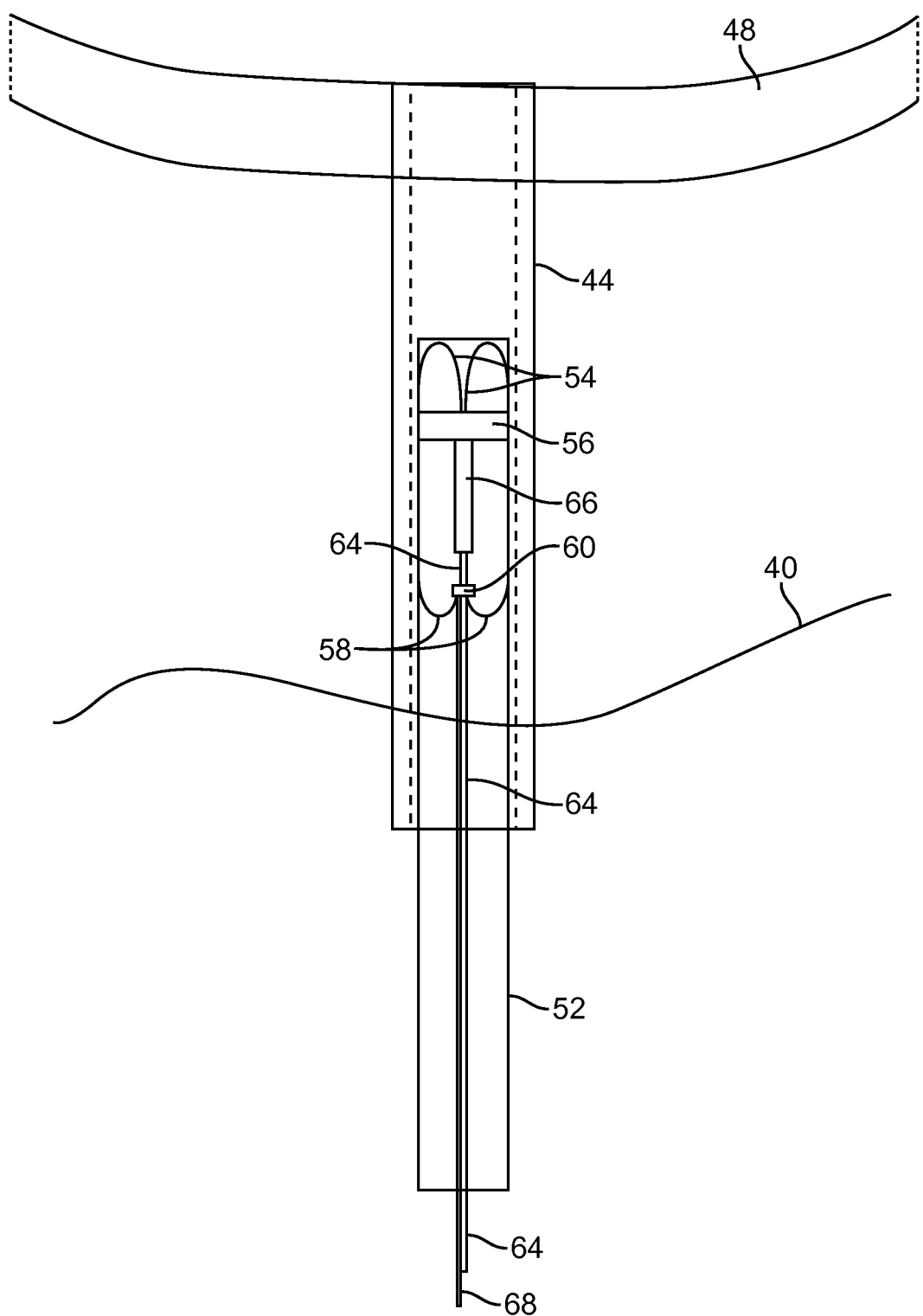
Figure 3E:
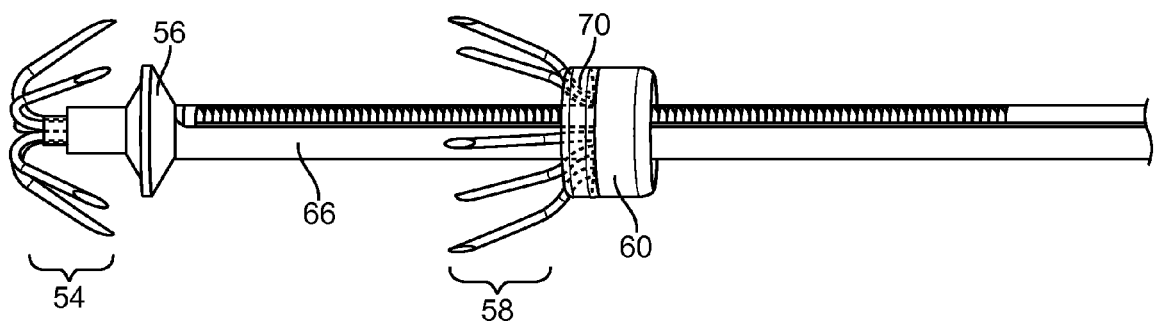
Figure 3F:
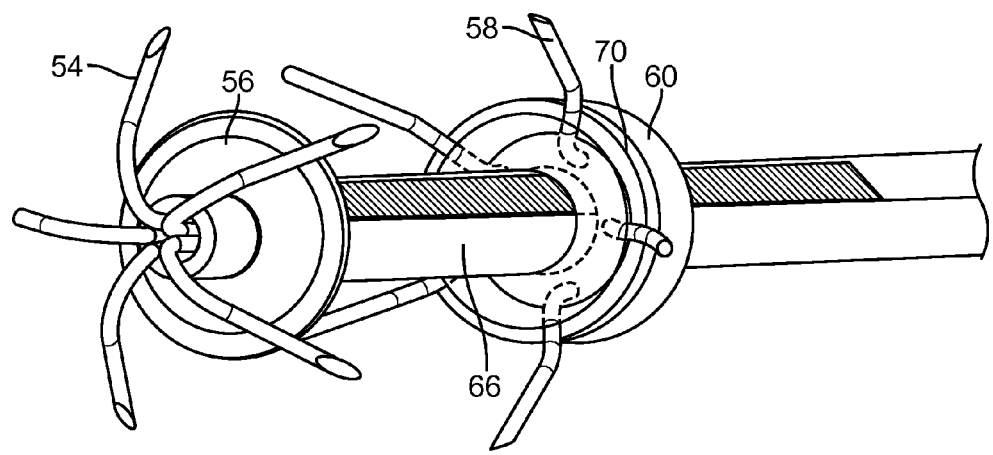
Figure 3G:
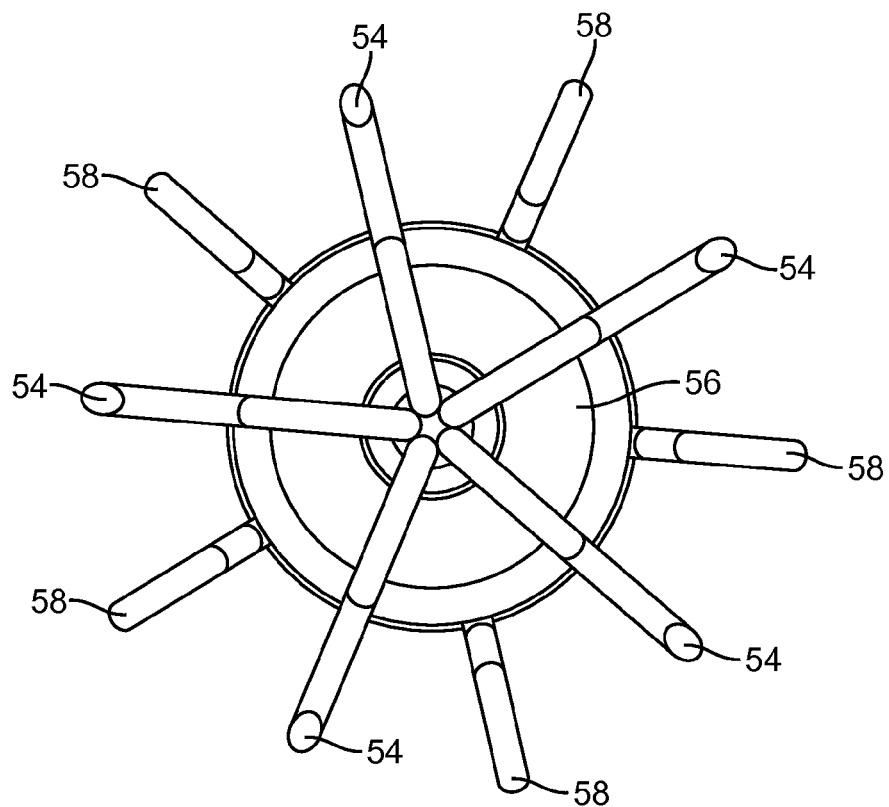
Figure 3H:
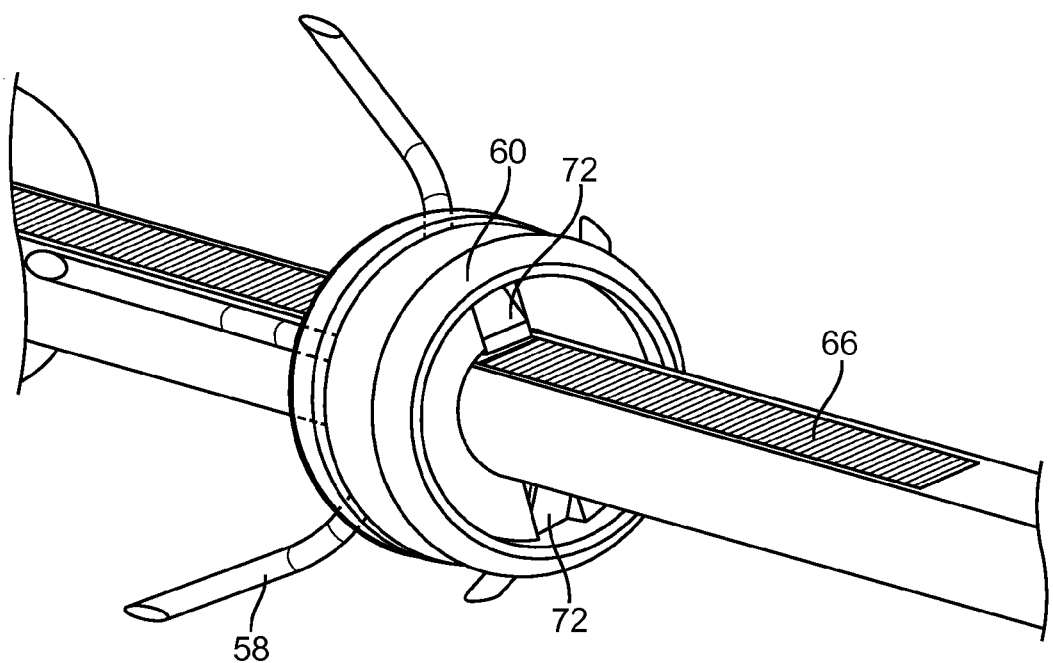
Figure 3I:
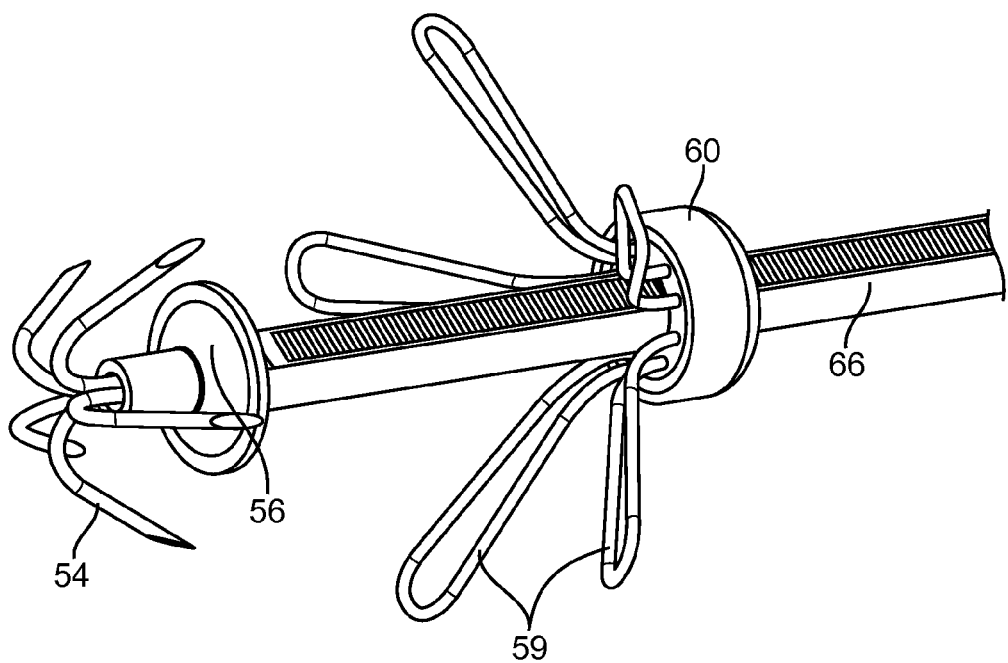
Figure 3J:
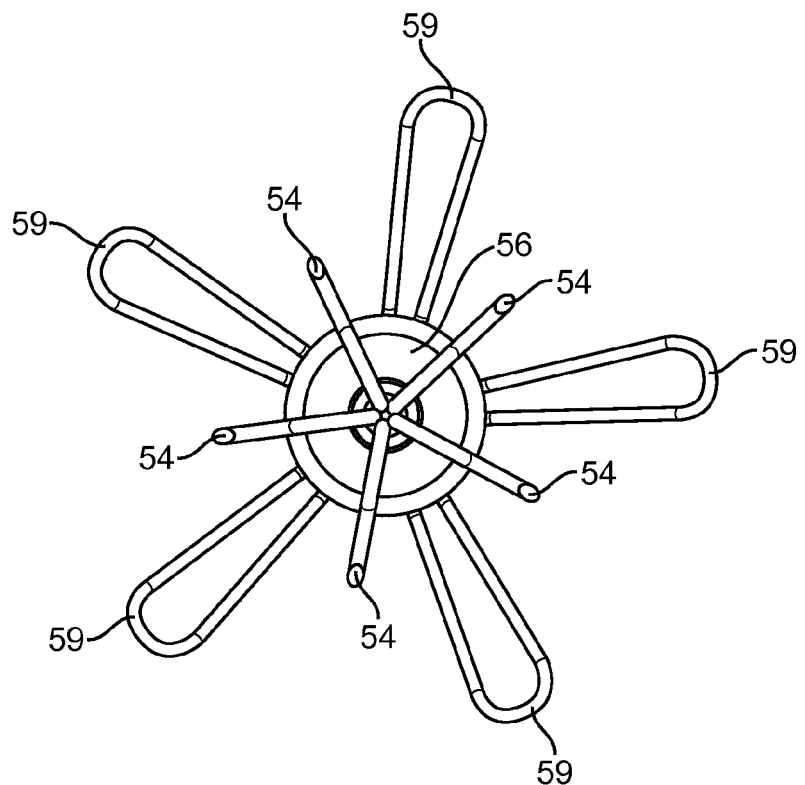
Figure 3K:
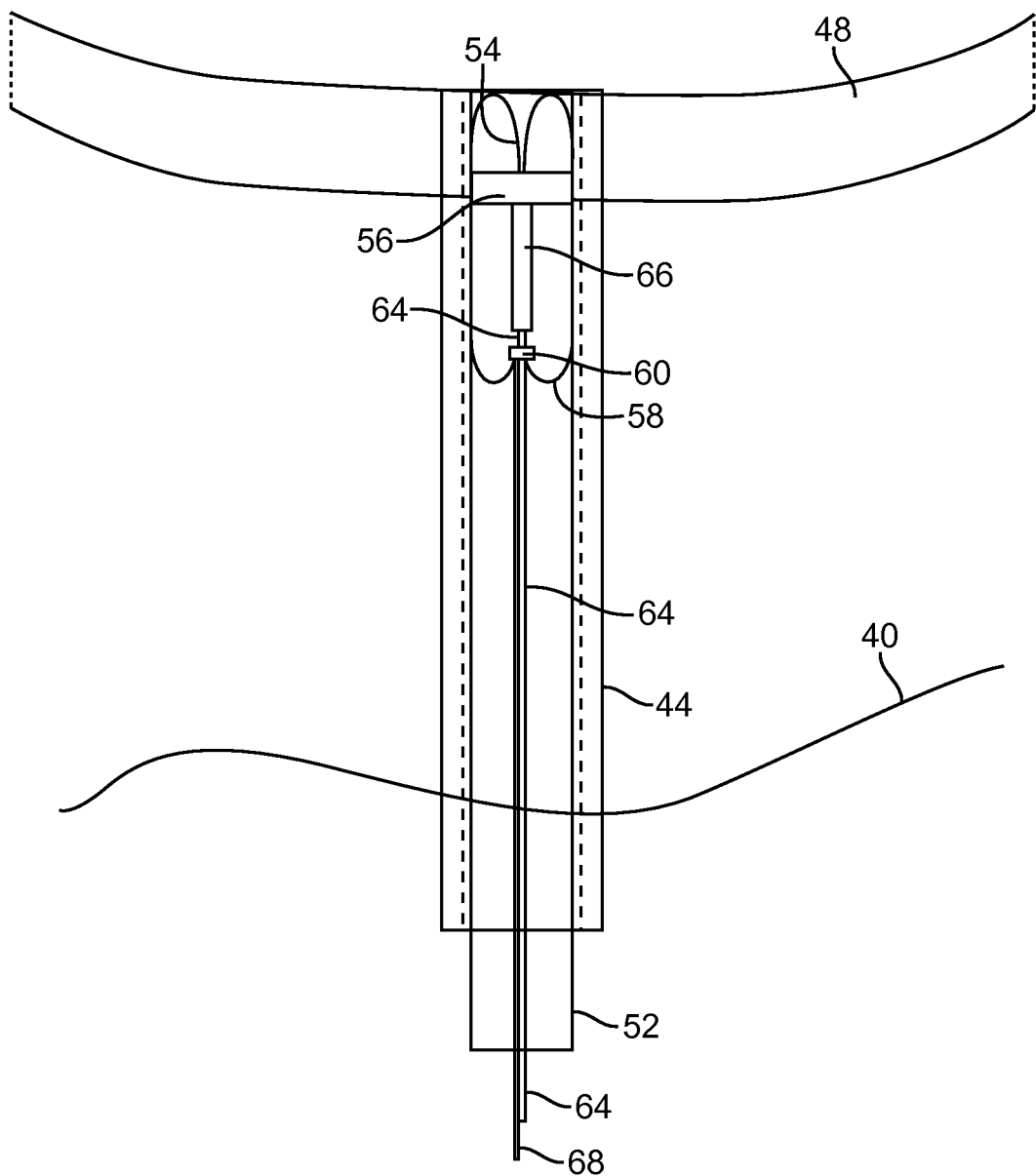
Figure 3L:
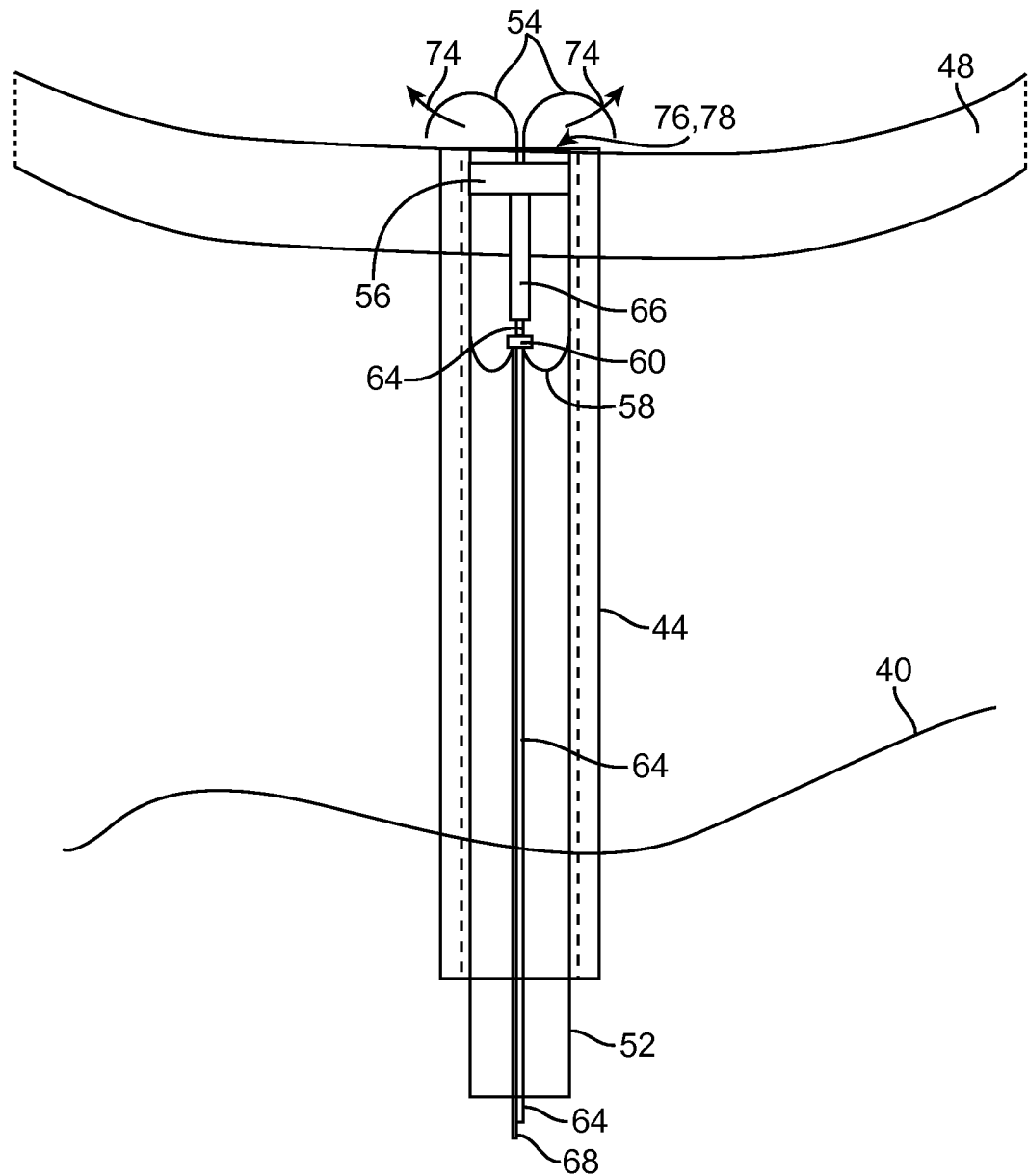
Figure 3M:
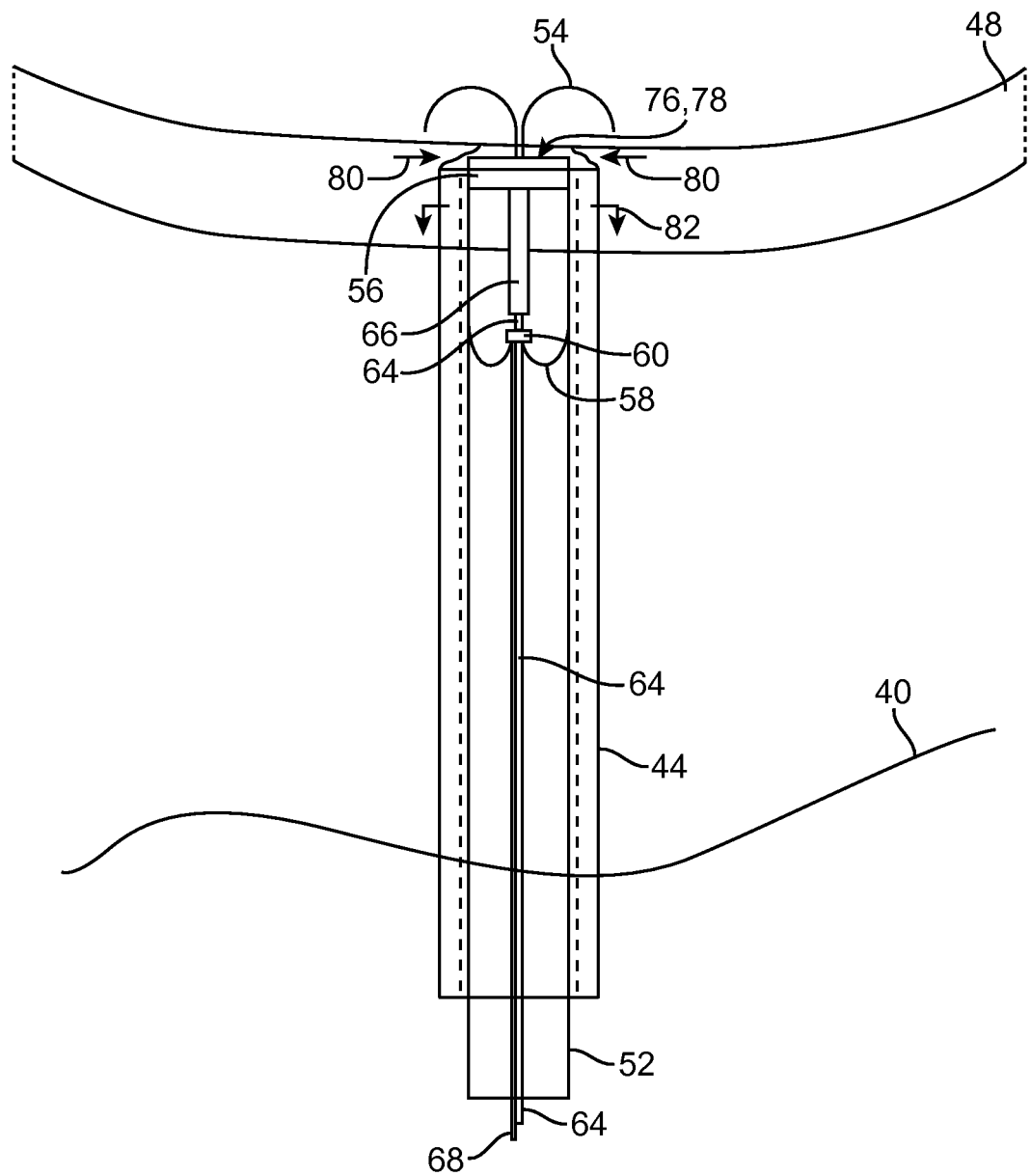
Figure 3N:
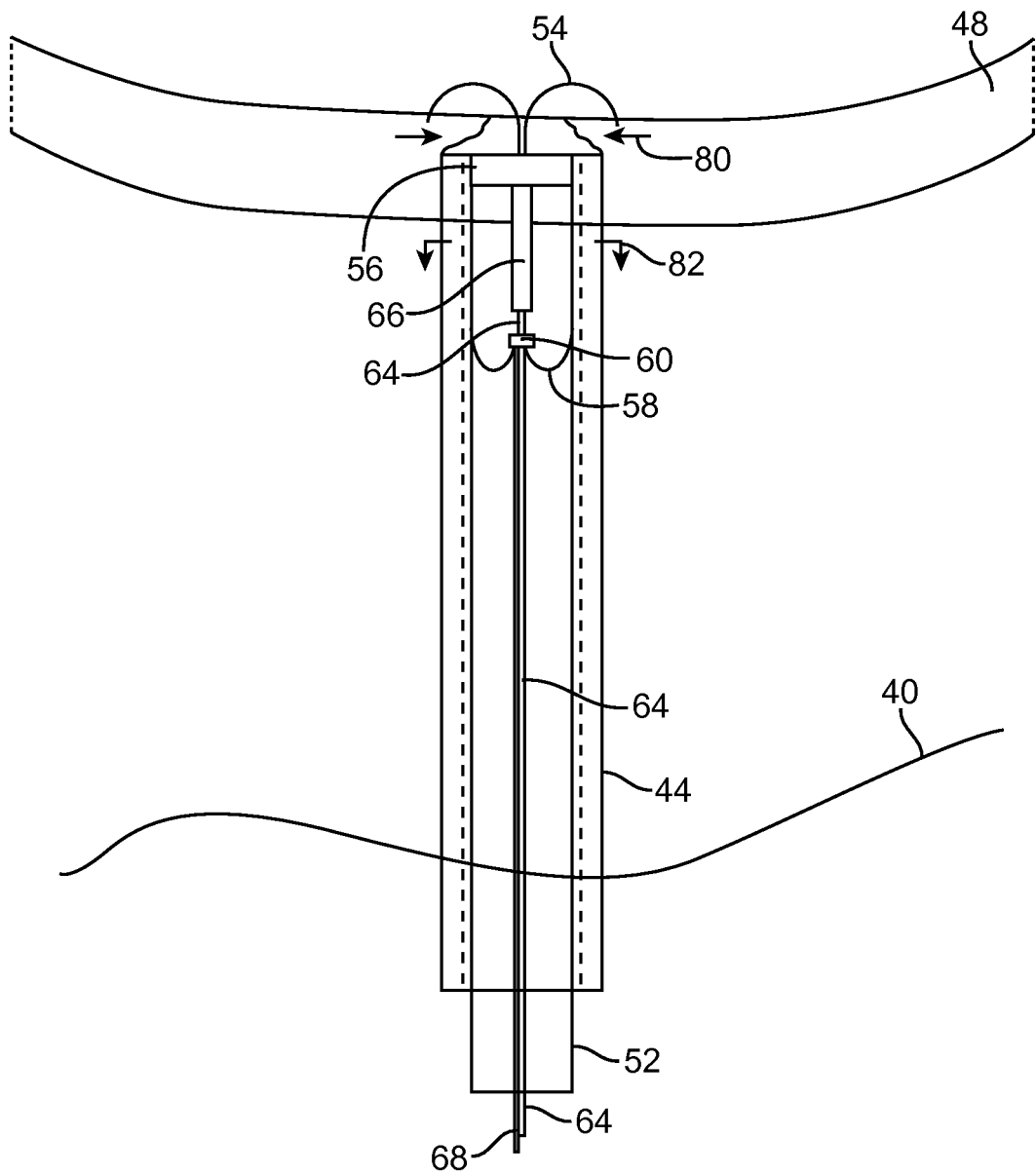
Figure 3O:
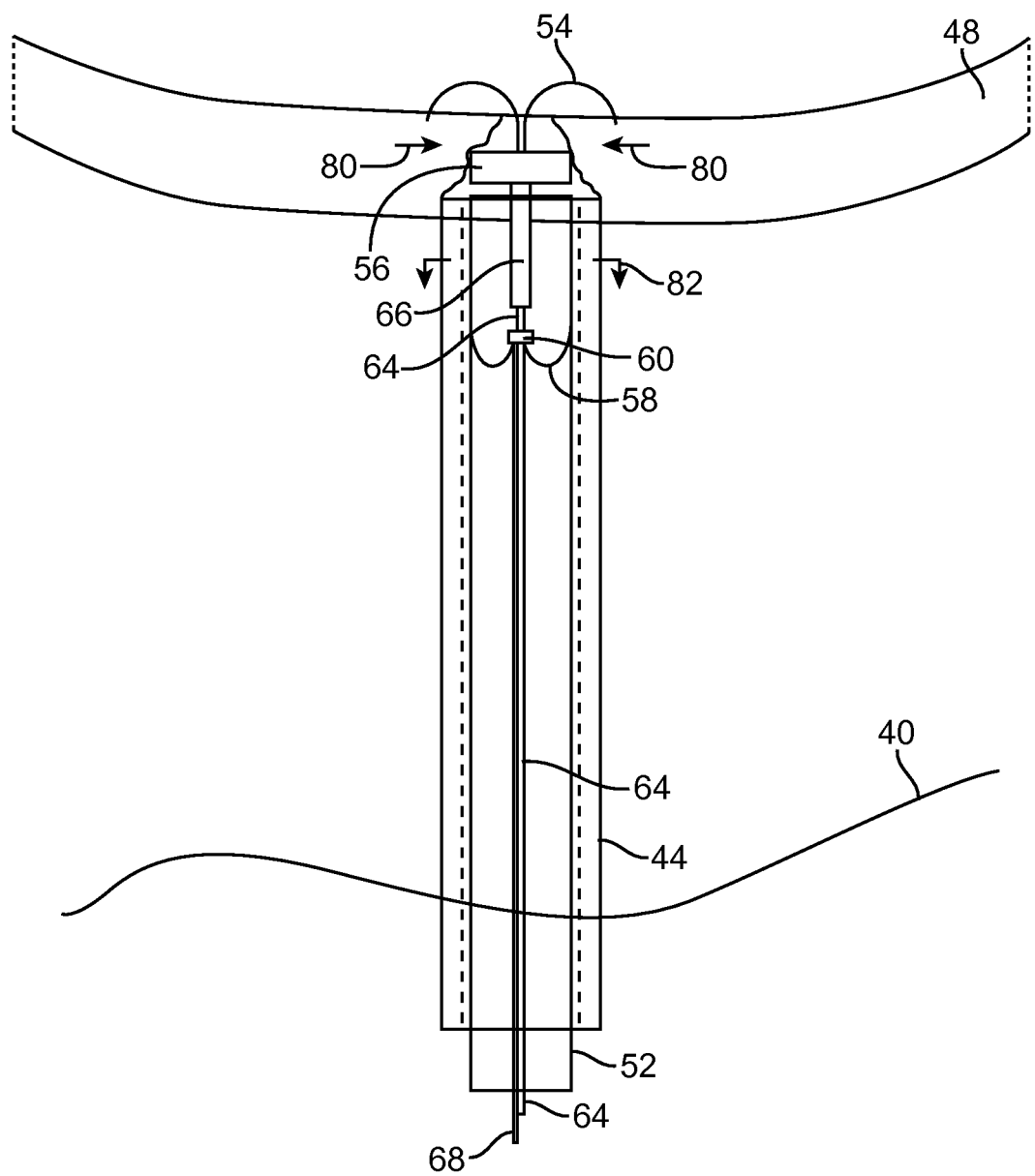
Figure 3P:
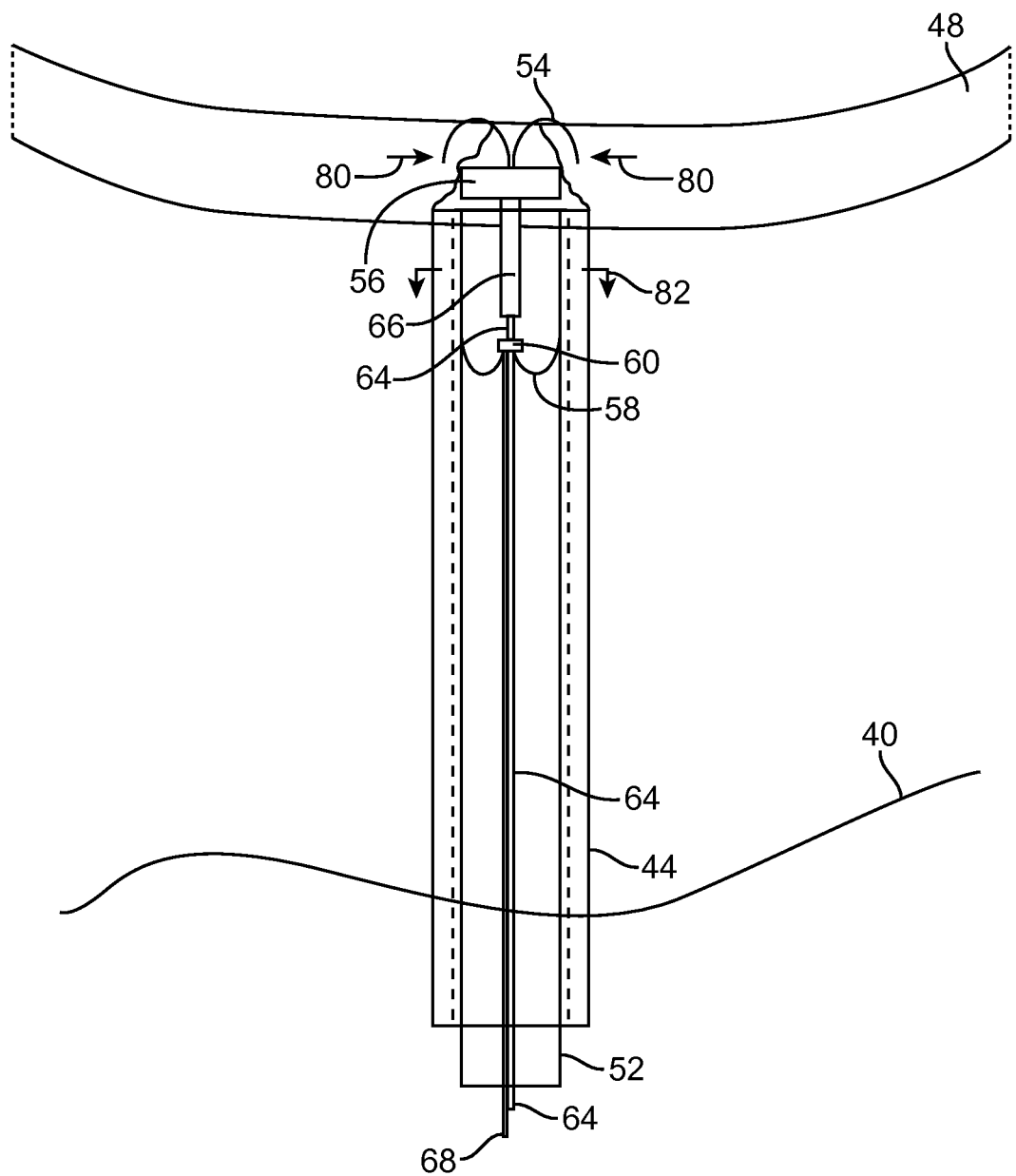
Figure 3Q:
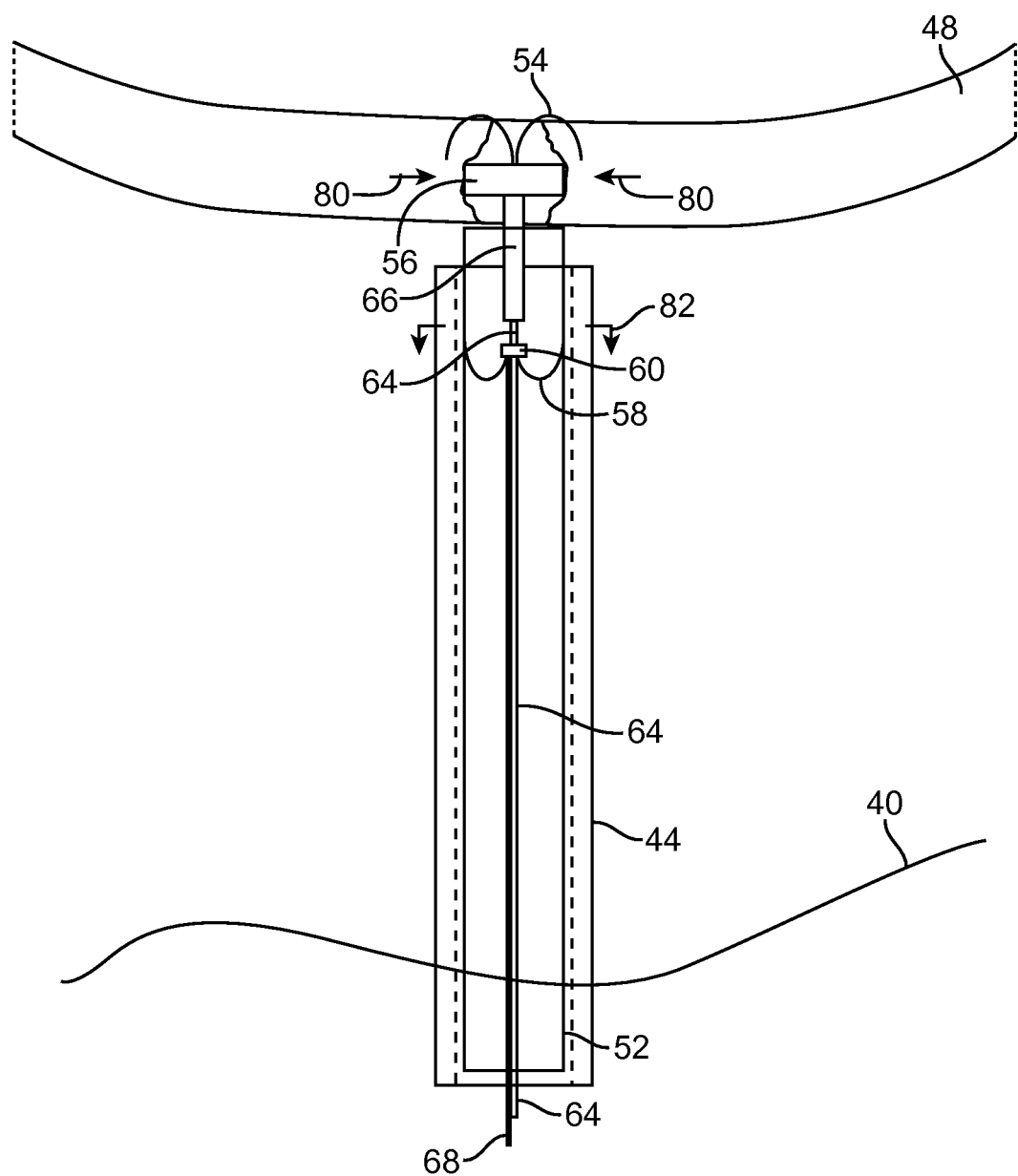
Figure 3R:
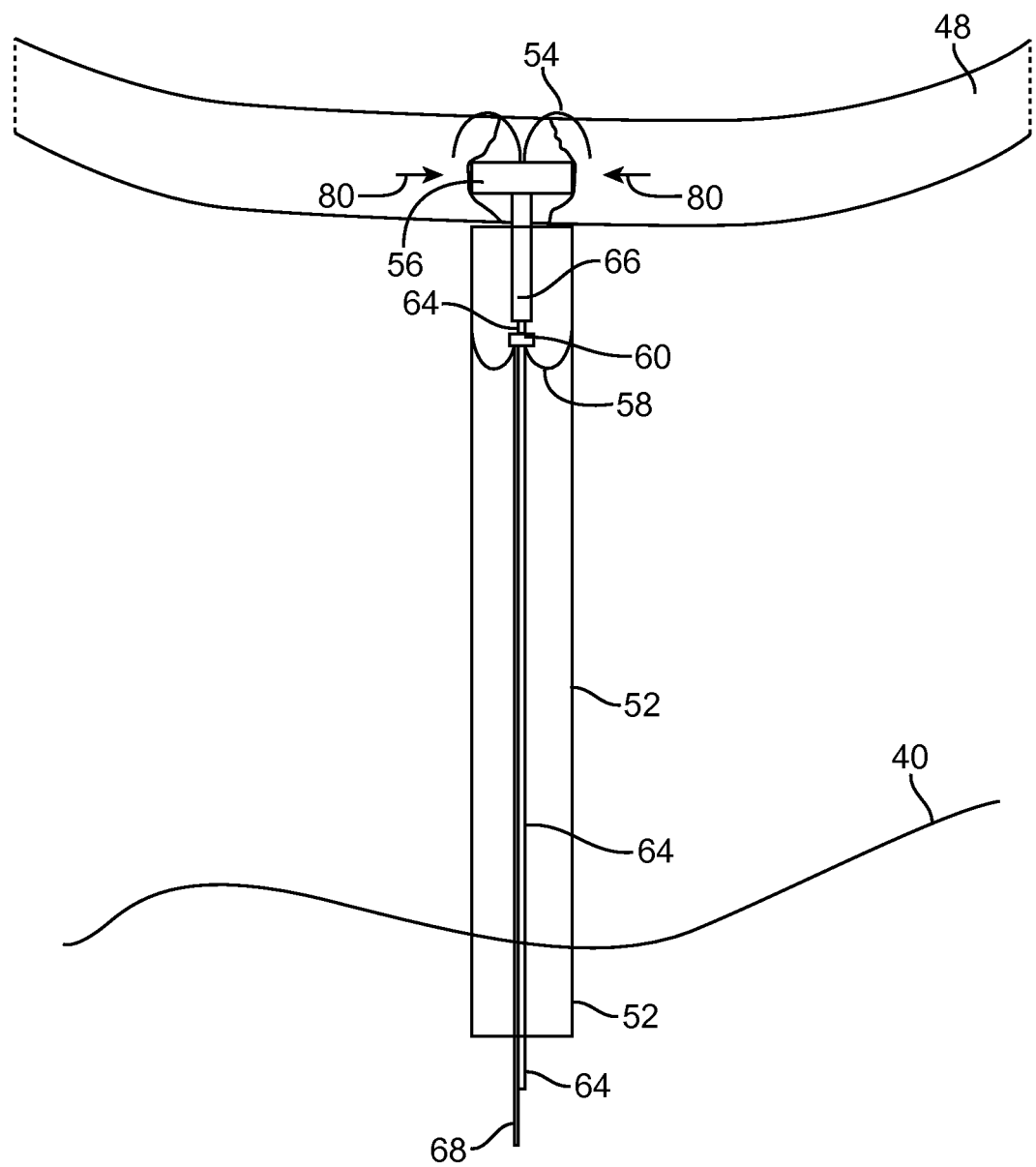
Figure 3S:
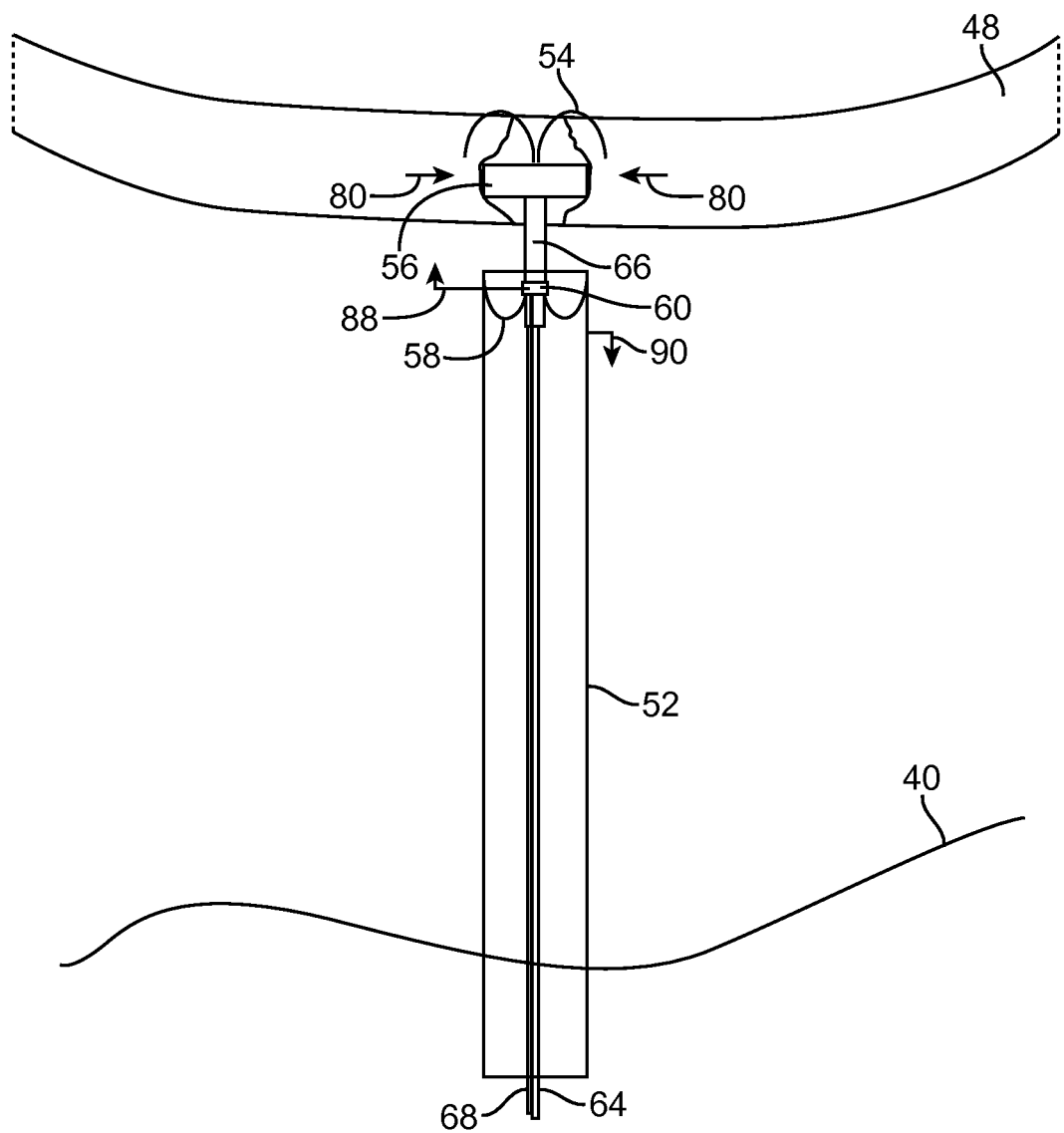
Figure 3T:
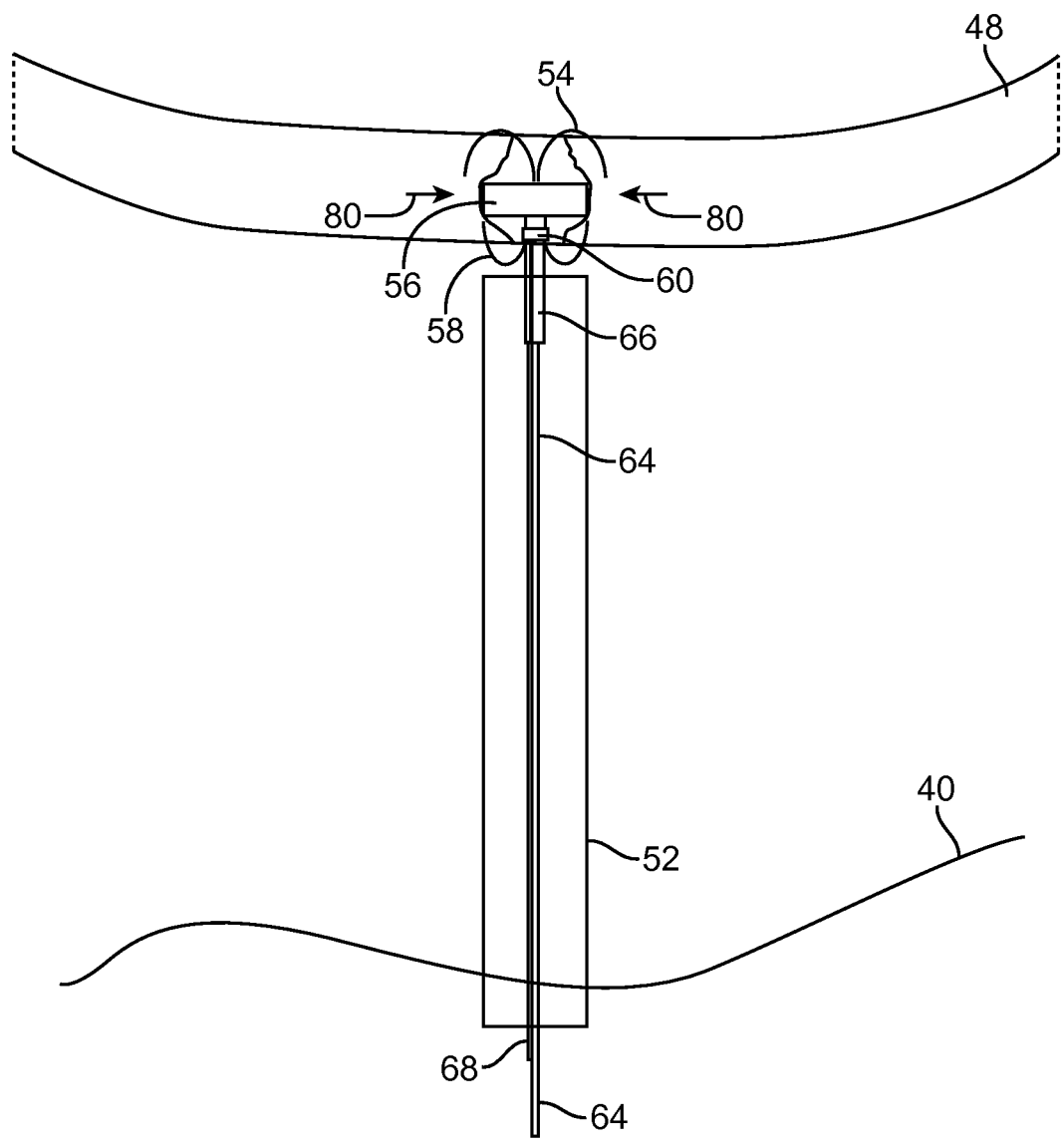
Figure 3U:
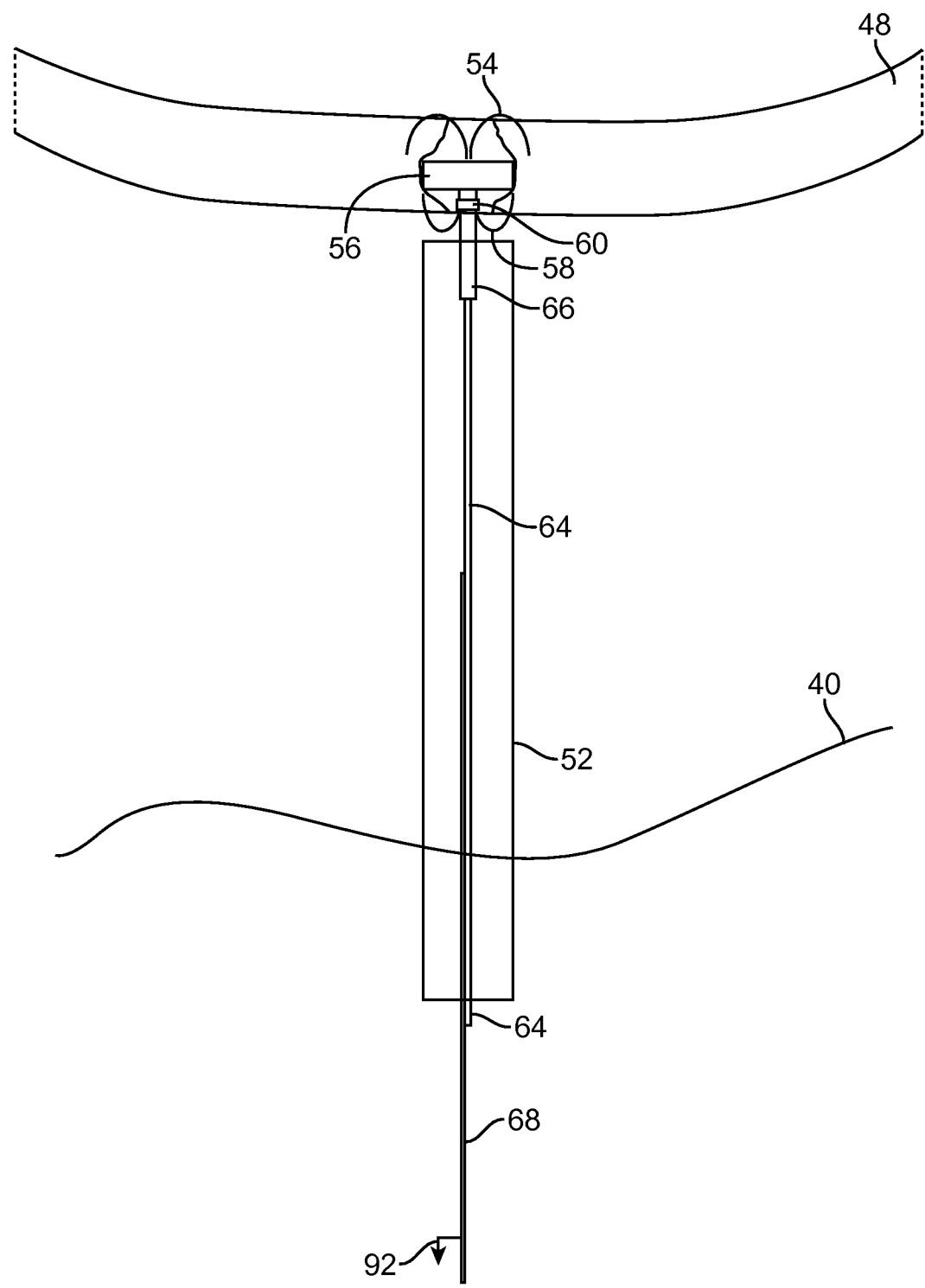
Figure 3V:
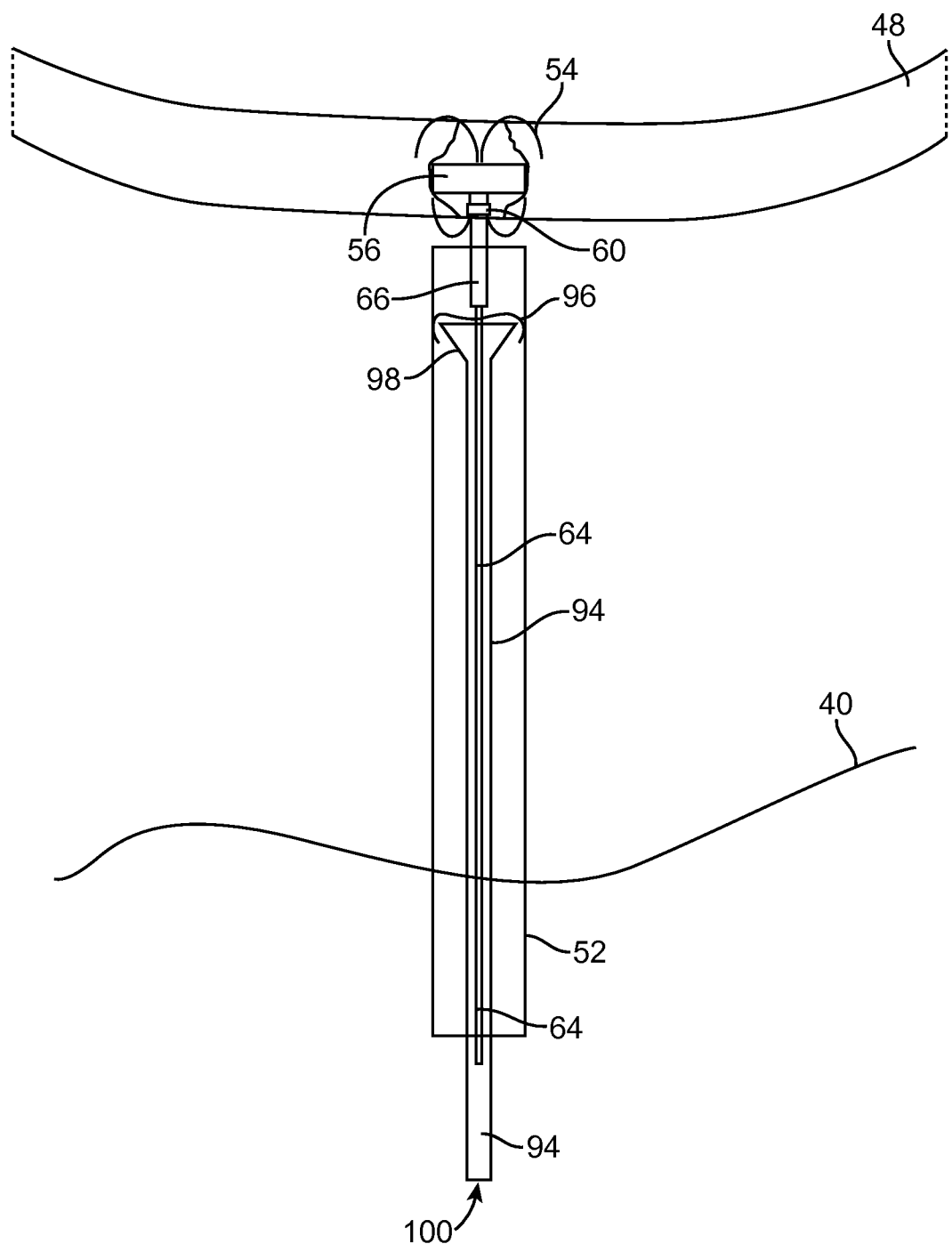
Figure 3W:
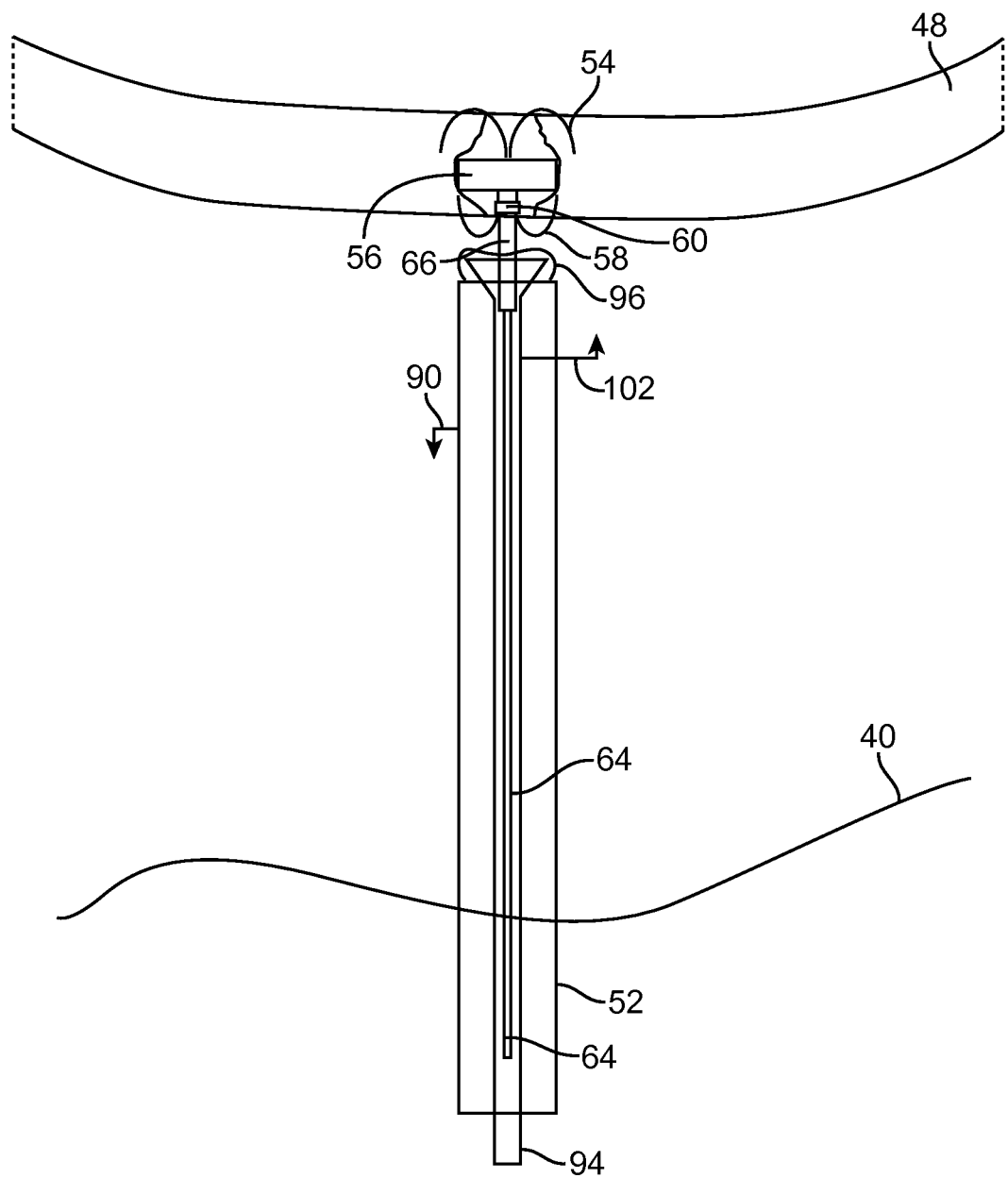
Figure 3X:
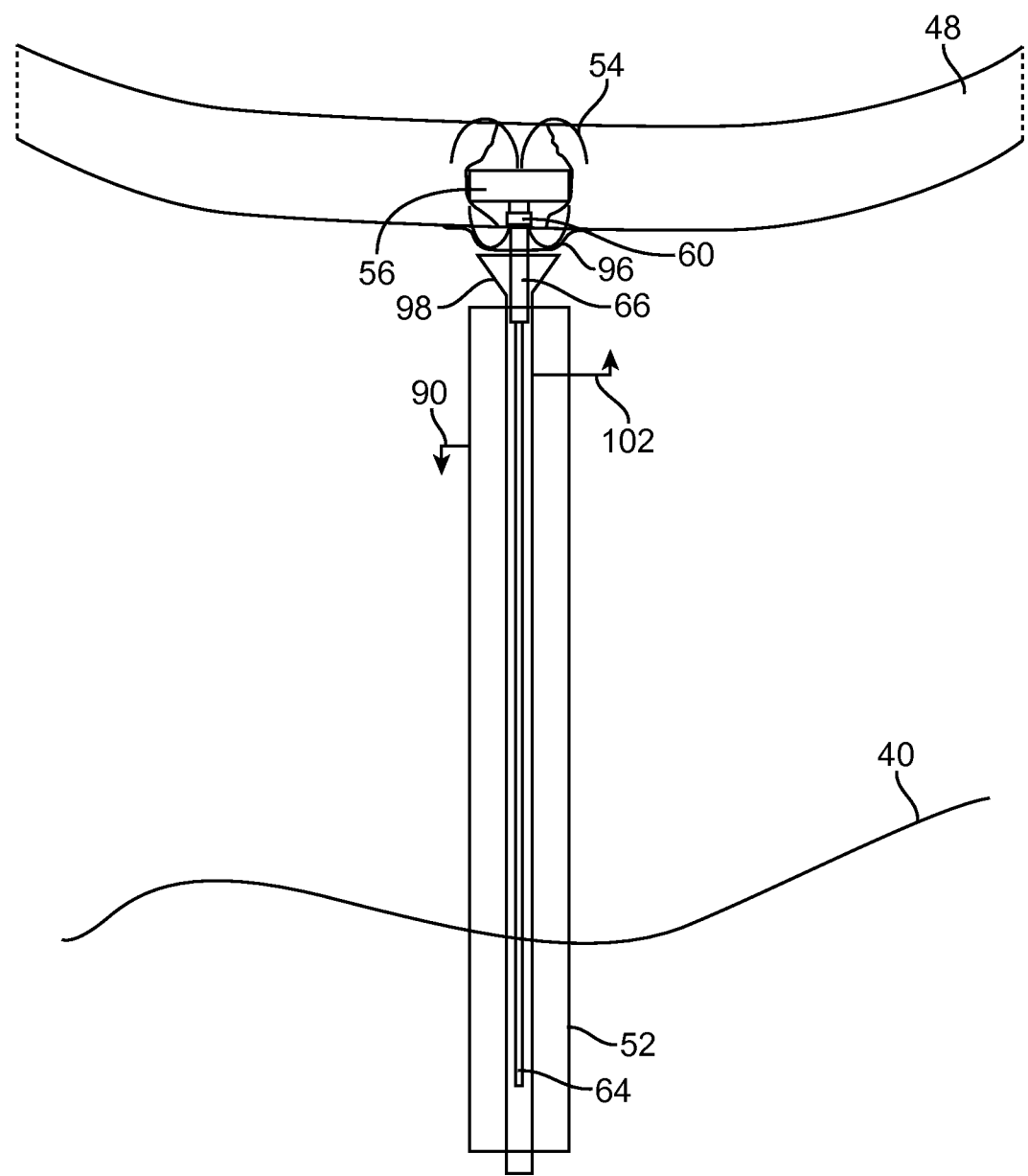
Figure 3Y:
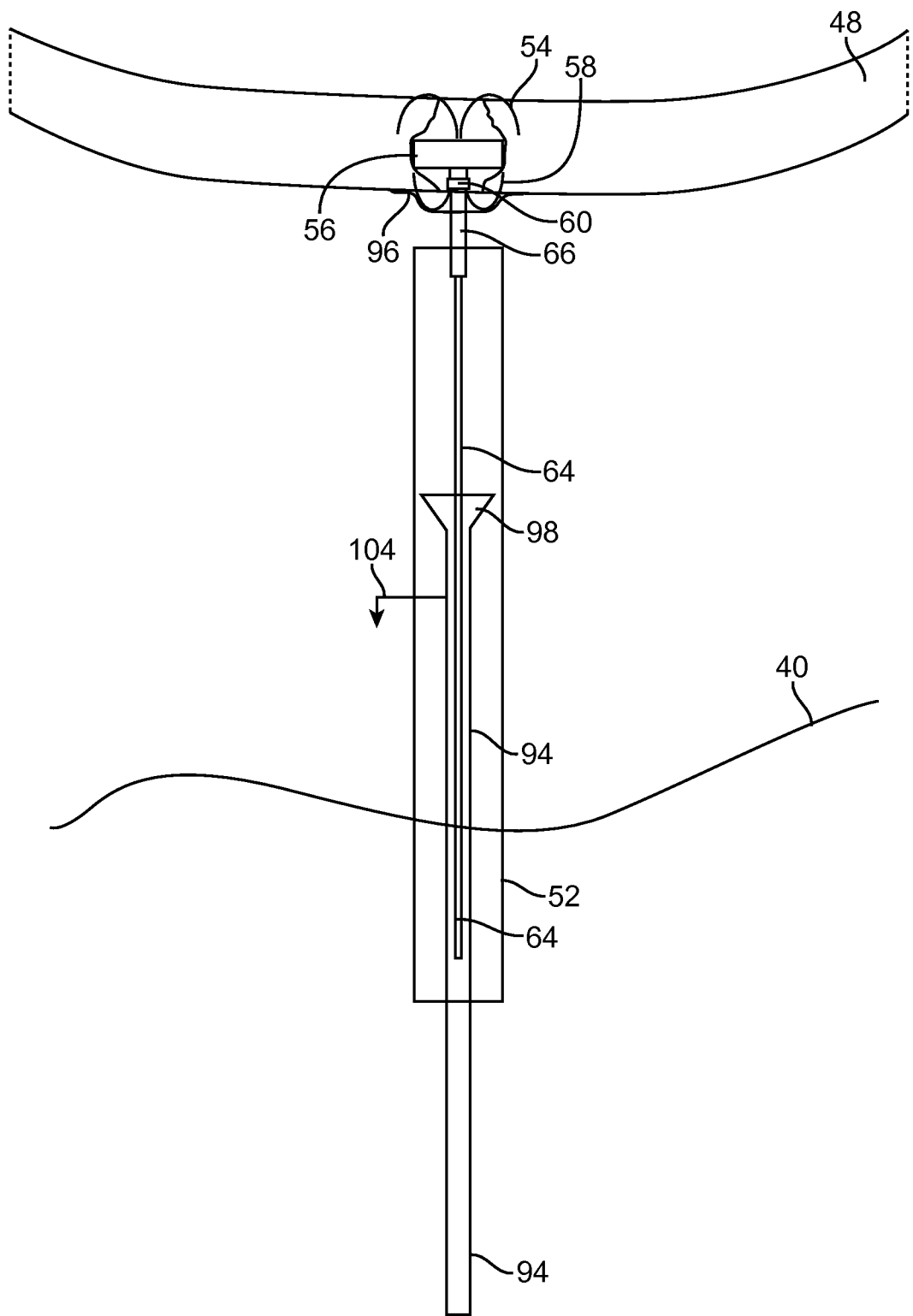
Figure 3Z:
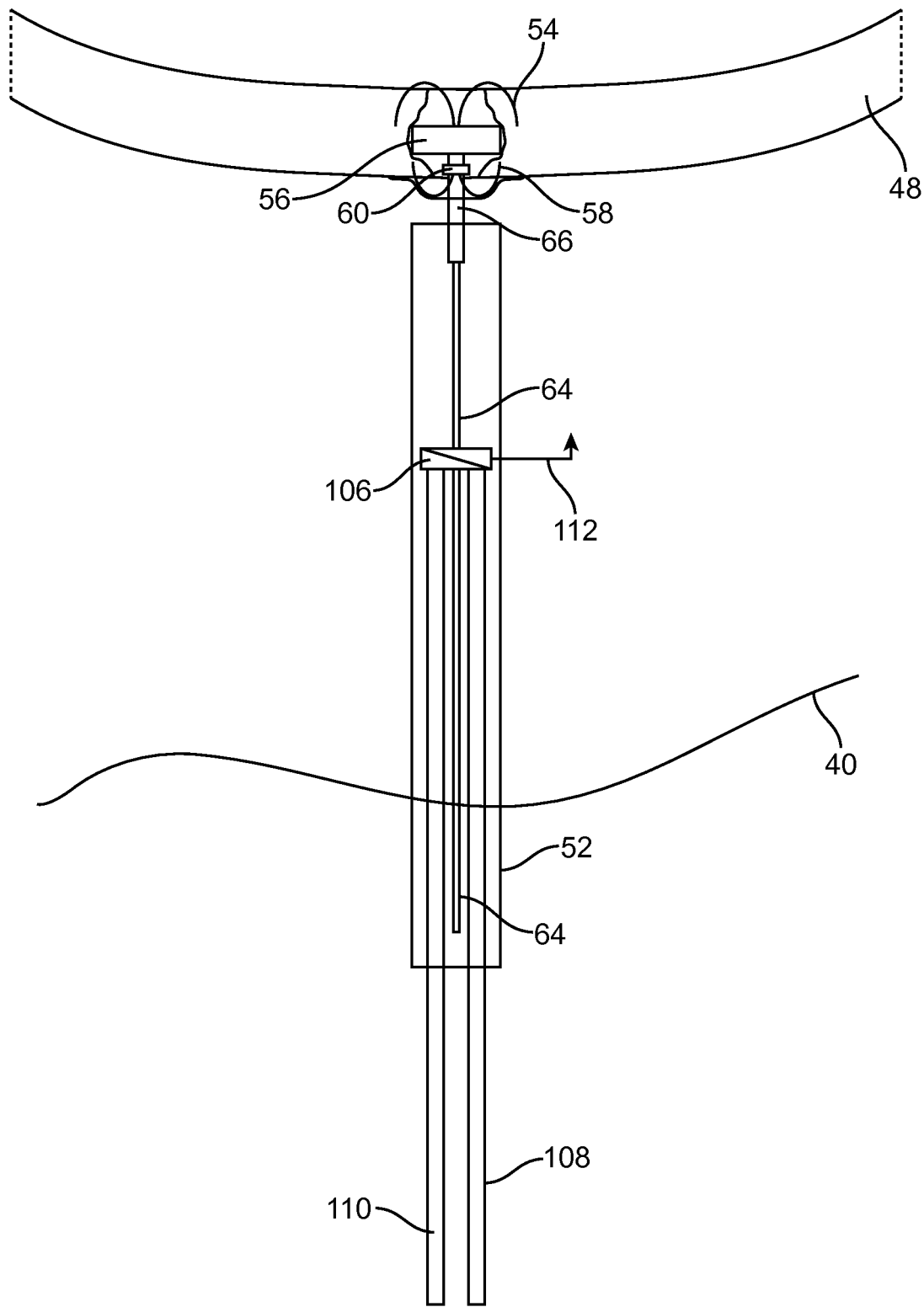
Figures 1, 3Z:
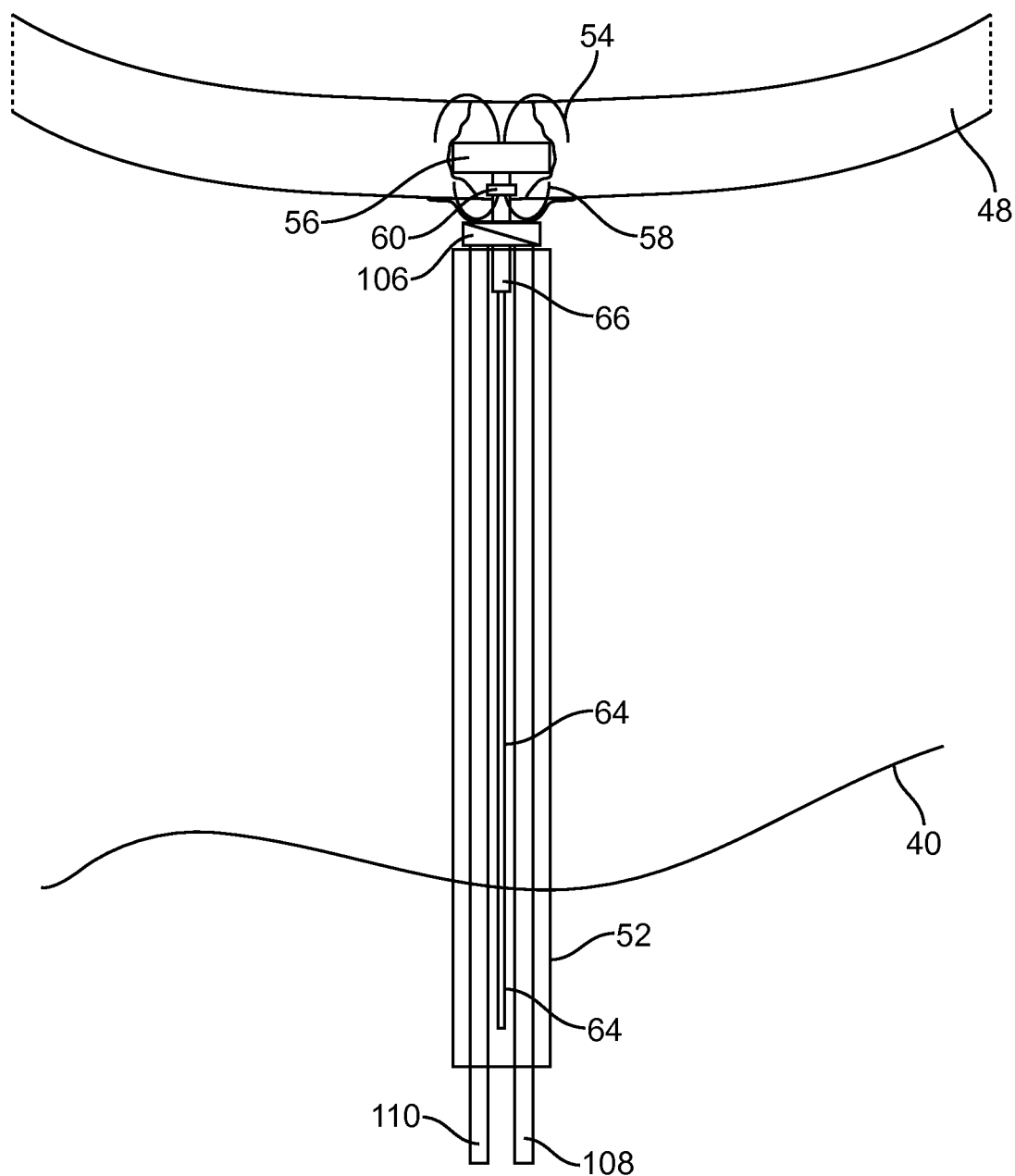
Figures 2, 3Z:
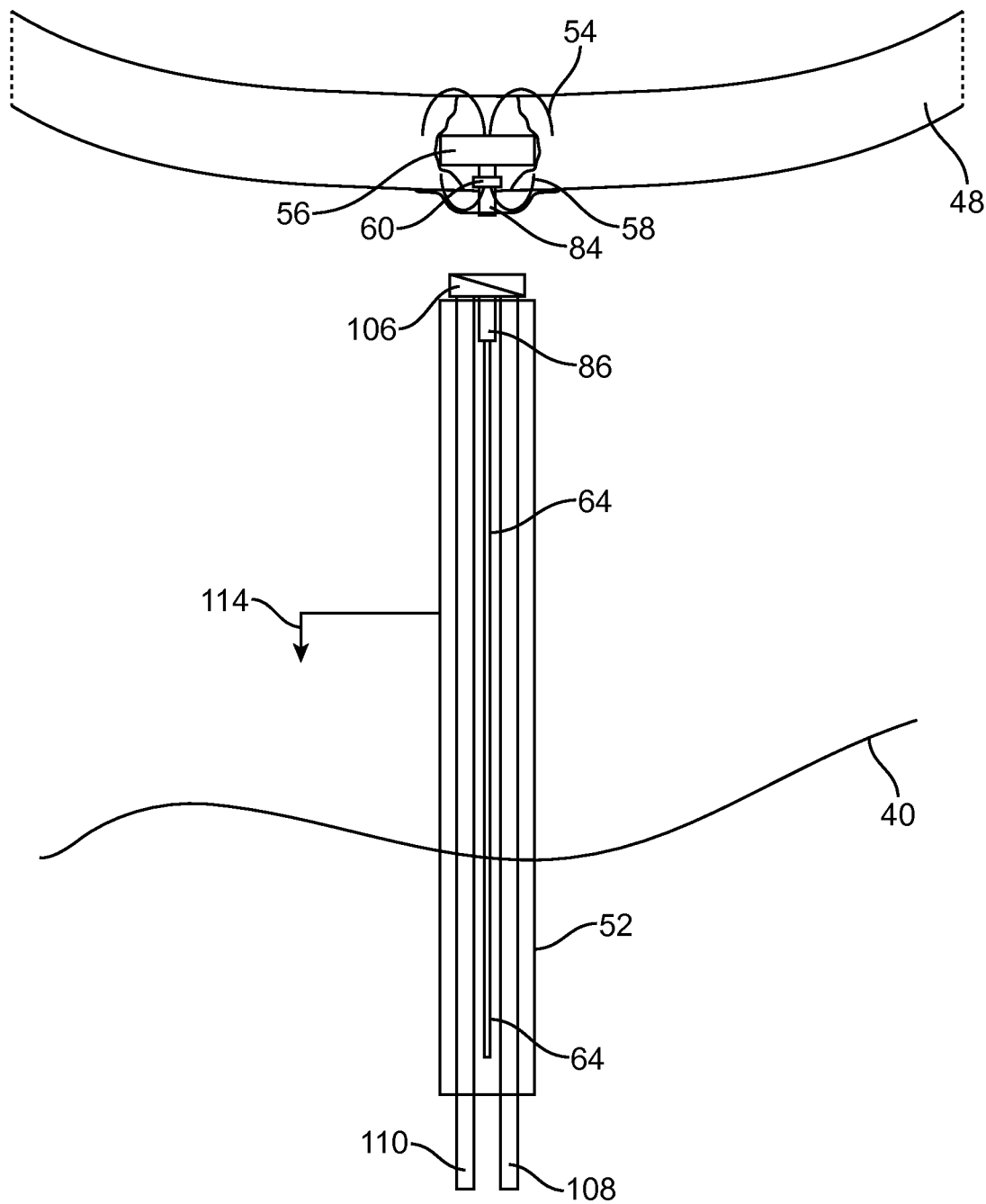
Figures 3, 3Z:
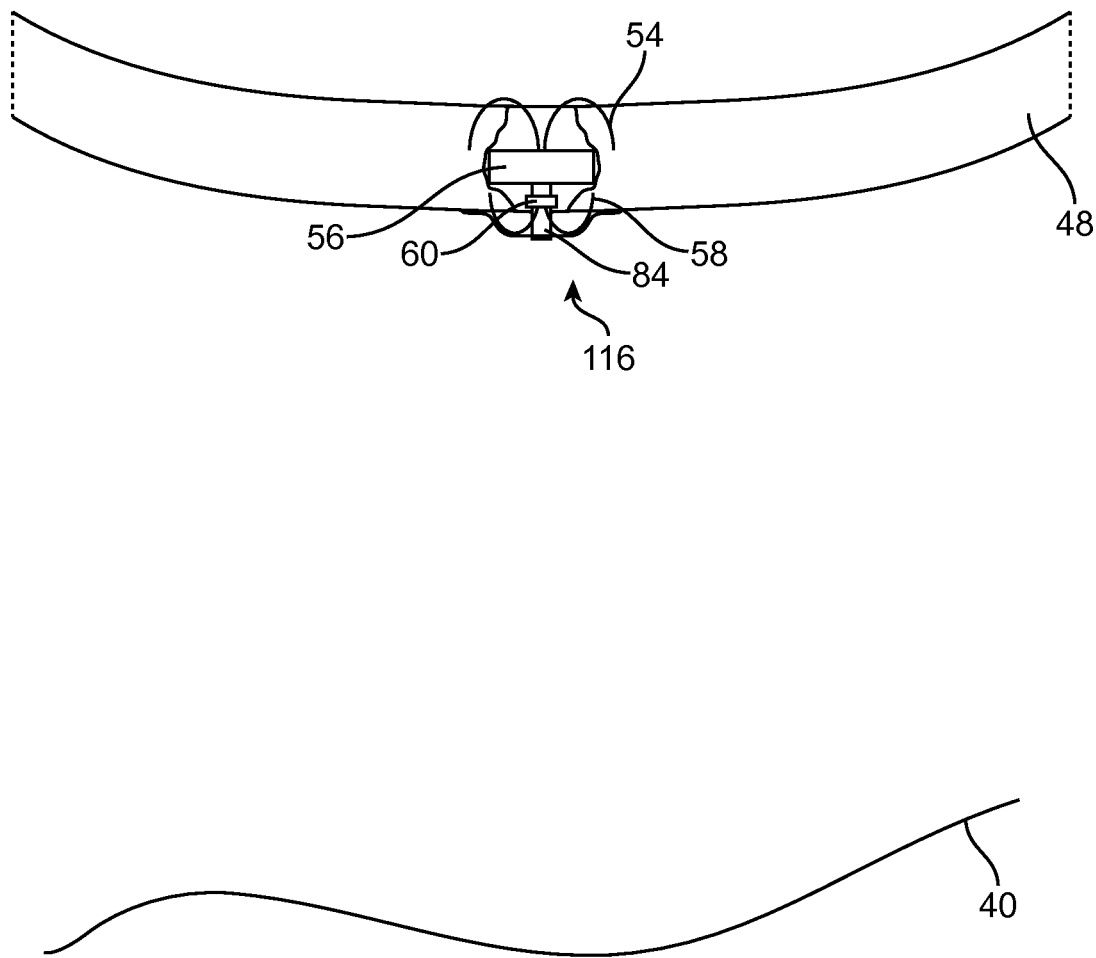

Referring to FIGS. 3A through 3Z-3, various aspects of embodiments of a transapical access and closure system are depicted. As shown in FIG. 3A, a transapical access assembly is depicted comprising a needle (34) placed through an elongate dilator member (42), which is slidably positioned through a working lumen of an introducer sheath (44) which may be manipulated using a proximal handle or hub (46). The assembly has been placed through a thoracotomy created in the chest wall (40) of a patient, and directed toward a location on the heart (2) that is determined to be close to the apex (24) of the left ventricle (20) using information derived from sources such as anatomic markers, preoperative diagnostic imaging information, such as radiography and/or fluoroscopy, and intraoperative imaging information derived, for example, from radiography, endoscopy, and/or fluoroscopic imaging of portions of the access assembly which may be radioopaque (or radioopaque markers which may be fastened to portions of the assembly in one embodiment). Referring to FIG. 3B, after the needle (34) has been inserted across the wall (48) of the left ventricle (20), the dilator (42) followed over the needle, and the introducer sheath (44) followed over the dilator, the needle and dilator may be withdrawn, and the introducer (44) left in place to provide transapical access. The needle preferably comprises a conventional stainless steel needle of approx 18 gauge and may be fitted with radioopaque markers at known graduated positions and the distal tip. The introducer may comprise an off-the-shelf transapical sheath having a working lumen (50) diameter of between about 22 french and 26 french, such as those available from Edwards Scientific Corporation under the tradename "Ascendra"®. Guidewires may also be used in the access protocol, as well as elongate access members configured with what are known as "rapid exchange" features, akin to those described, for example, by Paul Yock and others in disclosures such as U.S. Pat. No. 5,061,273.

FIG. 3C illustrates a close up schematic view of the introducer (44) and left ventricular wall (48) paradigm, with reference to the chest wall boundary (40). With an introducer (44) in place, as depicted in FIGS. 3B and 3C, a diagnostic and/or interventional procedure may be conducted, such as an aortic valve replacement using a prosthesis such as that marketed by Edwards Scientific Corporation under the tradename "Sapien"®. Subsequent to the diagnostic and/or interventional procedure, a closure procedure may be conducted, in accordance with the configurations depicted in FIGS. 3D through 3Z-3. Referring to FIG. 3D, a closure device assembly may be inserted through the introducer. The assembly embodiment depicted in FIG. 3D comprises a plurality of distal struts (54) coupled to a disc or seal member (56), which is coupled to an insertion assembly comprising a thin elongate proximal portion (64) that leads out proximally to a position wherein it may be manipulated by an operator, and a thicker distal portion (66) that is fixedly coupled to the disc member (56). A proximal hub member (60) is slidably coupled about the insertion assembly, and is coupled to a plurality of proximal struts (58). The hub member (60) is removably coupled to a pusher member (68) which leads to a proximal position wherein it may be manipulated by an operator to advance or retract the hub relative to other portions of associated assemblies, such as the insertion assembly (64, 66). Such closure device assembly may be slidably positioned within a working lumen of a delivery sheath (52) when presented to the introducer sheath (44), and the delivery sheath (52) and closure device assembly preferably may be inserted together relative to the introducer sheath (44).

Referring to FIG. 3E, a close up side view of a closure device assembly is depicted, showing the distal struts (54), disc member (56), proximal introducer assembly portion (66), proximal hub (60), and proximal struts (58) in greater detail. In one embodiment, the proximal (58) and distal (54) struts comprise nitinol wire thermally set into the depicted arcuate shapes, the wire having an outer diameter in one embodiment of about 0.023 inches. While the depicted embodiments comprise five distal (54) and five proximal (58) struts, other combinations maybe utilized, such as 1 proximal/1 distal, 2 proximal/2 distal, 3 proximal/3 distal, 4 proximal/4 distal, 6 proximal/6 distal, and so on; further, it is not required that the number of struts proximally match the number distally—thus a 6 proximal/3 distal configuration may be utilized, for example. Preferably the proximal and distal struts are rotatably oriented relative to each other to interdigitate as they are closed, as described below in reference to FIG. 3G, and to provide for anchoring of the sides of the tissue structure around the defect toward each other. Indeed, in some instances, due to the natural dynamics of the tissue comprising the LV apex, a successful closure result may be tied more closely to anchoring the portions of tissue around the defect together (i.e., providing/encouraging tissue apposition) to allow for blood clotting than to total hemostatic sealing.

In one embodiment, the ends of the proximal (58) and distal (54) struts are sharpened to encourage insertion of such ends into tissue that they may be urged toward. The proximal hub (60) and disc member (56) may comprise relatively bioinert materials or composites which have at least some portions having greater stiffness than the materials comprising the struts, to facilitate support of associated structures such as the proximal strut portions. For example, in one embodiment, the proximal hub (60) and disc member (56) comprise titanium metal encapsulated in a relatively inert polymer such as nylon or Delrin®. In another embodiment, the disc member (56) may comprise a compliant solid material, and/or a non-solid construct, such as a structure made from textile-like materials, such as Dacron®, which may be reinforced by an associated external cage or hoop member. An integrated prothrombogenic pad (70), such as one made of gelfoam material, may be coupled to the proximal hub (60) to prevent bleeding around the area of interface between the proximal struts (58) and tissue of the heart wall which may be captured between the proximal (58) and distal (54) struts or adjacent thereto. The outer diameter of the disc member (56) preferably is maximized relative to the delivery sheath (52) and introducer sheath (44) configuration, as the disc member (56) is designed to work as a seal or plug of sorts for the wound left by the transapical access port, in concert with the proximal (58) and distal (54) struts, which are configured to urge nearby tissue against the disc member (56) to close the access port, as described in further detail below. In another embodiment, the disc member may be configured to expand in situ to provide additional wound plugging/sealing geometric advantages in association with captured tissue and sets of struts. Each of the distal struts (54) in the depicted embodiment is bent to contain a captured angle of about 35 degrees when in free space, with a relatively smooth and atraumatic bend distally. The proximal struts (58) project from the proximal hub (60) at a similar angle, but without the reversing bend as in the distal struts (54) in the depicted configuration. Referring to the orthogonal view of FIG. 3F, it may be seen more clearly that the depicted embodiment has five struts proximally and distally. Further, the proximal portion (66) of the insertion assembly has one or more flat surfaces that interface with flats within the proximal hub (60) to maintain a rotational orientation of the proximal hub relative to the distal struts (54) which is selected to allow the proximal struts (58) to interdigitate with the distal struts (54) as the proximal hub (60) is advanced toward the disc member (56), such interdigitation being desirable for grasping tissue without shearing or slicing it. This relative rotational orientation is illustrated in the front view of FIG. 3G. Referring to FIG. 3H, another orthogonal view of the same assembly is depicted to show that two ratchet members (72) are movably coupled to the proximal hub (60) and designed to interface with two sawtooth type ratchet tracks formed into the proximal portion (66) of the insertion assembly. When the proximal hub (60) is being advanced over these ratchet tracks, the ratchet members (72) are configured to allow further insertion, but to prevent retraction (i.e., proximally toward the thoracotomy) of the hub (60). In other words, once the proximal hub (60) has been inserted onto the ratchet tracks of the proximal portion (66) of the insertion assembly, it is locked into a one-way movement paradigm; until it is inserted onto such ratchet tracks, the hub may be retracted and inserted using the proximal hub pusher member (element 68 in FIG. 3D). Referring to FIG. 3I, a closure device assembly is depicted having a different set of proximal struts. The atraumatic proximal struts (59) are configured to not insert into adjacent tissues during deployment, but rather to spread loads relatively atraumatically upon such adjacent tissues with loops that are heat formed into the struts using similar materials and forming techniques as used for the distal struts (54). FIG. 3J shows a front view to illustrate the relative rotational orientation of the proximal and distal struts (59, 54) that is enforced with flats or other similar rotational orientation enforcing features at the interface between the proximal hub (60) and proximal portion (66) of the insertion assembly. Referring to FIGS. 3J-i and 3J-ii, a frustoconical fabric member (232), comprising one or more layers of a material such as Dacron® fabric, may be coupled to the distal aspect of the proximal struts (59—or 58 in other embodiments) to de-concentrate, or spread, loads that may be applied to nearby cardiac tissues through such struts, due to the fact that such material has higher structural material compliance than the materials preferred for the struts, and is presented to the tissue with a larger surface area, as in the depicted embodiment. The fabric may also help to control and/or mitigate minor bleeding which may be present at the nearby tissue structure surface.

Referring to FIG. 3K, picking up again from where FIG. 3D left off in the depicted deployment process, the closure device assembly and associated delivery sheath (52) has been further inserted into the patient. Referring to FIG. 3L, when the operator desires to begin installation of the closure assembly, the insertion assembly (64, 66) may be advanced relative to the delivery sheath (52) and introducer (44) to a point wherein the distal struts (54) are able to bend past the distal ends of the delivery sheath and introducer sheath (78, 76) and assume their heat shaped configurations (i.e., without the delivery sheath or introducer sheaths inner lumen walls constraining them into a more compressed configuration, as they may be during insertion). Generally the distal struts (54) are configured to expand past the outer diameter of the introducer sheath (44) to be able to capture and anchor to the nearby tissue. In one embodiment, the distal struts are configured to expand by about 20% in diameter (i.e., from a contained diameter of about 26 french to an uncontained diameter of about 31 french) when allowed out of the constraints of the delivery and introducer sheaths, and this expansion assists with capturing portions of a ring of tissue about the surgically-created transapical defect that may be pulled in toward the disc member (56) to create a wound plugging or closing effect. This radial expansion (74) of the distal struts is illustrated in FIG. 3L. Referring to FIG. 3M, with the distal struts (54) expanded to their heat-formed configurations, to assist in providing enough tissue purchase by the distal struts (54), the introducer sheath (44) and delivery sheath (52) may be withdrawn, thereby allowing nearby tissue to migrate inward (80) toward the disc member (56). This withdrawal may be simultaneous or sequential (FIGS. 3M and 3N depict a partial sequential withdrawal—first of the introducer sheath 44, then of the delivery sheath 52; FIG. 3O depicts a simultaneous withdrawal of both sheaths 44 and 52 together, to allow further inward migration 80 of the viscoelastic tissue that forms the left ventricular wall 48). The proximally pointed distal tips of the distal struts (54), along with the arcuate, curved nature of the distal struts (54) and proximal advancement of them into the tissue as in FIGS. 3N-3P with purchase of the tissue as the introducer retraction is begun provides an important anchoring and grasping of the tissue toward other tissue, which also closes the wound around the proximal aspects of the device. In other words, the deployment bunches nearby tissue toward itself, providing for a heart cavity exposure that consists mostly of live tissue anchored about a plurality of relatively small distal struts (54). This minimal hardware exposure is preferred for biological tissue coverage (i.e., endotheliziation) advantages, and avoids discontinuities and/ or necrosis in the critical endocardial tissue surface that may result from prostheses with larger endocardial device exposure. Referring to FIG. 3P, the insertion assembly (64, 66) may then be pulled toward the operator to assist with seating the distal struts (54) into the captured tissue if they have not already seated themselves (i.e., given the sharpened tips and springlike nitinol material of the abovedescribed variations), at which point a sealing of the transapical access wound may be formed given the interaction of the distal struts (54) and disc member (60), which effectively capture and bunch inwardly a portion of tissue surrounding the left ventricular cavity side of the transapical access wound. Referring to FIG. 3Q, the introducer sheath (44) and delivery sheath (52) may be further withdrawn to allow further migration (80) of the viscoelastic tissue comprising the transapical access wound. Referring to FIG. 3R, the proximal hub (60) and associated proximal struts (58, or in the case of an embodiment such as that depicted in FIGS. 3I and 3J, element 59) may be advanced toward the disc member (56) using the proximal hub pusher member (68); in the embodiment depicted in FIG. 3Q, the introducer sheath has been completely removed; in other embodiments, it may remain and be moved in parallel with the delivery sheath (52). Referring to FIG. 3S, the proximal hub (60) may be further advanced (88) and/or or the delivery sheath retracted (90) to allow the proximal struts (58) to become free and bend past the distal end of the delivery sheath, and be inserted toward the disc member (56) to capture proximal portions of tissue comprising the transapical access wound and urge them toward the disc member (56), as shown in FIG. 3T. At such level of proximal hub (60) insertion, the proximal hub (60) has entered the ratchet tracks formed into the proximal portion (66) of the insertion assembly, and one way locking action of the hub (60) is enforced to facilitate secure positioning and maintenance of the closure assembly. At this point the transapical access wound is effectively closed, with proximal (58) and distal (54) struts urging tissue portions toward the disc member (60) to create a sealed wound that will become further biologically integrated over time.

Figure 1:
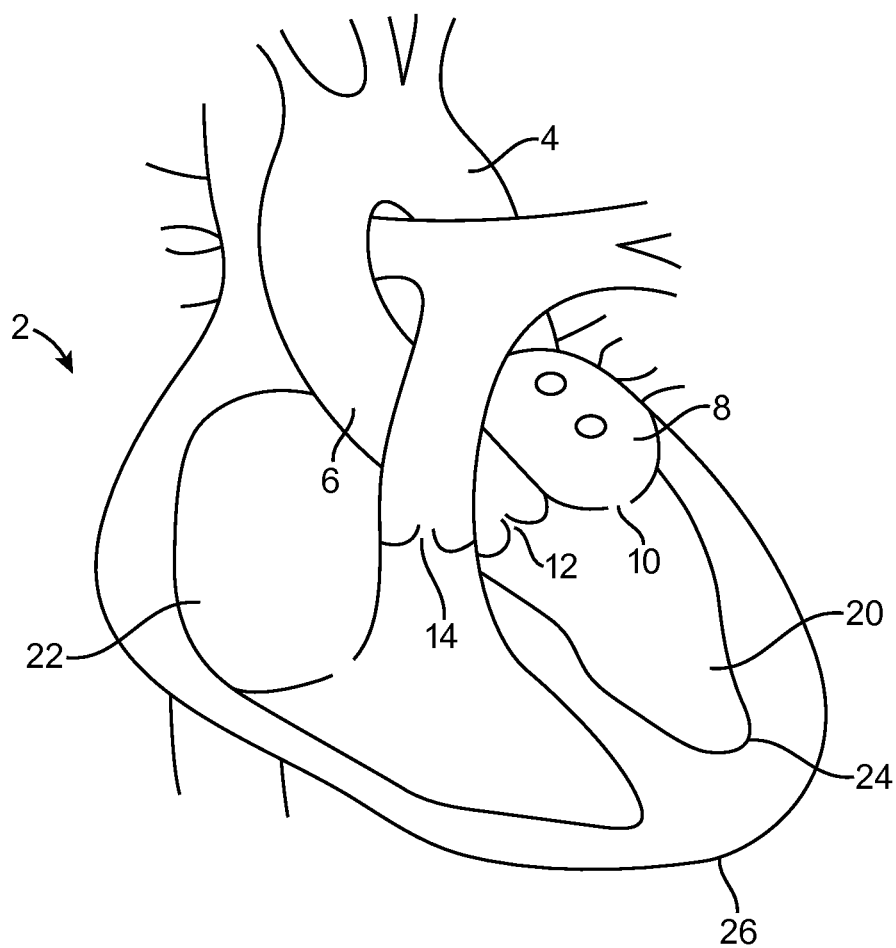
FIG. 1 illustrates aspects of the human heart anatomy.
Figure 2:
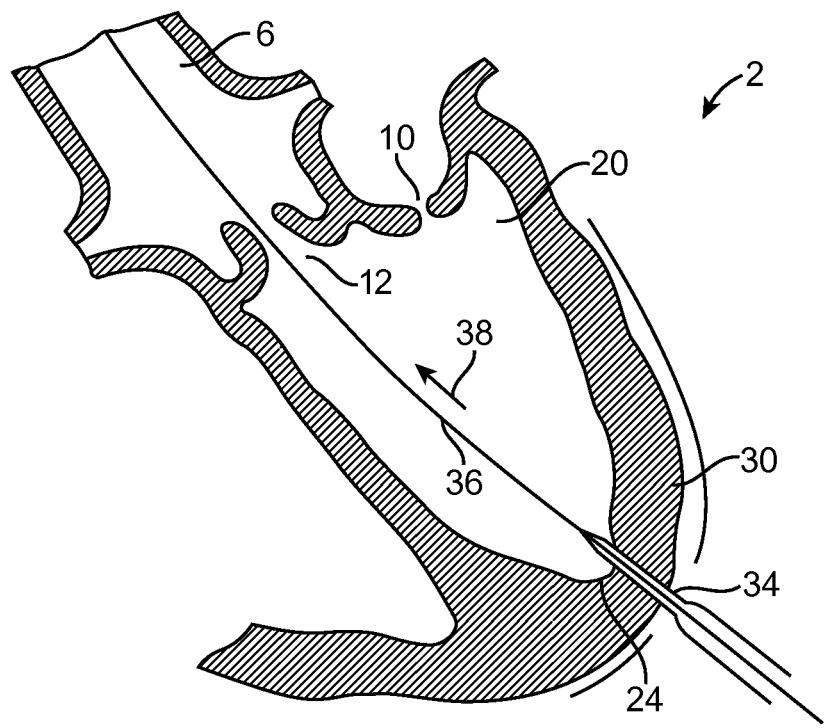
FIG. 2 illustrates a conventional transapical access procedure.

Referring to FIG. 3U, the proximal hub pusher member (68) may be decoupled from the proximal hub (using, for example, a threaded interface that may be controllably detached using rotation of the pusher member 68) and withdrawn (92) proximally. Referring to FIG. 3V, an optional prothrombogenic pad (96), such as one made of gelfoam material, may be installed over the deployed closure device proximal aspects using a pad inserter member (94) defining a lumen (100) through which portions of the insertion assembly (64, 66) may be passed. The pad inserter member (94) may have a frustoconical distal portion (98) configured to broadly interface the prothrombogenic pad against the targeted closure device and tissue structures, as shown in FIG. 3X, after further advancement (102) of the pad inserter member (94) and/or retraction (90) of the deployment sheath (52). With the prothrombogenic pad (96) in place, the pad inserter member (94) may be retracted (104) as shown in FIG. 3Y, and a cutter assembly, comprising, for example, a cutter (106) and two cutter actuation members (108, 110), may be advanced toward the deployed closure device, as shown in FIGS. 3Z and 3Z-1. In the depicted embodiment, the two cutter actuation members (108, 110) are configured to cause the cutter (106) to shear off any elongate members passed through it, such as any portions of the insertion assembly proximal portion (64) or distal portion (66) which may be passed therethrough. Referring to FIG. 3Z-2, the insertion assembly proximal portion (64) has been intentionally cut close to the deployed prothrombogenic pad (96), leaving behind a minimal amount of hardware protruding proximally from the closed transapical access wound when the remaining uncoupled installation hardware is withdrawn (114). The resultant deployed closure assembly (116) is depicted in FIG. 3Z-3.

Figure 4:
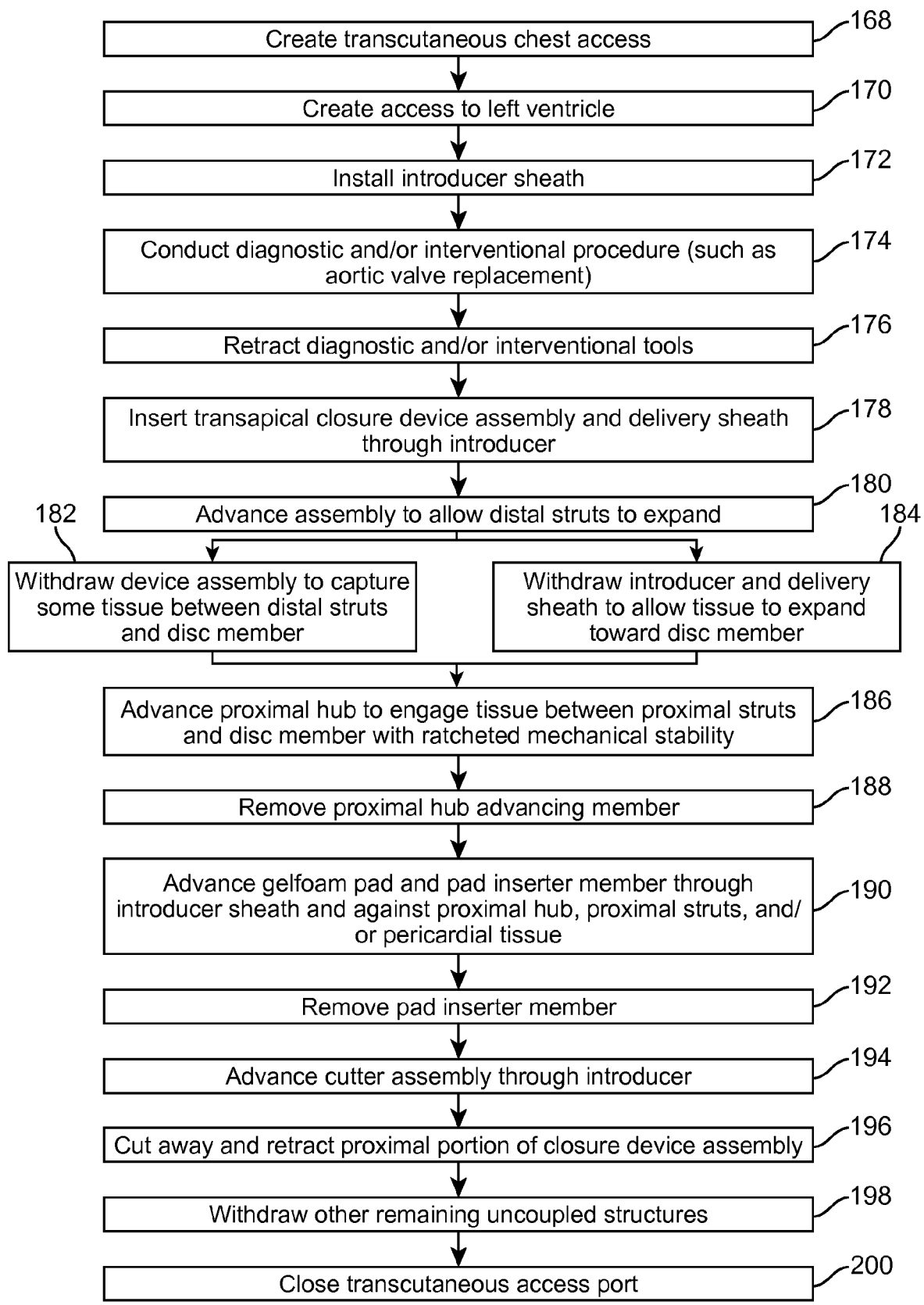
FIG. 4 illustrates various aspects of a method for creating transapical access for a diagnostic and/or interventional procedure, and closing following such procedure, in accordance with aspects of the apparatus embodiments illustrated in FIGS. 3A to 3Z-3.

Referring to FIG. 4, a method of deploying a wound closure device, using techniques such as those described in reference to FIGS. 3A through 3Z-3 is illustrated. After transcutaneous chest access is created (for example, by a thoracotomy) (168), access may be surgically created to reach the left ventricle (170) and an introducer sheath installed (172). The introducer sheath may be utilized to conduct a diagnostic and/or interventional procedure, such as a aortic valve replacement (174), subsequent to which the related diagnostic and/or interventional tools may be withdrawn (176) and closure begun. In the depicted embodiment, a transapical wound closure device assembly (comprising structures such as elements 54, 56, 66, 58, 60, 64, 68 of FIG. 3D, for example) positioned within a delivery sheath (52) may be introduced through the introducer sheath (178) and advanced to allow distal struts to expand past the distal portions of the introducer sheath and delivery sheath (180). The introducer and delivery sheathes may be withdrawn (184) in parallel, or in advance, or withdrawal of the device assembly (182) to capture some tissue between the distal struts (54) and the disc member (56). The proximal hub (60) may be advanced (186) to engage tissue between the proximal struts (58) and the disc member (56) with ratcheted mechanical stability provided by the interfacing features of the proximal hub (60) and distal portion (66) of the insertion assembly. With the proximal hub (60) in position causing the proximal struts to urge the proximal aspect of the wound toward the disc member (56) and cause additional sealing of the wound, the proximal hub advancing member (i.e., the pusher member 68) may be removed (188) and a prothrombogenic pad (96) may be advanced through the introducer sheath and/or delivery sheath using a pad inserter member (94), and against the tissue and device structures that are proximally available to the pad (190). The pad inserter member (94) may be removed (192), and a cutter assembly advanced through the introducer and/or deployment sheath (194). The cutter may be utilized to cut away (196) proximal portions of the insertion assembly, and the uncoupled portions may be withdrawn proximally (198), after which the transcutaneous access port may be closed (200).

Figure 5A:
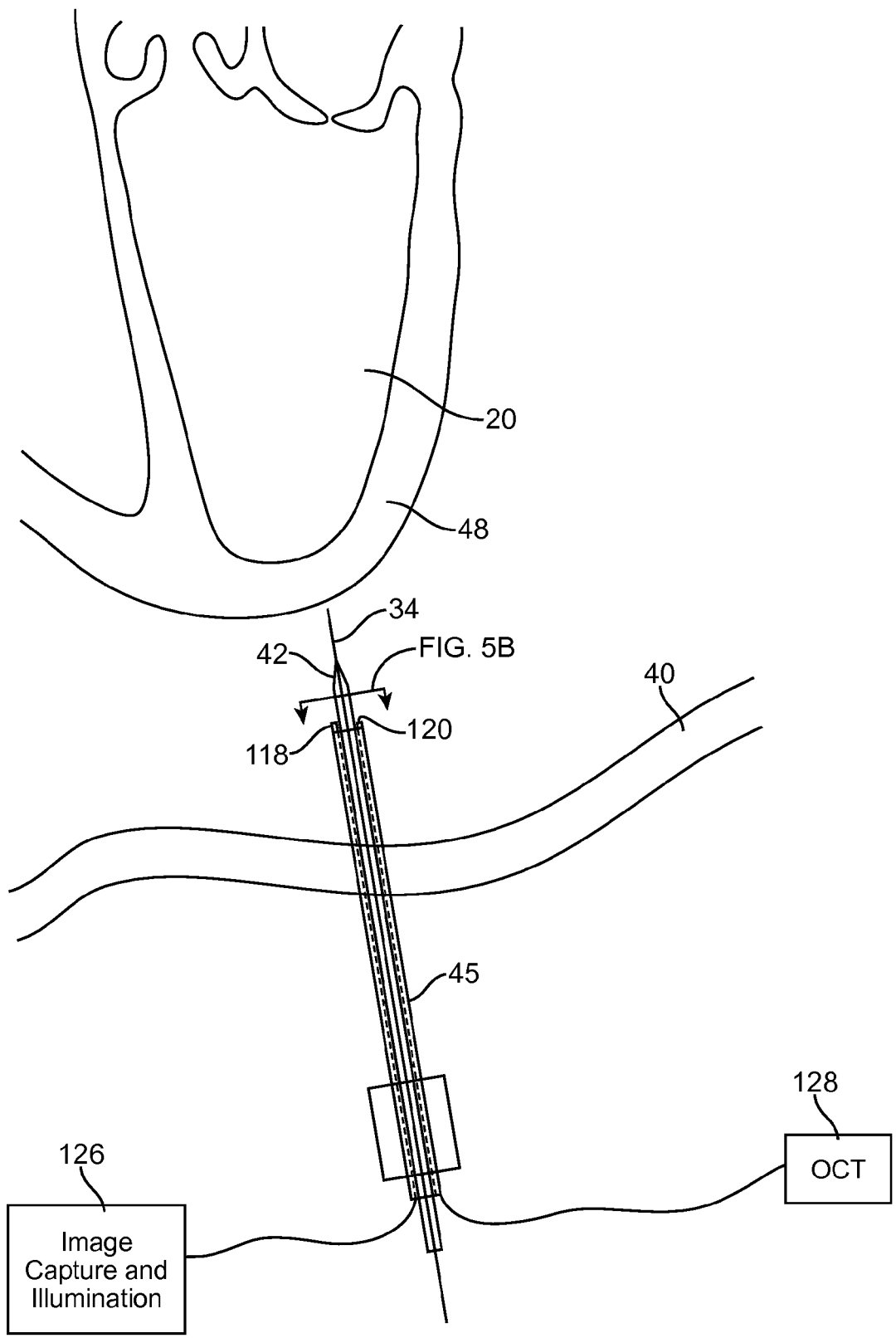
FIGS. 5A-5B illustrate an embodiment wherein imaging and measurement tools may be utilized to assist with the accurate orientation and placement of a transapical access port.
Figure 5B:
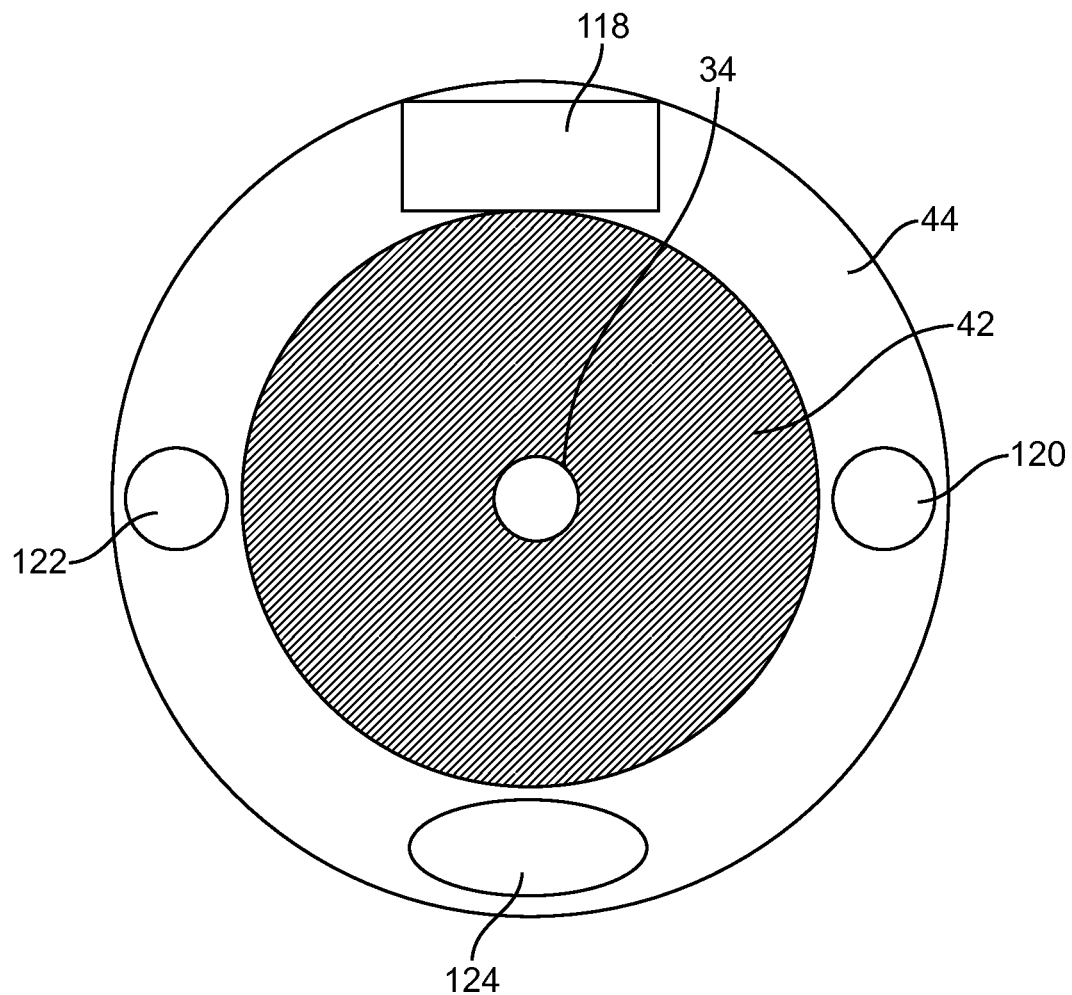
Figure 6:
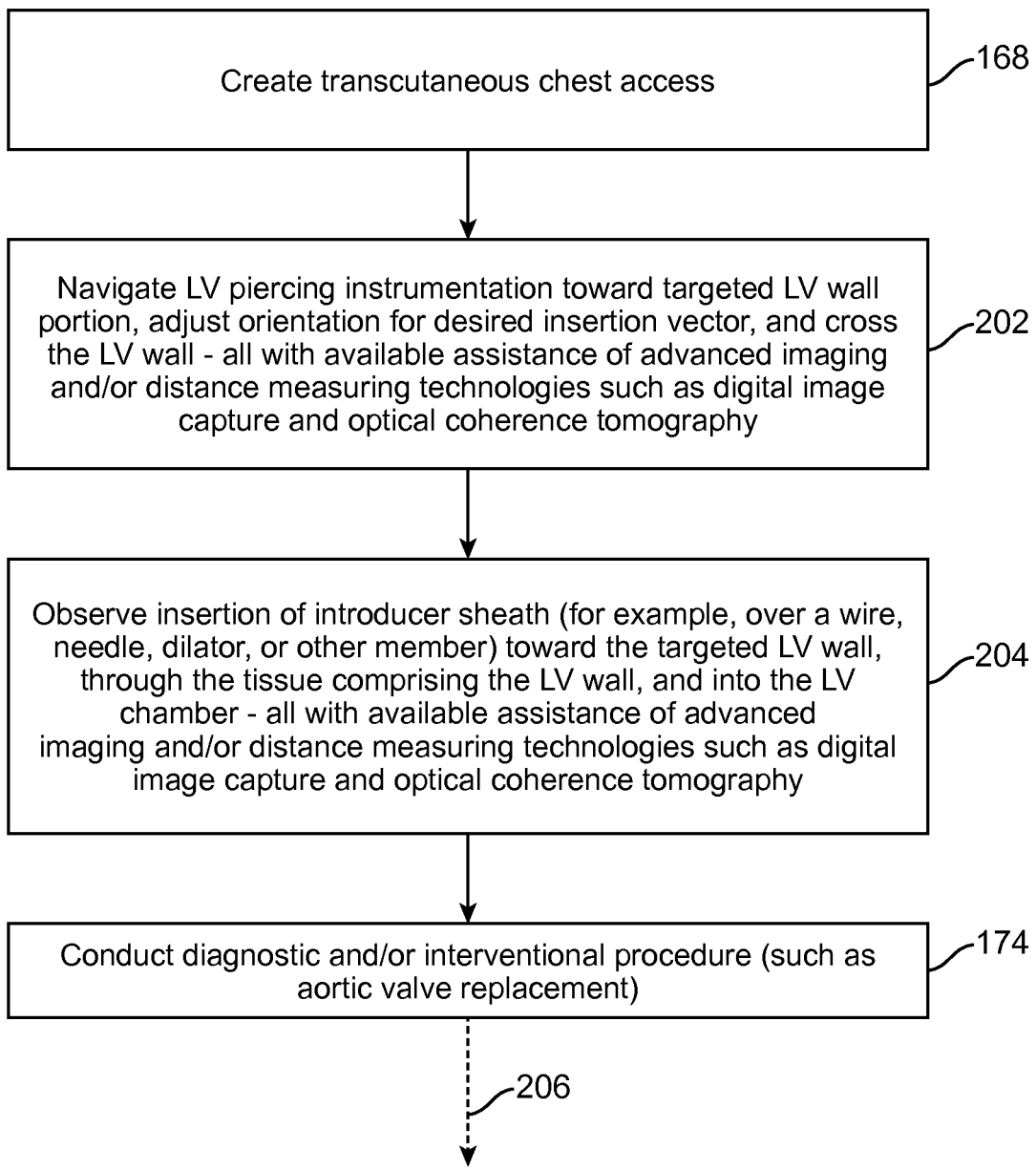
FIG. 6 illustrates various aspects of a method for creating transapical access for a diagnostic and/or interventional procedure, and closing following such procedure, in accordance with aspects of the apparatus embodiments illustrated in FIGS. 5A and 5B.

Referring to FIG. 5A, a configuration similar to that described in reference to FIG. 3A is depicted, with the exception that the introducer sheath (44) in the embodiment of FIG. 5A is instrumented with additional technologies, such as an image capture device (118) and optical coherence tomography ("OCT") device (120) to facilitate introducer placement across a critical tissue structure, such as the left ventricular wall (48). As shown in the cross sectional view of FIG. 5B, the image capture device preferably comprises an optical fiber bundle or a digital imaging chip, such as a CMOS, CCD, or other high resolution image capture device similar to those utilized in socalled "chip on the tip" laproscopy, which is coupled to an image processing and/or capture system (element 126 referring back to FIG. 5A) by an electric lead in the lead bundle that couples the device (118) and the system (126). The system may also comprise an illumination source which may pass light radiation to the operational theater in situ using a fiber bundle (122) which may also comprise part of the lead bundle leading back to the system (126). An irrigation port (124) may also be present to allow for controllable irrigation, vacuum, and/or medicine, contrast agent, or other solution delivery to the operational theater in situ. As shown in FIG. 5B, the OCT device (120) may comprise a fiber or fiber bundle on the introducer side that leads proximally back to an interferometry system (128) capable of generating images as well as distance information, such as the thickness of the left ventricular wall (48) straight ahead in situ, for the operator. A combination of intraoperative direct visualization using image capture, irrigation, and or illumination, as well as intraoperative three dimensional image and measurement feedback from a system such as OCT, is selected to provide an operator with valuable and fresh information as he selects an insertion vector position for the pertinent instrumentation. Referring to FIG. 6, a method is depicted wherein after creating transcutaneous access (168), as in FIG. 4, a left ventricular access device configuration may be navigated, positioned, and oriented using fresh information from forward oriented direct visualization and imaging and/or measurement features of onboard OCT technology (202). These same imaging and information technologies may be utilized during insertion of the device components to confirm positioning and continue to provide fresh information for the operator (204). Subsequently, the diagnostic and/or interventional steps (174), as well as other steps (206), may be conducted as described above.

Figure 7A:
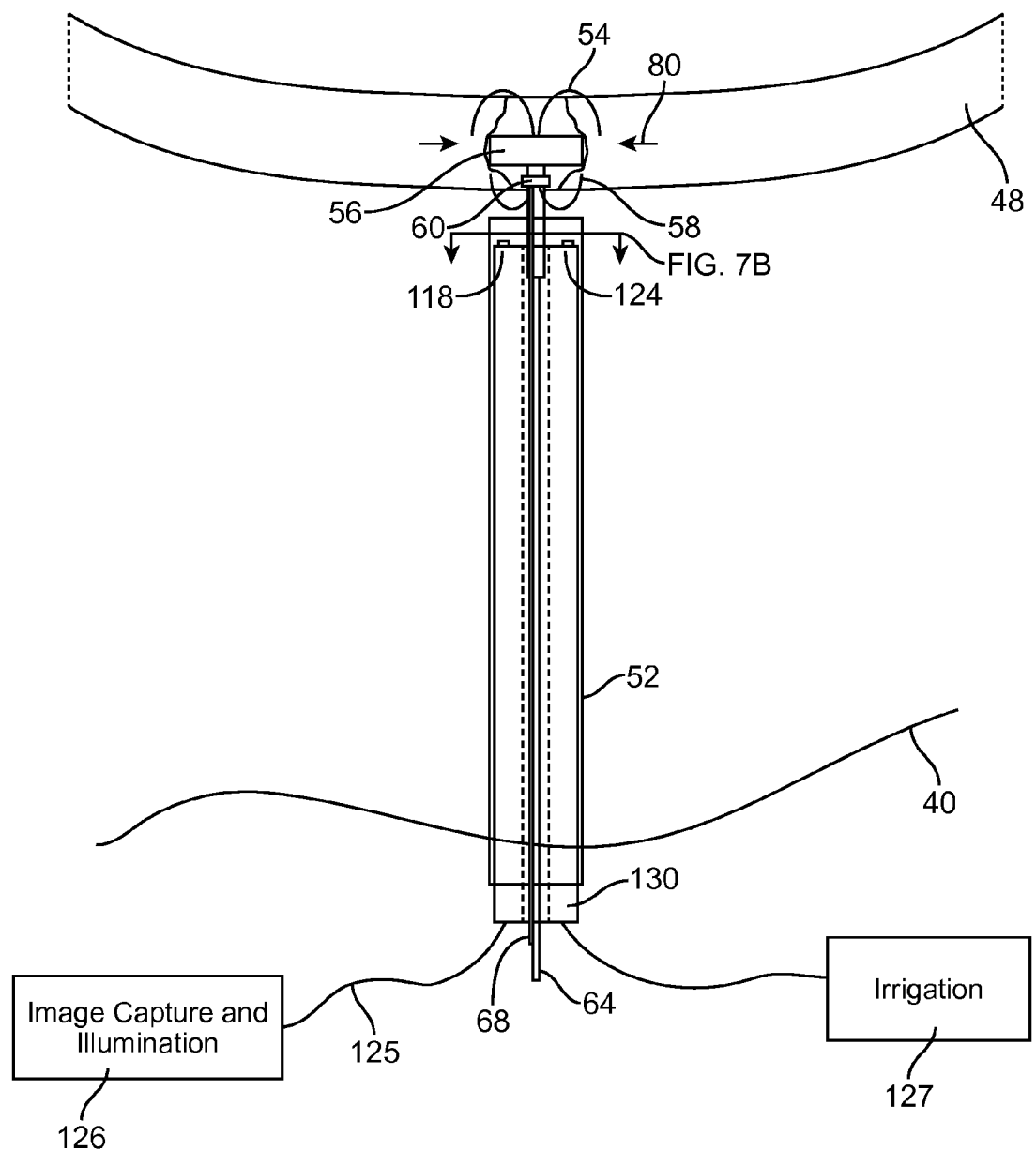
FIGS. 7A-7B illustrate an embodiment wherein imaging and measurement tools may be utilized to assist with the accurate positioning and deployment of a transapical access port closure device.
Figure 7B:
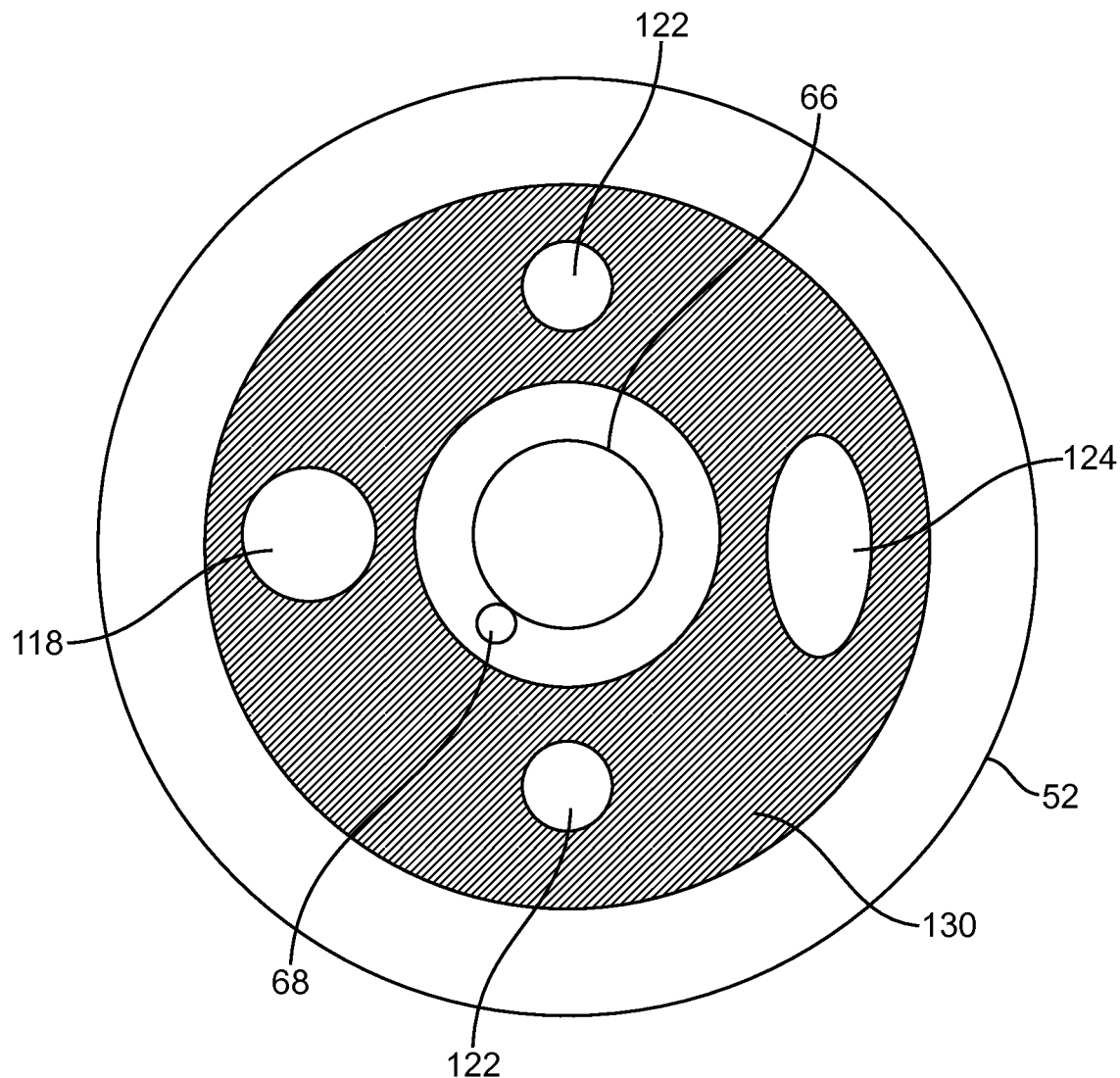
Figure 8:
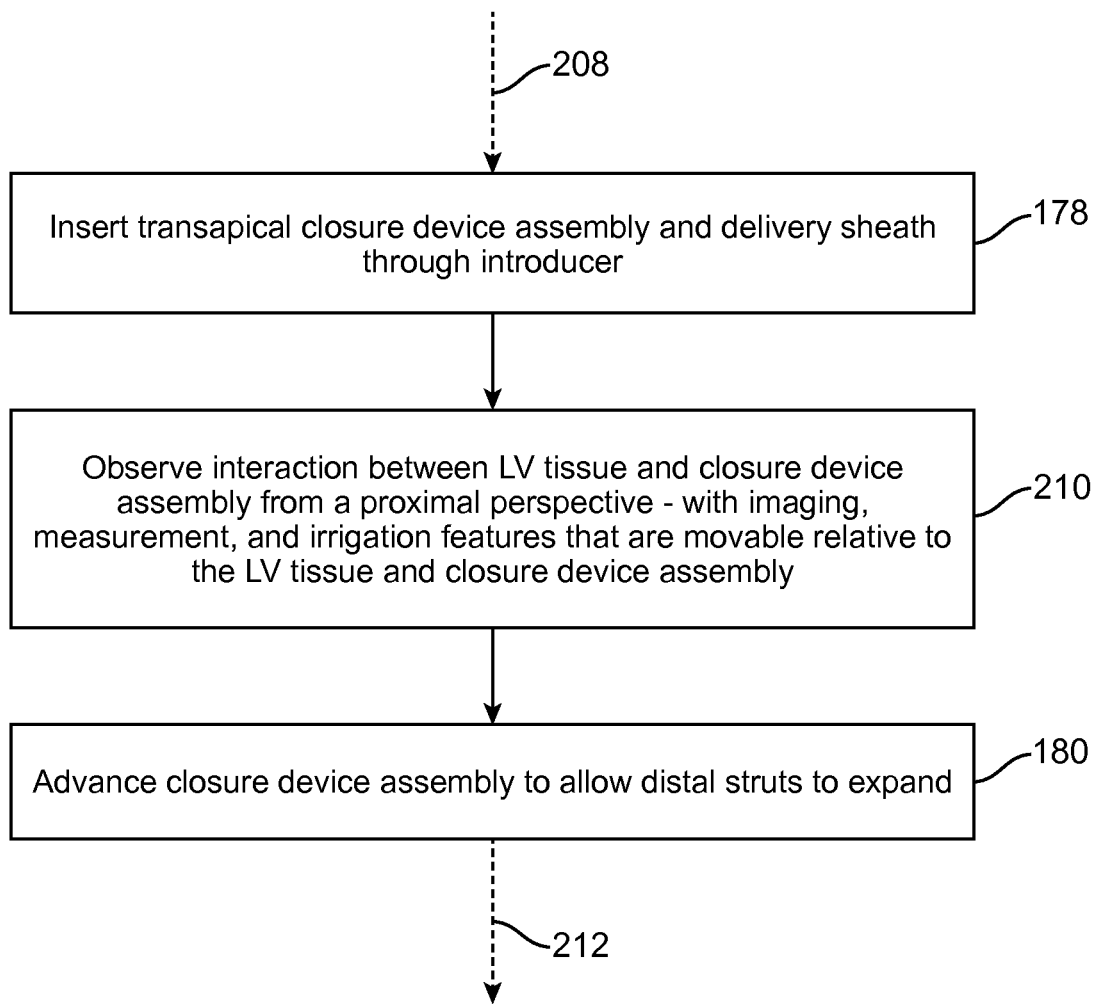
FIG. 8 illustrates various aspects of a method for creating transapical access for a diagnostic and/or interventional procedure, and closing following such procedure, in accordance with aspects of the apparatus embodiments illustrated in FIGS. 7A and 7B.

Referring to FIG. 7A, an embodiment similar to that described in reference to FIG. 3T is depicted, with the exception that an elongate imaging platform (130) has been inserted through the deployment sheath (52) and over the insertion assembly (64, 66) and pusher member (68) using a lumen defined through the elongate imaging platform (130). An image capture device (118) and irrigation port (124) are located distally and coupled through the elongate imaging platform (130) to an image capture and illumination system (126) and an irrigation system (127). Referring to FIG. 7B, a cross sectional view is depicted to show the various distal components. In the depicted embodiment, the elongate imaging platform may be rotated relative to the closure device components and left ventricular tissue—to enable the various irrigation, image capture, illumination, and other components access more of the pertinent forward oriented activity. On board OCT (not shown) may also be included in the form of an additional fiber or fiber bundle through the elongate imaging platform that is proximally interfaced with an OCT interferometry system configured to provide images and measurements. Referring to FIG. 8, aspects of a method are depicted wherein subsequent to other procedural steps (208), such as those described above in reference to FIG. 4, for example, a transapical closure device may be inserted (178), and the interaction (210) between left ventricular tissue and closure device assembly portions observed and characterized with imaging, measurement, and irrigation features that are movable relative to the tissue and closure device. In one embodiment, for example, an image capture device and irrigation port may be utilized to check for leaks around each portion of the circumference of the proximal aspect of the device-closed wound. Further, sealants, medicines, and other solutions may be applied with direct visualization. Subsequently, other steps of diagnostic and/or interventional procedures, such as those described above, may be conducted (212).

Figure 9A:
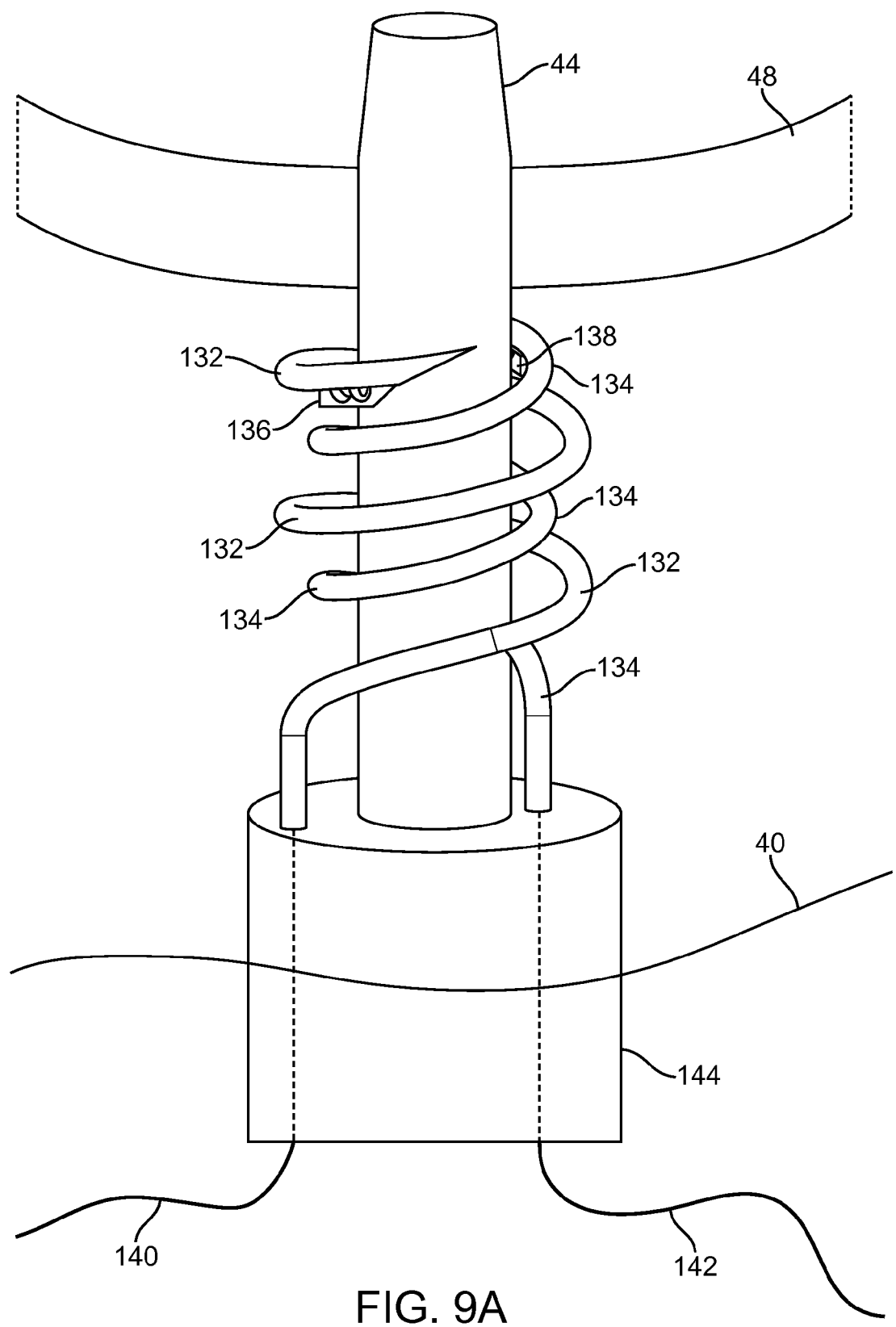
FIGS. 9A-9G illustrate various aspects of embodiments of a system for creating transapical access for a diagnostic and/or interventional procedure, and closing following such procedure using one or more helical needles for suture deployment.
Figure 9B:
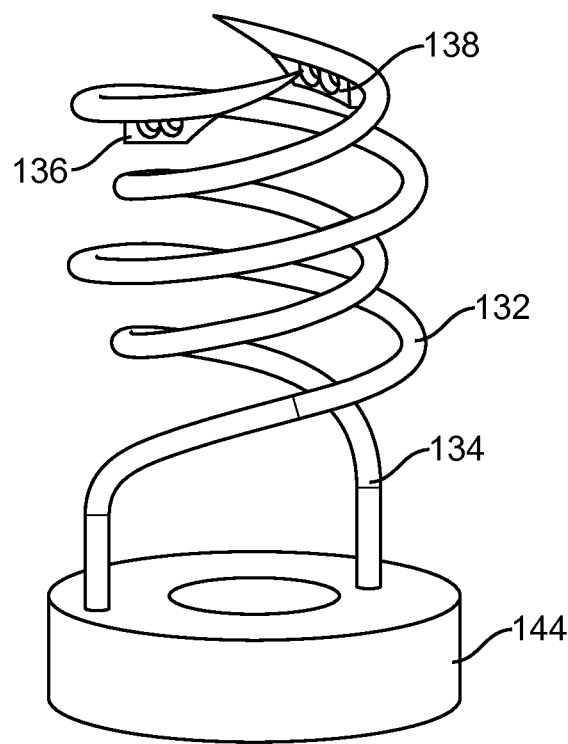
Figure 9C:
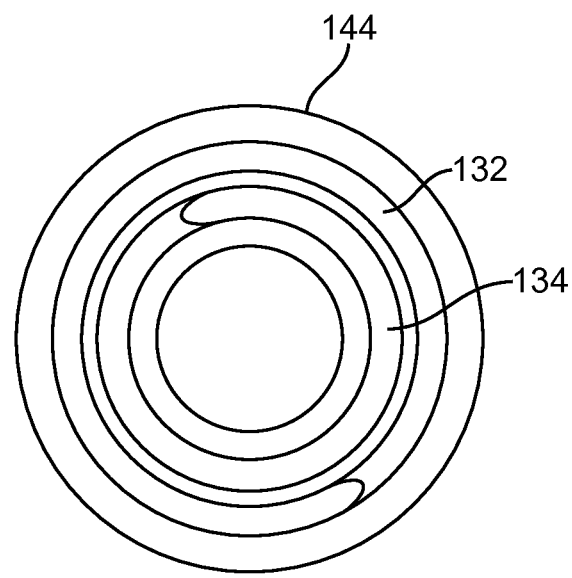
Figure 9D:
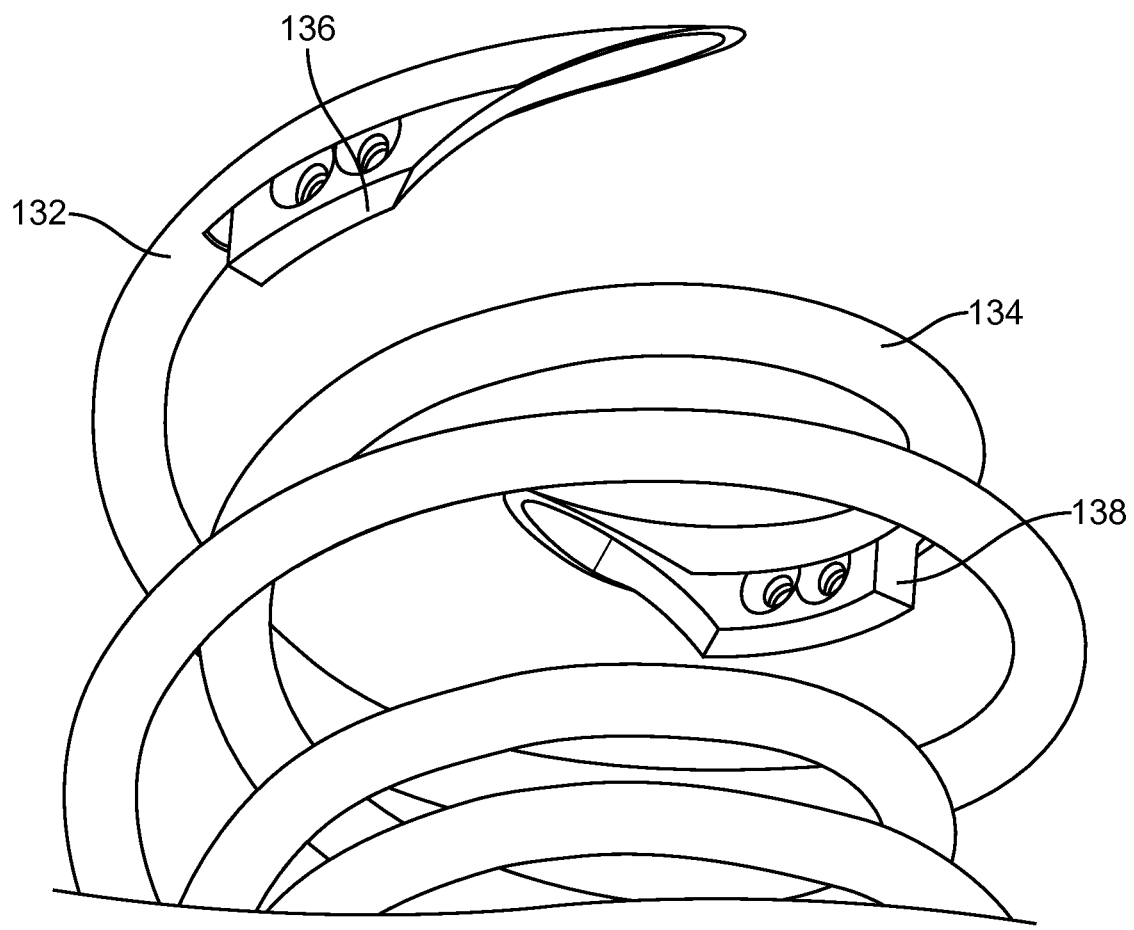
Figure 9E:
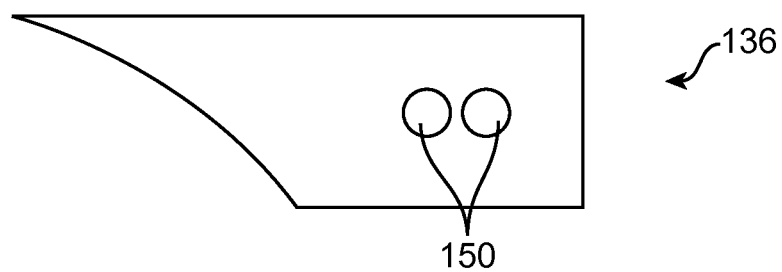
Figure 9F:
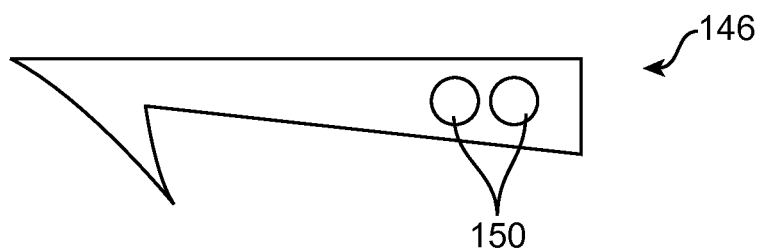
Figure 9G:
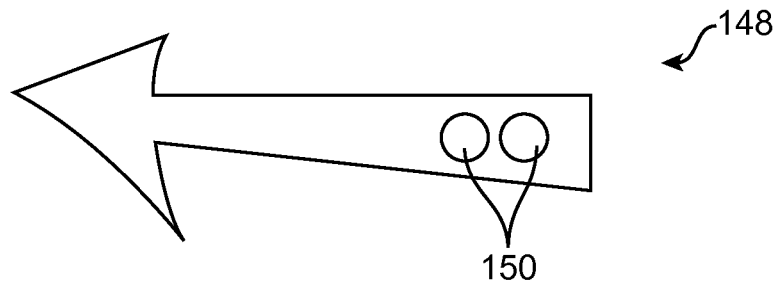

FIGS. 9A-12 depict aspects of other embodiments for closing wounds created across tissue structures such as the wall of the left ventricle, using helically advanced sutures. Referring to FIG. 9A, in introducer sheath (44) has been advanced into the left ventricle using techniques such as those described above. Subsequent to conducting pertinent diagnostic and/or interventional procedures using the introducer, a helical suture closure device may be utilized to assist with closure of the transapical access wound. As shown in FIG. 9A, a helical suturing assembly embodiment comprises a needle insertion member (144) fixedly coupled to two helical needles (132, 134). In the depicted embodiment, a first helical needle (132) has a helical radius that is larger than the helical radius of the second helical needle (134). Each of the helical needles preferably comprises a relatively stiff and hollow construct, made from a material such as stainless steel. Threaded through the first helical needle (132) is a first suture (140) which is coupled distally to a first distal anchor member (136). Similarly, threaded through the second helical needle (134) is a second suture (142) which is coupled distally to a second distal anchor member (138). The ends of the needles (132, 134) preferably are sharpened to facilitate access into pertinent tissue structures. FIGS. 9B and 9C depict additional orthogonal views of the helical needles and a distal portion of the needle insertion member (144). FIG. 9D depicts a close up orthogonal view of the previously depicted first and second helical needles (132, 134) and distal anchor members (136, 138). The anchor members preferably are geometrically configured to slidably and removably engage the distal ends of the pertinent helical needles, and to fasten or hook onto tissue and slidably disengage from the needle distal ends when the helical needles are rotated counterclockwise in the depicted example embodiment. In other words, with such embodiment, as the helical needles are advanced the needle insertion member (144) is rotated clockwise, the anchors are configured to stay in place at the distal ends of the needles; once the needle insertion member rotation is reversed to counterclockwise, small features on the anchor members (136, 138) are configured to catch upon the nearby tissue, pull the anchors out of their positions transiently housed in the needle tips, and begin to pull suture through the hollow needles, leaving helical suture paths with distal anchors, as shown, for example, in FIGS. 10A-10B, and 11A-11B. Referring to FIGS. 9E-9G, various anchor configurations (136, 146, 148) are shown, each of which has one or more features (150) configured for fastening a suture or other tensile member, and each of which has geometric features configured to catch upon nearby tissue structures when moved backward relative to such tissue structures. Referring to FIGS. 10A-10B, an embodiment is depicted wherein the anchors have been helically driven across the thickness of the left ventricular wall (48) such that they are located within the left ventricular chamber. Referring to FIG. 10B, they may be tensioned concomitant to withdrawal of the introducer to close the transapical access wound. In one embodiment, the two sutures (140, 142) may be tensioned simultaneously. In another embodiment, they may be tensioned sequentially. In yet another embodiment, combinations of parallel and sequential tightening may be utilized. For example, in one embodiment, initially both may be tightened in parallel to a first tension level using manual manipulation from the operator (i.e., using graspers or other instruments placed through the chest wall, or by pulling the suture ends up across the thoracotomy where they may be manipulated outside of the body), after which a second higher tension level may be achieve in the first suture with the larger helical diameter, followed by final "fine tuning" tension to take the second suture with the smaller helical diameter to a higher tension level that may be equivalent to the second tension level of the first suture. Such an approach is believed to assist with complete closure of wounds wherein the inner (i.e., near the smaller helical diameter suture) portions of the tissue may have been plastically deformed to a greater degree than the outer portions (i.e., near the larger helical diameter suture) due to the process of blunt surgical access tool insertion. FIGS. 11A-11B depict a tightening scenario similar to that of FIGS. 10A-10B, with the exception that the helical needles (132, 134) and anchor members (136, 138) are only advanced to the midportion of the thickness of the tissue structure wall (i.e., not all the way across, as in the embodiment of FIGS. 10A-10B).

Figure 12:
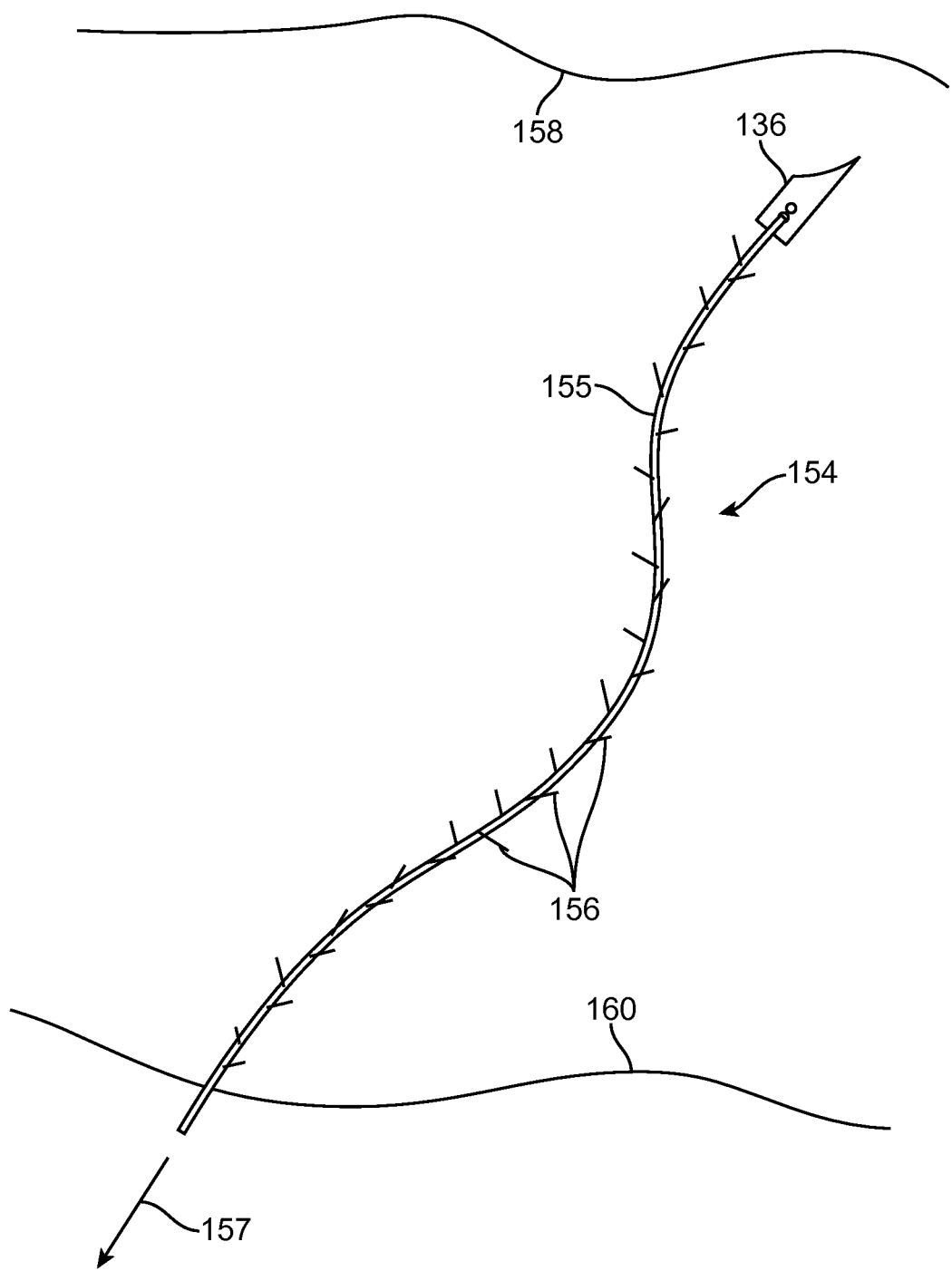
FIG. 12 illustrates one embodiment of a barbed suture and anchor assembly.

In one embodiment the sutures may be comprise barbed suture material, such as those available from Angiotech Corporation under the tradename "Quill"®. Referring to FIG. 12, in another embodiment, relatively high-load barbed suture (154) may be formed using a braided suture body material (154), such as a Dacron® braid, into which small barbs (156) have been placed, which enough length inserted into the suture body material to prevent the barbs (156) from becoming substantially repositioned, and enough load bearing capability in each of the barbs to provide a net tensile load resistance that is relatively significant when applied to an anchored suture placed at least in part between the two margins (158, 160) of a tissue structure.

Figure 10A:
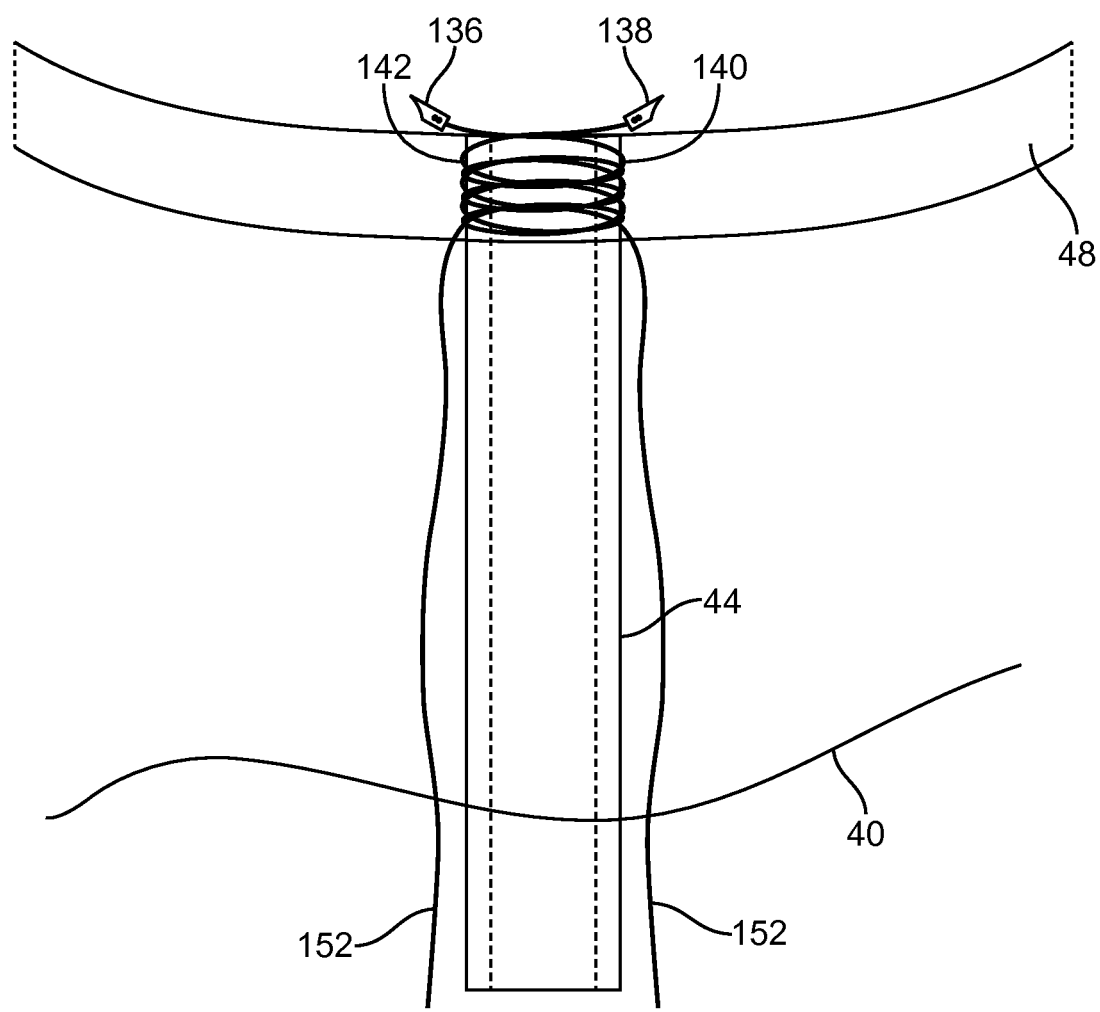
FIGS. 10A-10B illustrate various aspects of a suture and anchor deployment embodiment wherein the anchors are placed across the thickness of the subject tissue structure, such as in the left ventricular cavity.
Figure 10B:
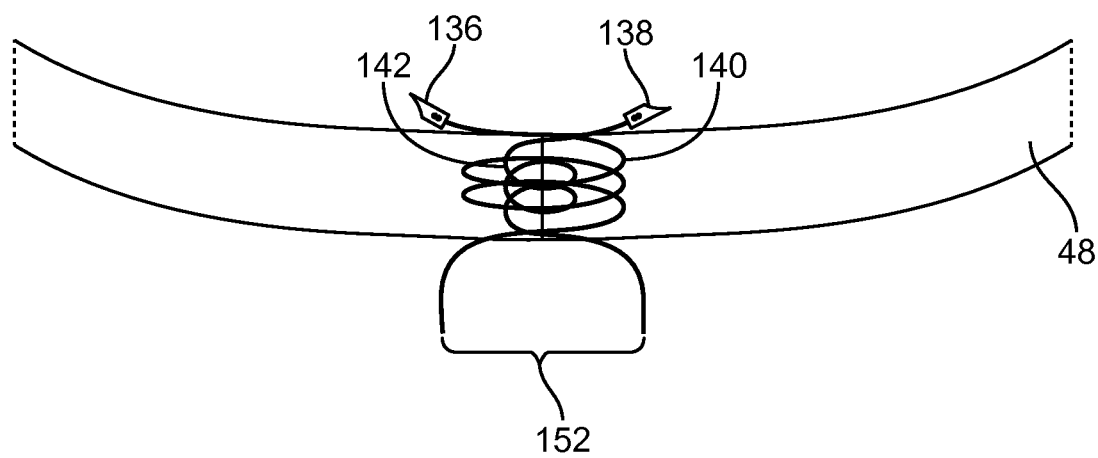
Figure 10B:
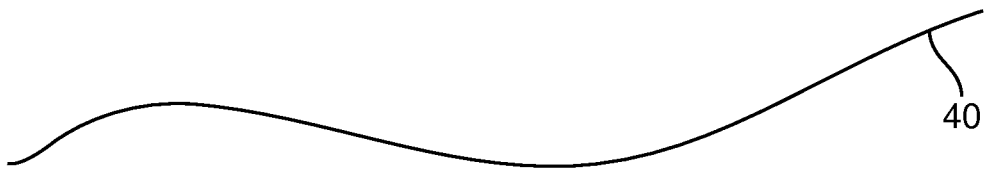
Figure 11A:
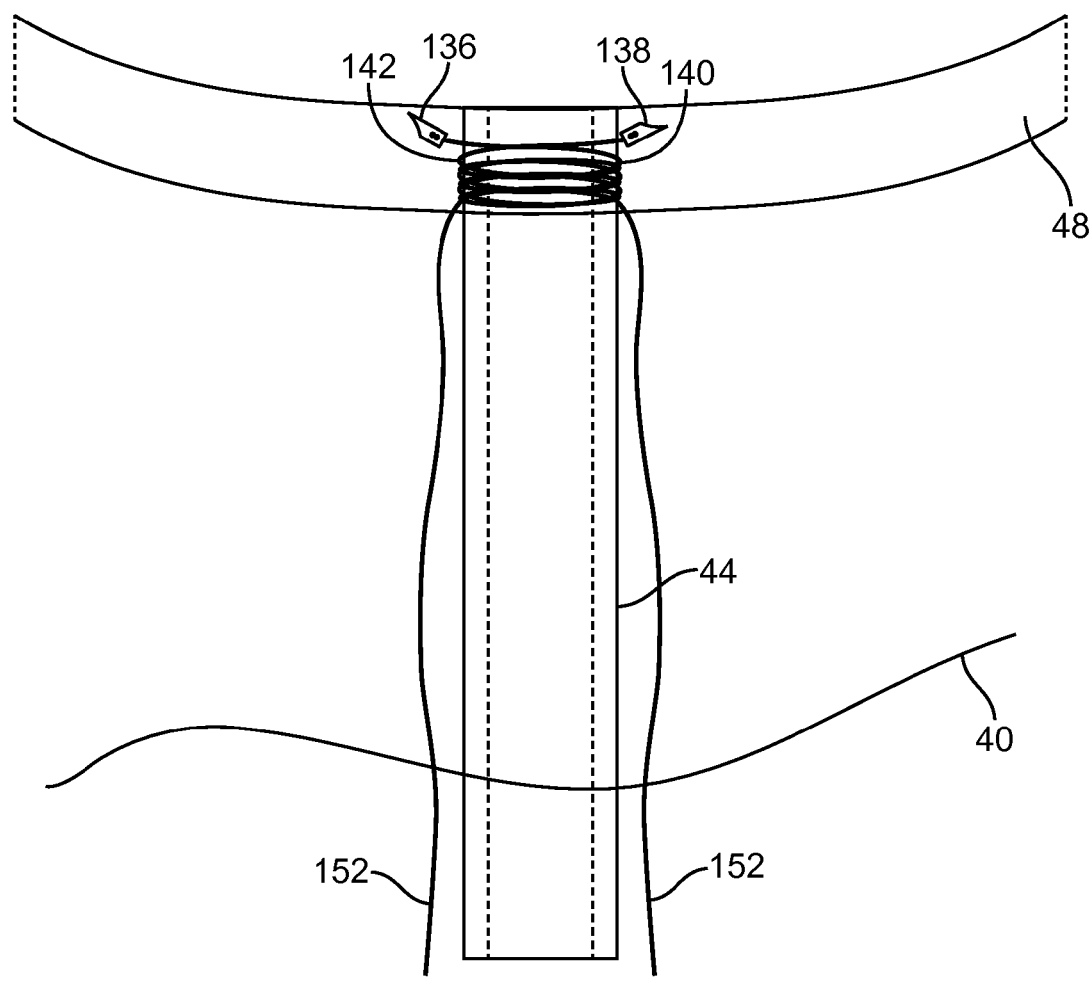
FIGS. 11A-11B illustrate various aspects of a suture and anchor deployment embodiment wherein the anchors are placed within the thickness of the subject tissue structure, such as in the muscular walls of the left ventricle.
Figure 11B:
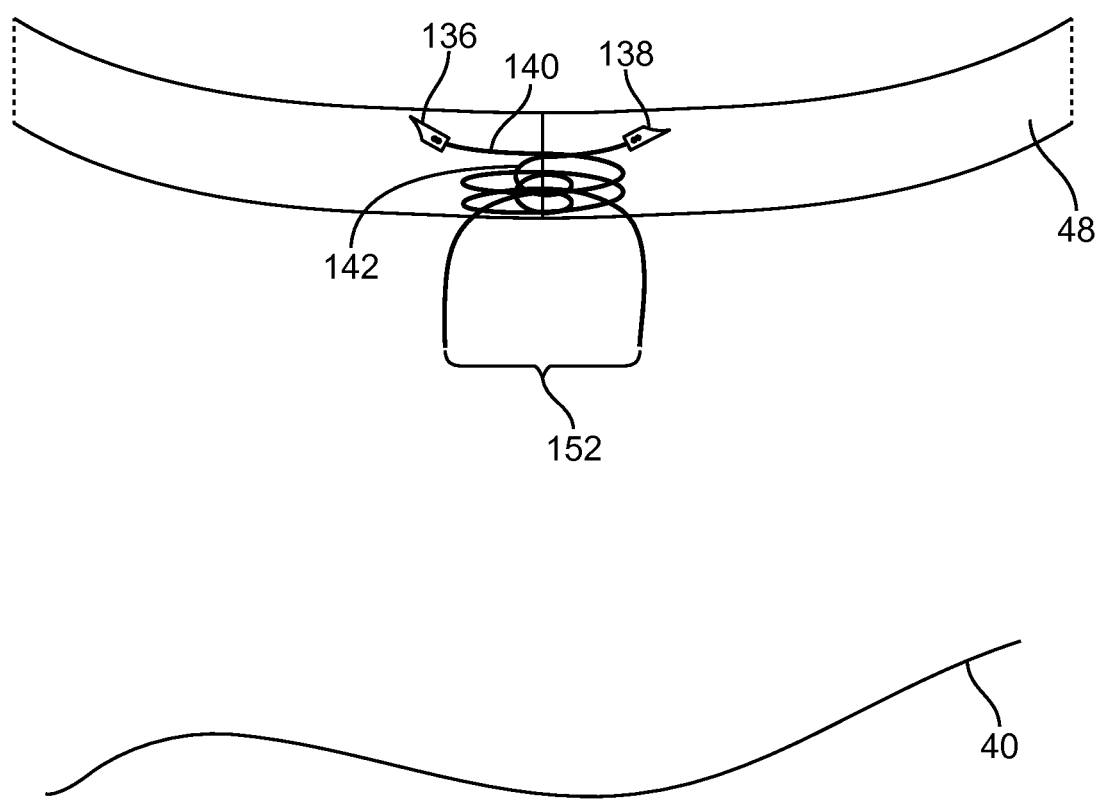

The suture proximal ends (152) depicted in FIGS. 10B and 11B may be tied to each other to maintain tension on the sutures, or may be placed into permanent or semipermanent levels of tension utilizing small buckles or suture tensioners, in addition to conventional pledgets and surgical knots which may be used for each suture, or the two or more sutures as tied together.

Figure 13A:
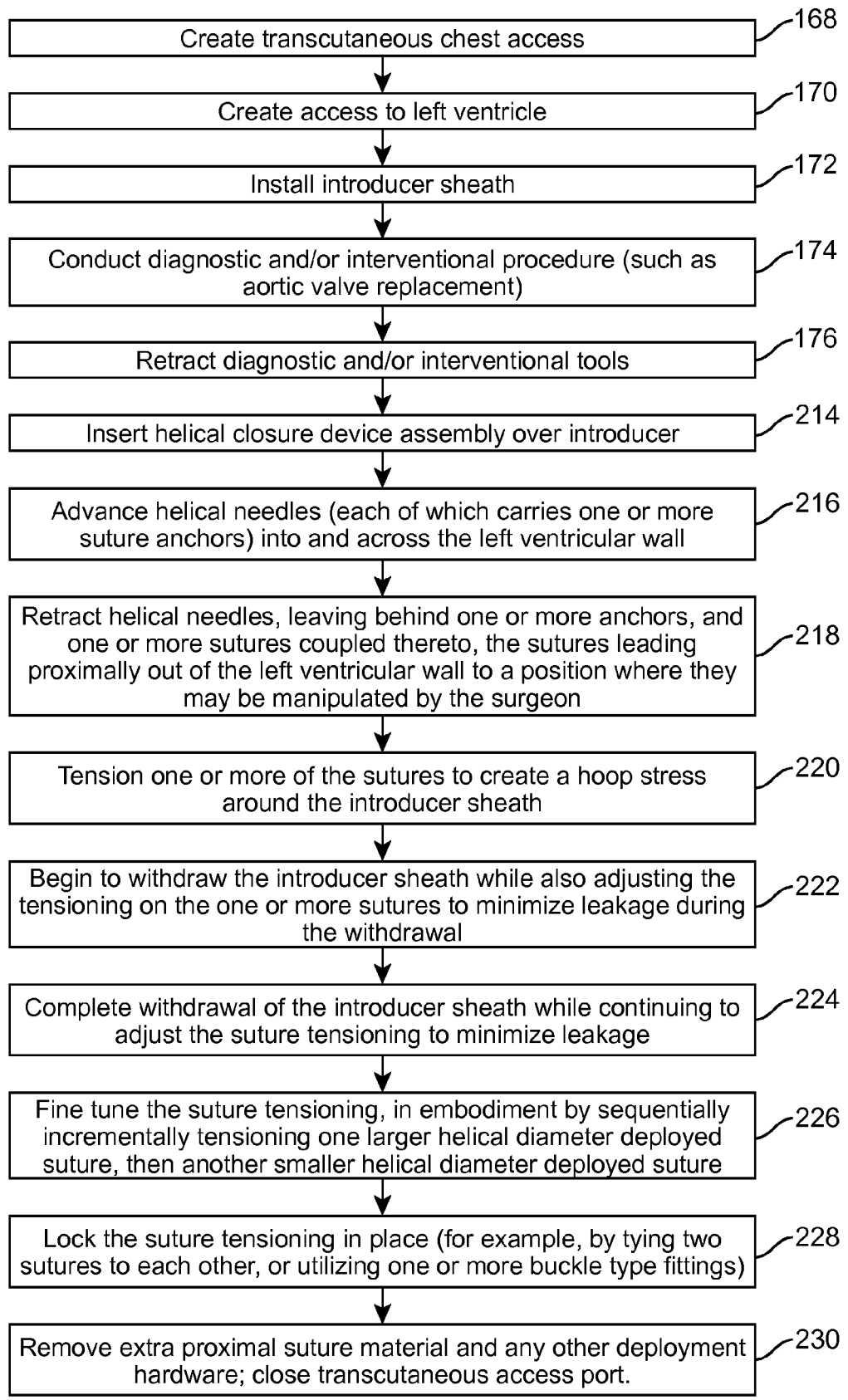
FIG. 13A illustrates various aspects of a method for creating and closing a transapical access, wherein anchors are placed across the thickness of the subject tissue structure, such as in the left ventricular cavity.
Figure 13B:
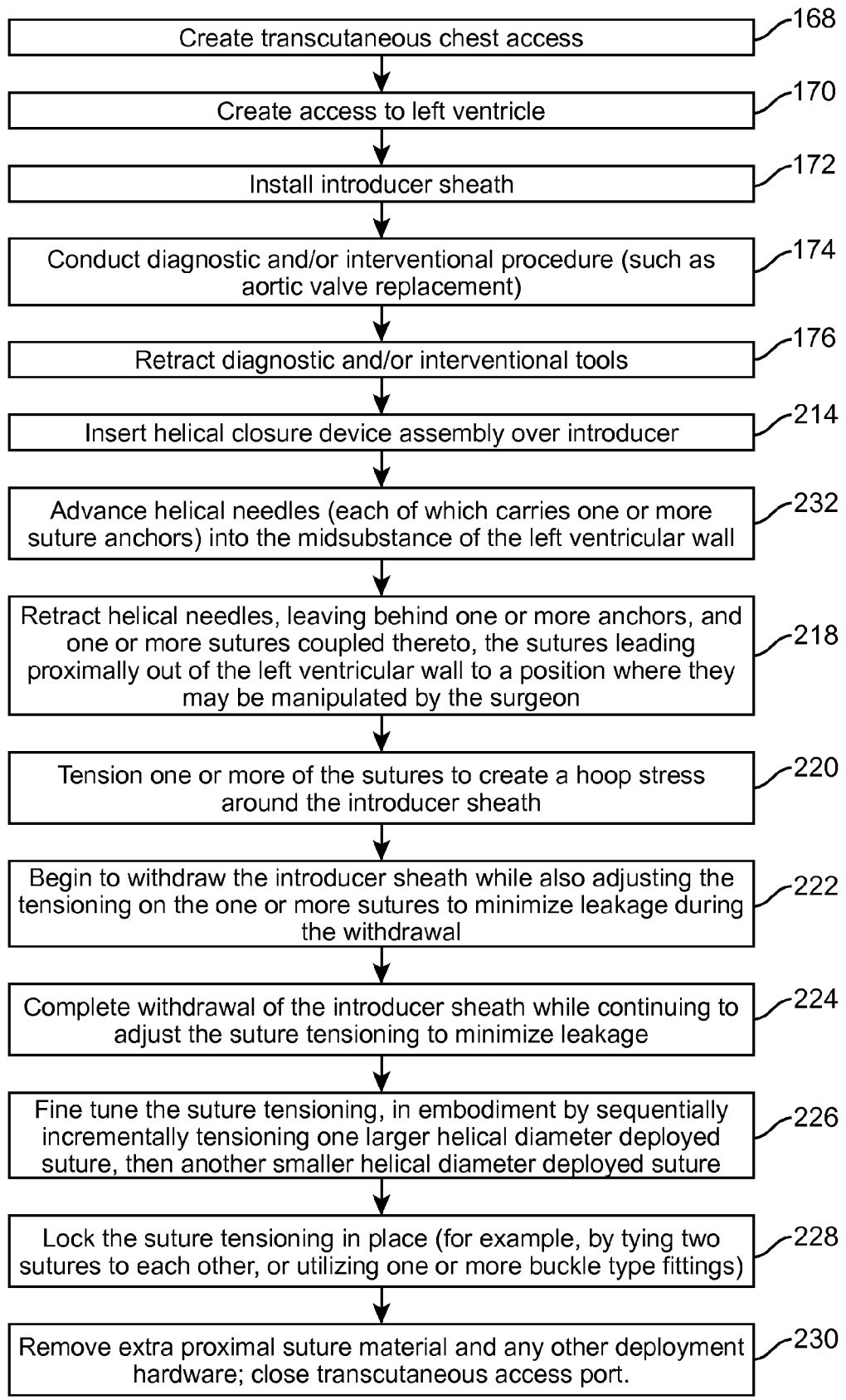
FIG. 13B illustrates various aspects of a method for creating and closing a transapical access, wherein anchors are placed within the thickness of the subject tissue structure, such as in the muscular walls of the left ventricle.

Referring to FIG. 13A, a method for creating, utilizing, and closing a transapical access wound using a helical needle configuration such as those described in reference to FIGS. 9A-9G and 10A-10B is depicted, with some steps similar to those described in reference to FIG. 4, for example. Subsequent to creation of access to the thorax (168), access to the left ventricle (170), installation of an introducer sheath (172), and use of such configuration to conduct a diagnostic and/or interventional procedure (174), the diagnostic and/or interventional tools may be retracted (176) before, after, or during advancement of a helical closure device over the introducer (214). One or more helical needles may be advanced across the left ventricular wall (216), and with backwards helical retraction (218) of the helical needles, one or more anchors may be left behind, the anchors being coupled to sutures which preferably are proximally threaded through the helical needles to a position wherein they subsequently may be controllably tensioned by the surgeon (220) to create a transient hoop stress around the introducer sheath to facilitate sealing around the introducer as the introducer is withdrawn (222, 224) with interactive adjustment of the suture tensioning to prevent leakage. The tensioning may be fine tuned (226), as described above, and the suture tensioning may be locked into place (288). Finally, extra uncoupled proximal suture material and any other deployment hardware may be removed, and the transcutaneous access port closed (230). Referring to FIG. 13B, an embodiment similar to that of FIG. 13A is depicted, with the exception that the helical needles are only advanced into the midsubstance of the left ventricular wall (232), not fully across such wall.

Figure 14A:
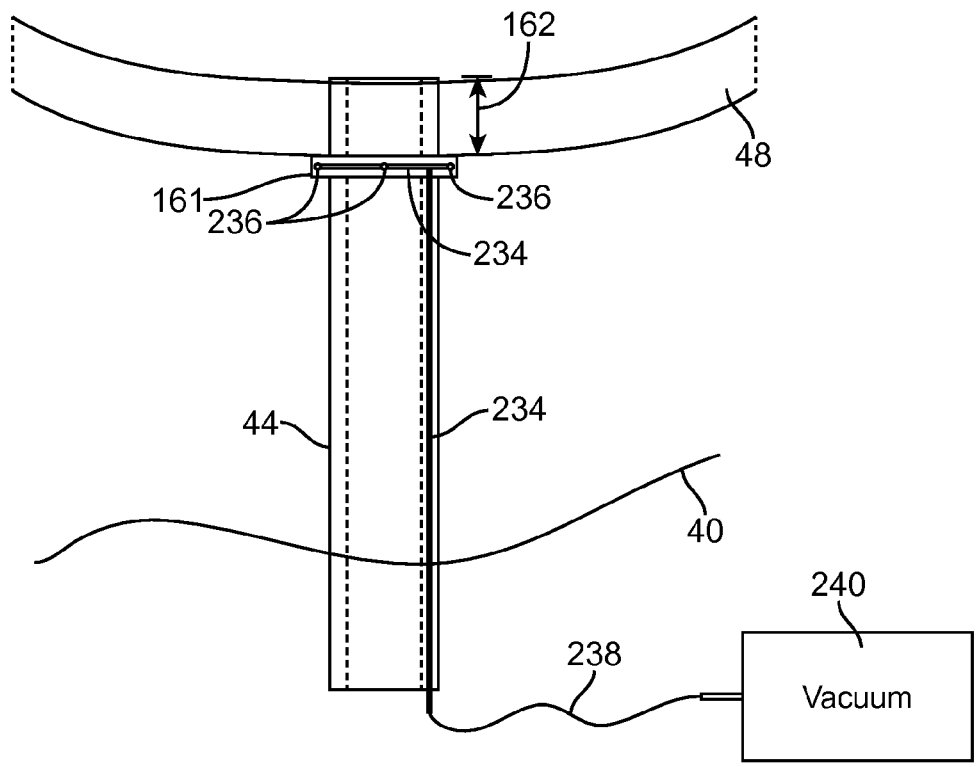
FIGS. 14A and 14B depict two embodiments of bolstering structures configured to limit protrusion of an introducer member into a tissue structure such as a left ventricular wall.

Referring to FIG. 14A, in one embodiment, a bolster flange (161) structure or feature may be included near the distal end of the introducer sheath (44) to only allow the introducer sheath (44) to protrude into the left ventricular wall (48) by a predetermined amount (162). In another embodiment, a bolster sleeve (163) may be movably coupled to the introducer sheath (44) to have a similar function, and in one embodiment, such bolster sleeve may be adjustable in position relative to the introducer sheath (44) to allow for adjustment of the predetermined sheath distal protrusion distance (162), using adjustable mechanical couplers such as the screw type couplers (164, 166) depicted in the embodiment of FIG. 14B.

Figure 14B:
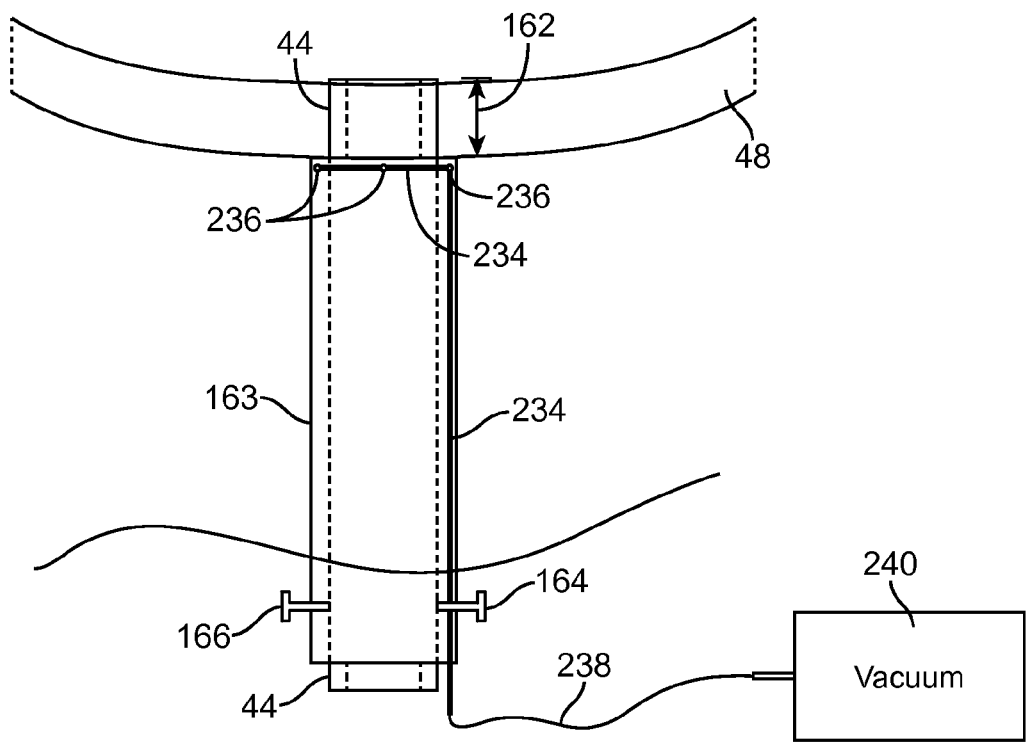
Figure 14C:
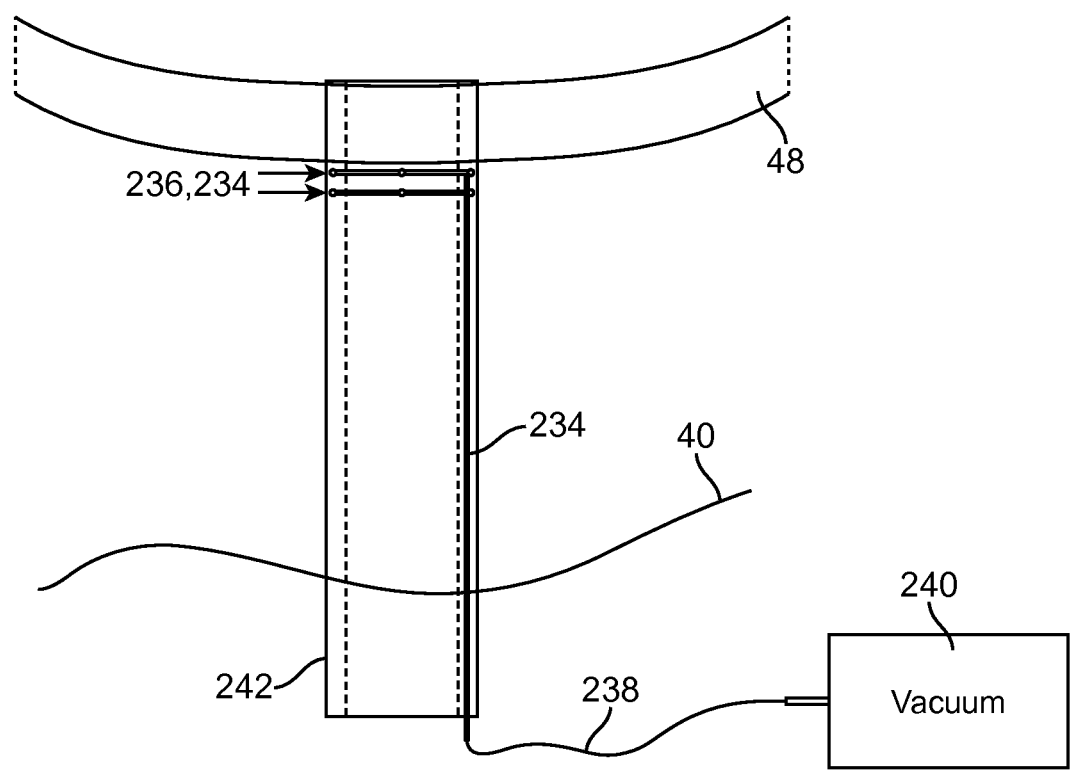
FIG. 14C depicts an embodiment having apertures configured for removing fluids near the pericardium in situ.

Also shown in FIG. 14A is a series of apertures (236) which are in fluid communication, via a vacuum lumen (234) and vacuum line (238), with a vacuum source or vacuum pump (240). The apertures (236) and vacuum (234) may be utilized to remove blood and other fluids which may ooze or leak from the surrounding tissues during the procedure. This may be important in transapical procedures to remove blood or other fluids which may, for example, enter the pericardium and potentially lead to pericardial tamponade or other undesirable conditions. The embodiment of FIG. 14A features the apertures (236) distributed around the bolster flange structure (161). Referring to FIG. 14B, a similar configuration has apertures distributed around the distal portion of the bolster sleeve (163). Referring to FIG. 14C, another embodiment shows apertures (236) distributed around an introducer sheath (242) that does not have a bolstering structure (i.e., a bolstering structure need not be present for the vacuuming apertures to be featured in a given embodiment), and has two circumferential sets of apertures (236) to provide further vacuuming access; many distal aperture configurations may be suitable.

Figure 14D:
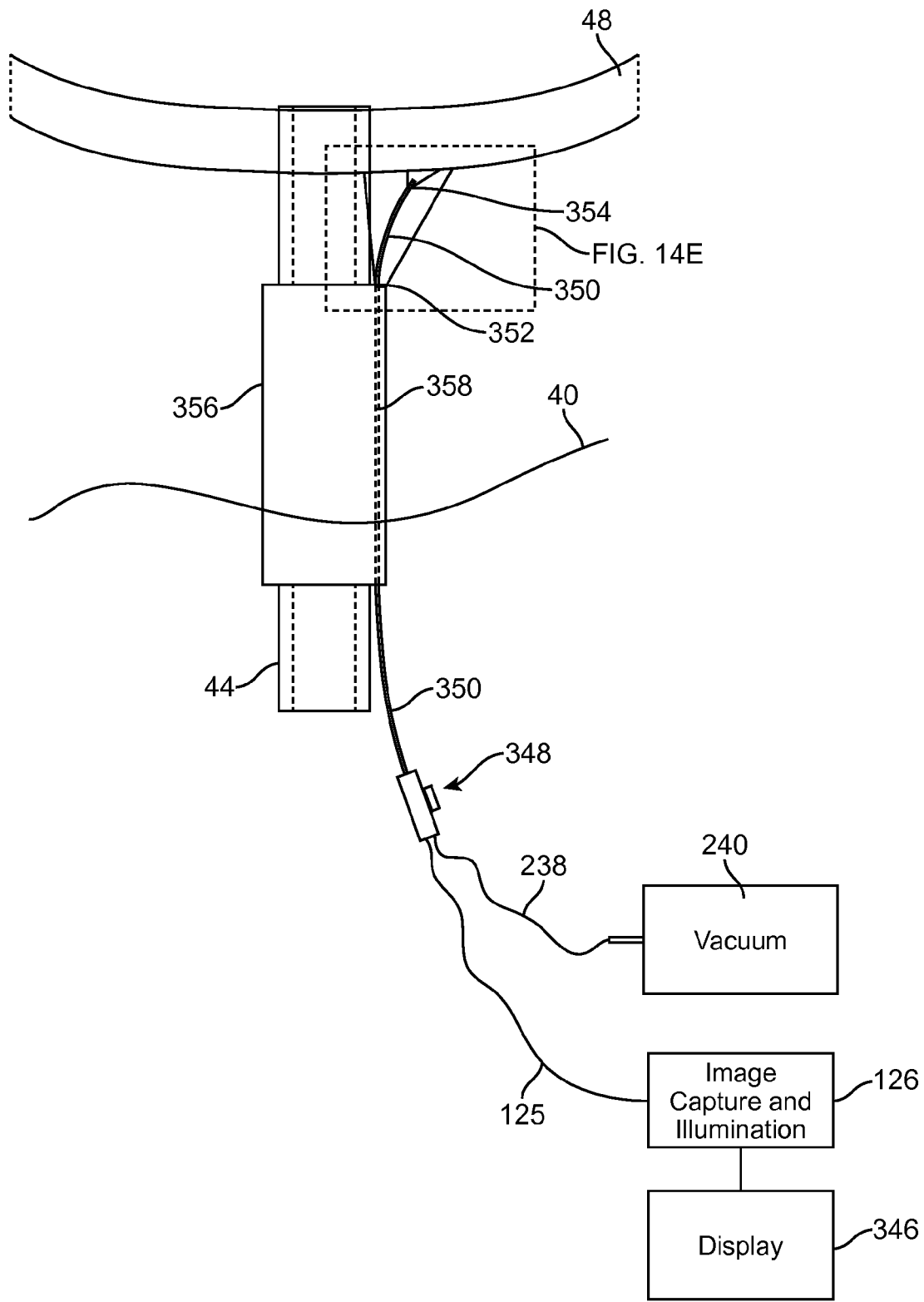
FIGS. 14D-14E depict an embodiment wherein a steerable catheter with visualization and vacuum capabilities may be movably coupled to collar member positioned around an introducer or similar member.
Figure 14E:
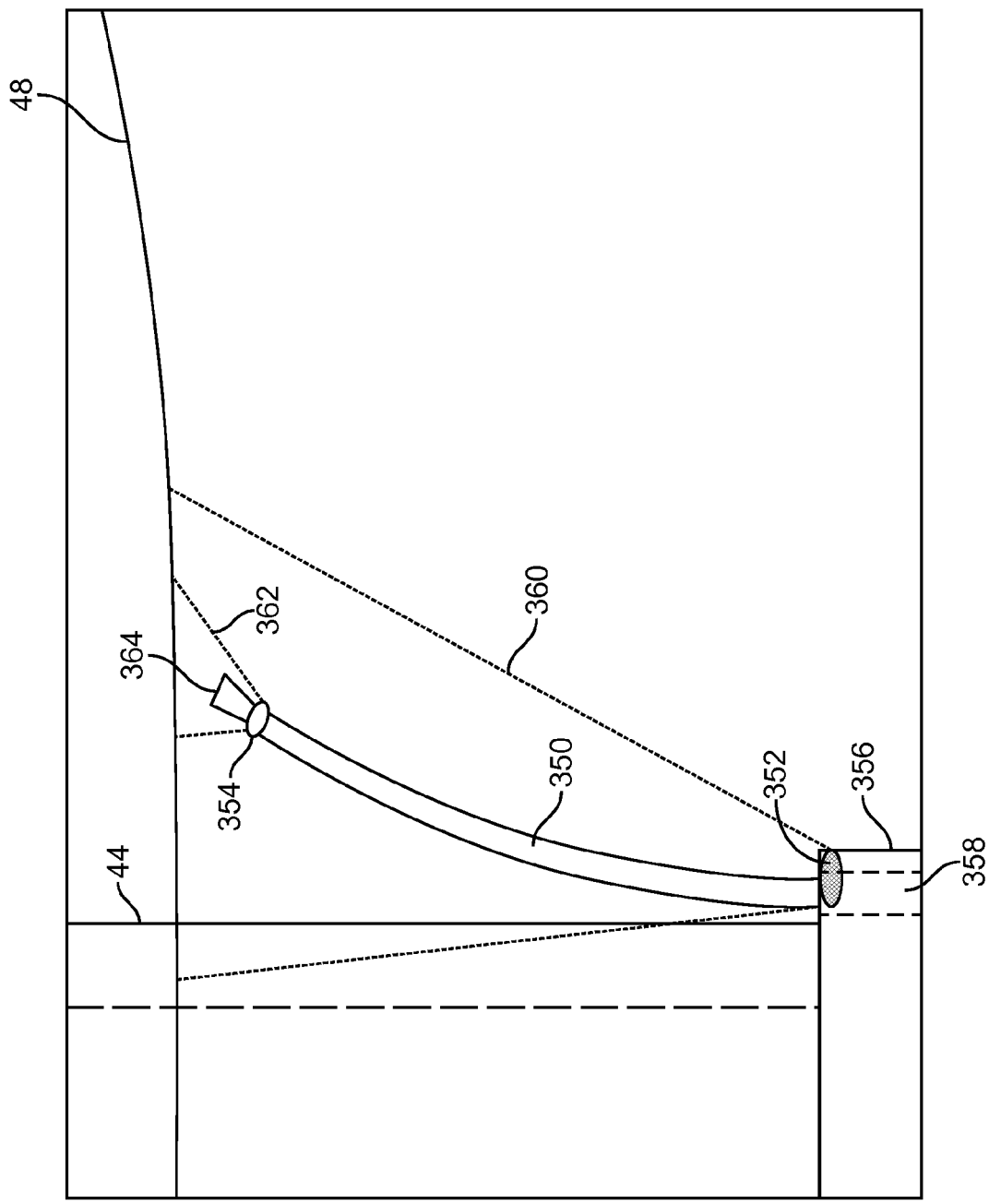

Referring to FIG. 14D, another embodiment is shown wherein an elongate steerable instrument body (350), such as one associated with a manually or electromechanically steerable catheter system, may be passed through a lumen (358) formed in a movable collar member (356) coupled around the introducer (44). Preferably the movable collar member (356) may be rotated and inserted/withdrawn relative to the introducer (44). Preferably the steerable instrument body (350) may be inserted/withdrawn and rotated relative to the movable collar member (356). Preferably the distal end of the elongate steerable instrument (350) carries an image capture interface (354), such as a digital imaging chip or fiber imaging bundle termination, as well as an illumination source (such as a light fiber termination—preferably positioned immediately adjacent the image capture interface 354) and vacuum inlet (364, such as the end of a tube leading proximally to the vacuum source 240). The depicted embodiment has a manual handle and steering interface (348) disposed proximally, and leads (238, 125) connecting a vacuum source (240) and illumination/image capture system (126) to the elongate body (350) and distally disposed illumination outlet, image capture interface (354), and vacuum inlet (364). Pull-wires (not shown) may operatively couple manipulation elements of the proximal control interface (348) to portions of the elongate body to provide for controlled steerability, preferably to provide at least controllable pitch and yaw steerability. A display may be operatively coupled to the image capture and illumination system (126) to facilitate operator observation of activity within the field of view of the distally disposed image capture interface. The degrees of freedom of the steerable instrument (350) and movable collar member (356) working together provide an operator with the ability to move the distal portion of the steerable instrument all around the immediate area where the introducer (44) has been passed through the left ventricular wall (48). The distal portion of the movable collar member (356) may also feature an image capture interface (352) configured to have a distally-oriented field of view to generally capture activity of the distal portion of the steerable instrument (350); this second image capture interface (352) may also be operatively coupled to the image capture and illumination system (126) and display (346), and a second illumination outlet may be featured adjacent the second image capture interface (352). Referring to FIG. 14E, a close-up view of certain aspects of the illustration of FIG. 14D is depicted. In practice, the depicted embodiment may be utilized to examine the area around the introducer (44) and heart wall (48) junction, and vacuum any extra fluids which may be present. For example, in one embodiment, the movable collar member may first be inserted through the transcutaneous chest port and into a position as shown in FIG. 14D. The image capture interface (352, a digital imaging chip, in one embodiment) and roll+insertion/withdrawal degrees of freedom of the collar member (356) may be utilized to generally investigate the area around the introducer/heart wall junction, with the field of view of the collar member image capture interface (352) having a distally-oriented field of view (360) configured to capture not only the introducer/heart wall junction area, but also the distal portions of instruments passed through the working lumen (358) formed within the collar member (356)—as in the depicted embodiment, wherein the distal portion of the steerable instrument (350) is positioned through such lumen (358) and free to controllably articulate or bend around in the area to investigate nearby structures and vacuum away fluids. The distal portion of the steerable instrument (350) in the depicted embodiment carries its own image capture interface (354), which also has a distally-oriented field of view (362) configured to capture images of nearby tissues, as well as at least a portion of the distal vacuum interface (364)—to enable the operator to navigate the instrument around, capture images of structures around the instrument, and also capture images of the distal vacuum interface (364). Such an arrangement allows the operator to use the display to see the view from the second image capture interface (352), as well as a view from the first image capture interface (354), to move the various structures appropriately, see what he wants to vacuum, and operate the vacuum with real time, or near real time, visual confirmation of what he is vacuuming. In one embodiment, this arrangement may be utilized to vacuum away blood and other fluids which may be present in the region, to prevent cardiac tamponade or other undesirable fluid-related scenarios.

Figure 15A:
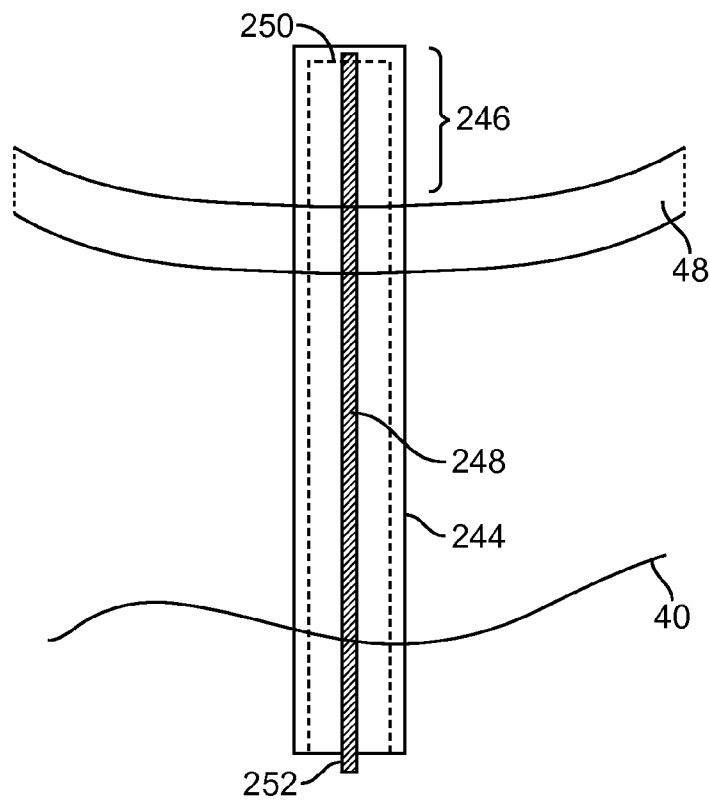
FIGS. 15A-15B depict an introducer embodiment with a diametrically-expandable distal portion.
Figure 15B:
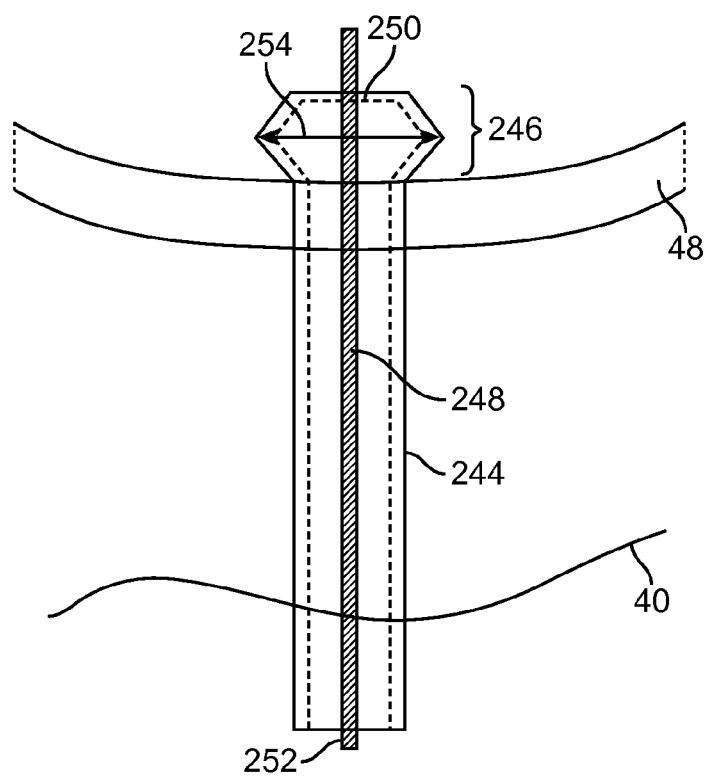

Referring to FIGS. 15A and 15B, another embodiment of an introducer (244) is depicted having a diametrically expandable (i.e., the outer diameter of its distal portion is controllably expandable) distal portion, which is configured to assist in preventing the introducer from being pulled or removed proximally of the tissue wall (48) until a time that is desired. As shown in FIG. 15A, the introducer (244) may be inserted as described above, but to an increased depth to allow for a distal portion (246) to protrude into the cavity opposite the tissue structure wall (48). At a desired time, the distal portion (246) may be controllably expanded to have a larger outer diameter (254) by rotating a structural member (252) from a proximal location, causing the structural member to be loaded in tension due to its coupling distally (250) with the introducer (244). When desired, the structural member (252)

may be counter-rotated to cause the distal portion to again resume the configuration shown in FIG. 15A, to facilitate removal of the introducer (244).

Figure 16A:
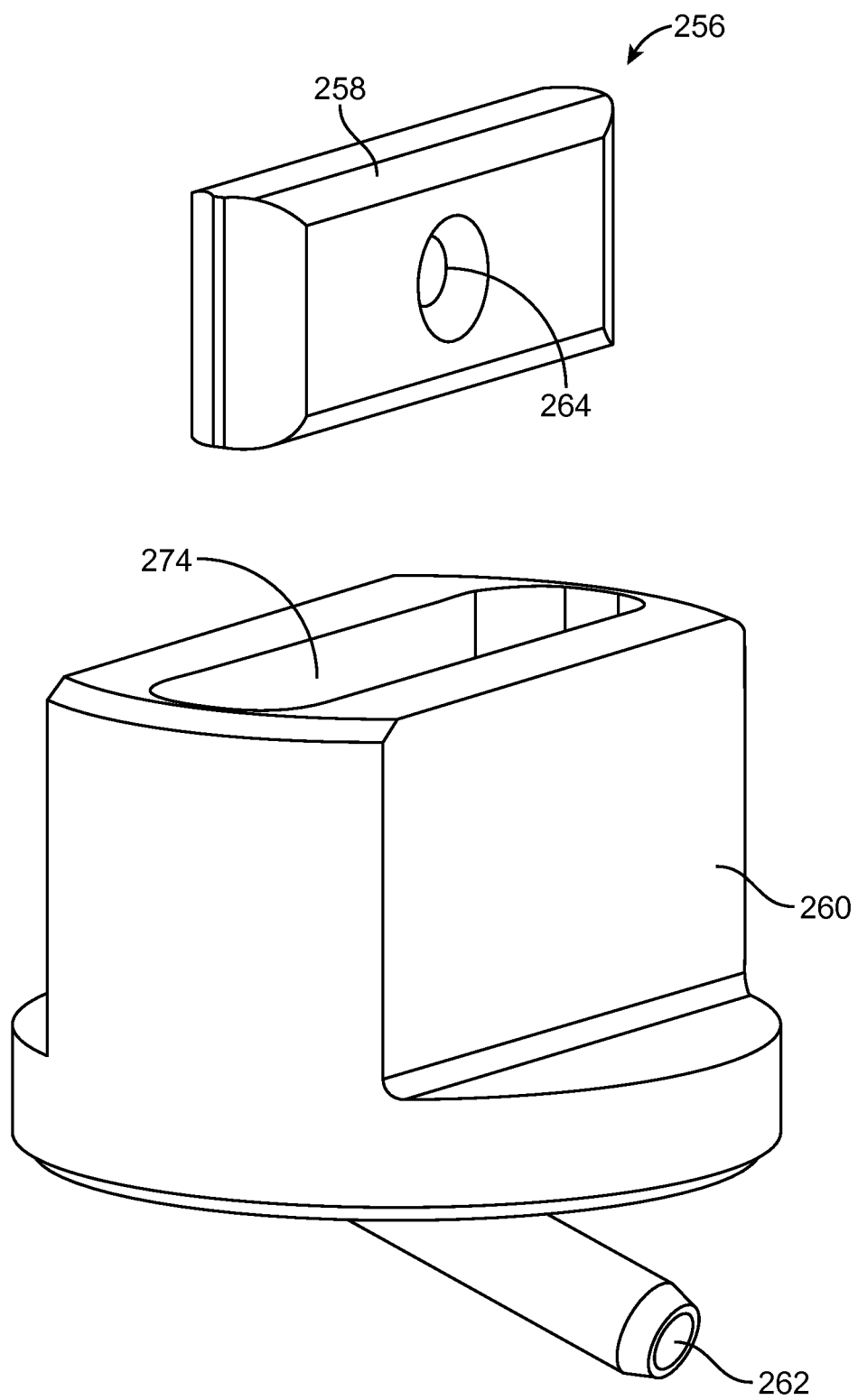
FIGS. 16A-16E depict aspects of a buckle fastener assembly and deployment thereof.
Figure 16B:
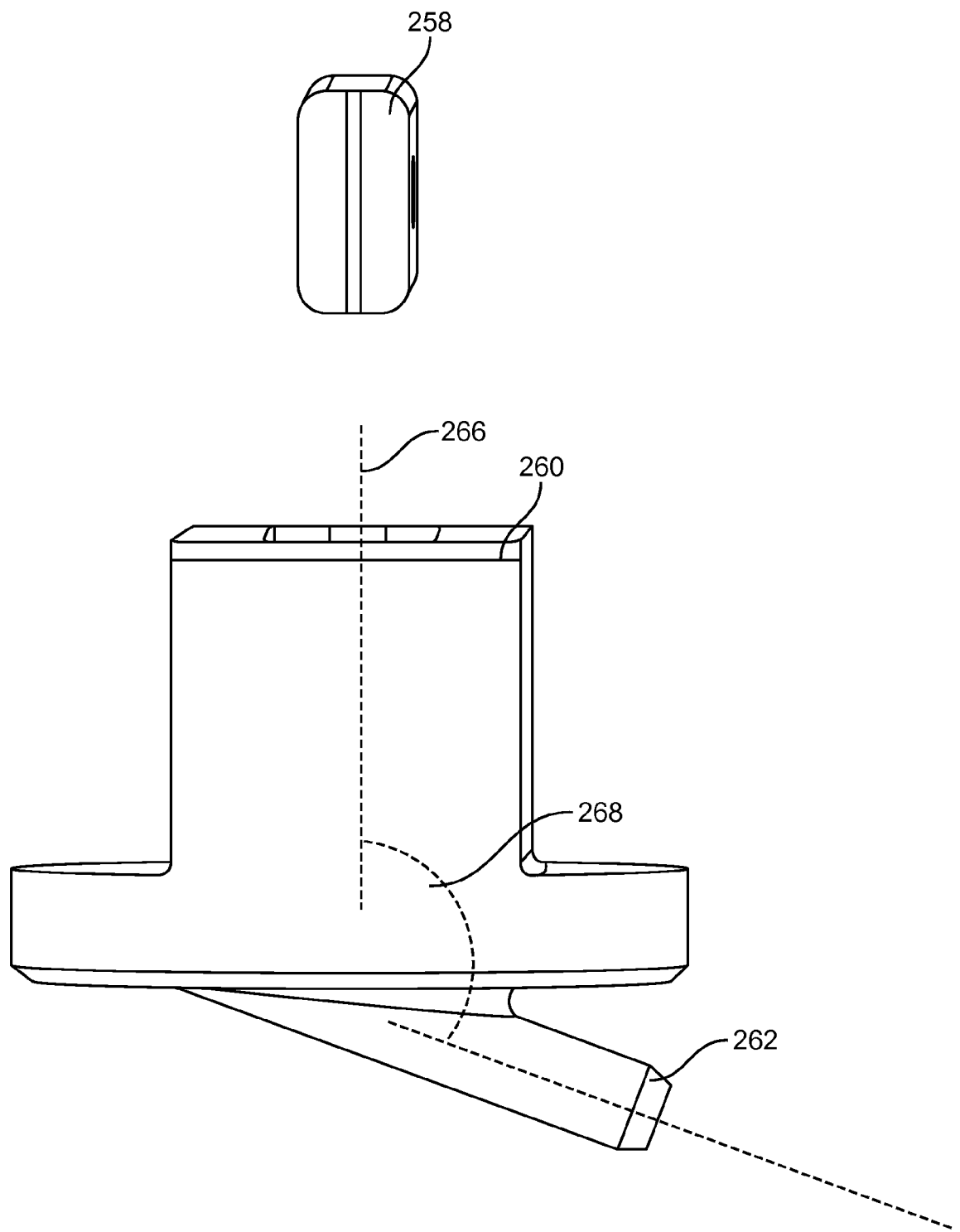
Figure 16C:
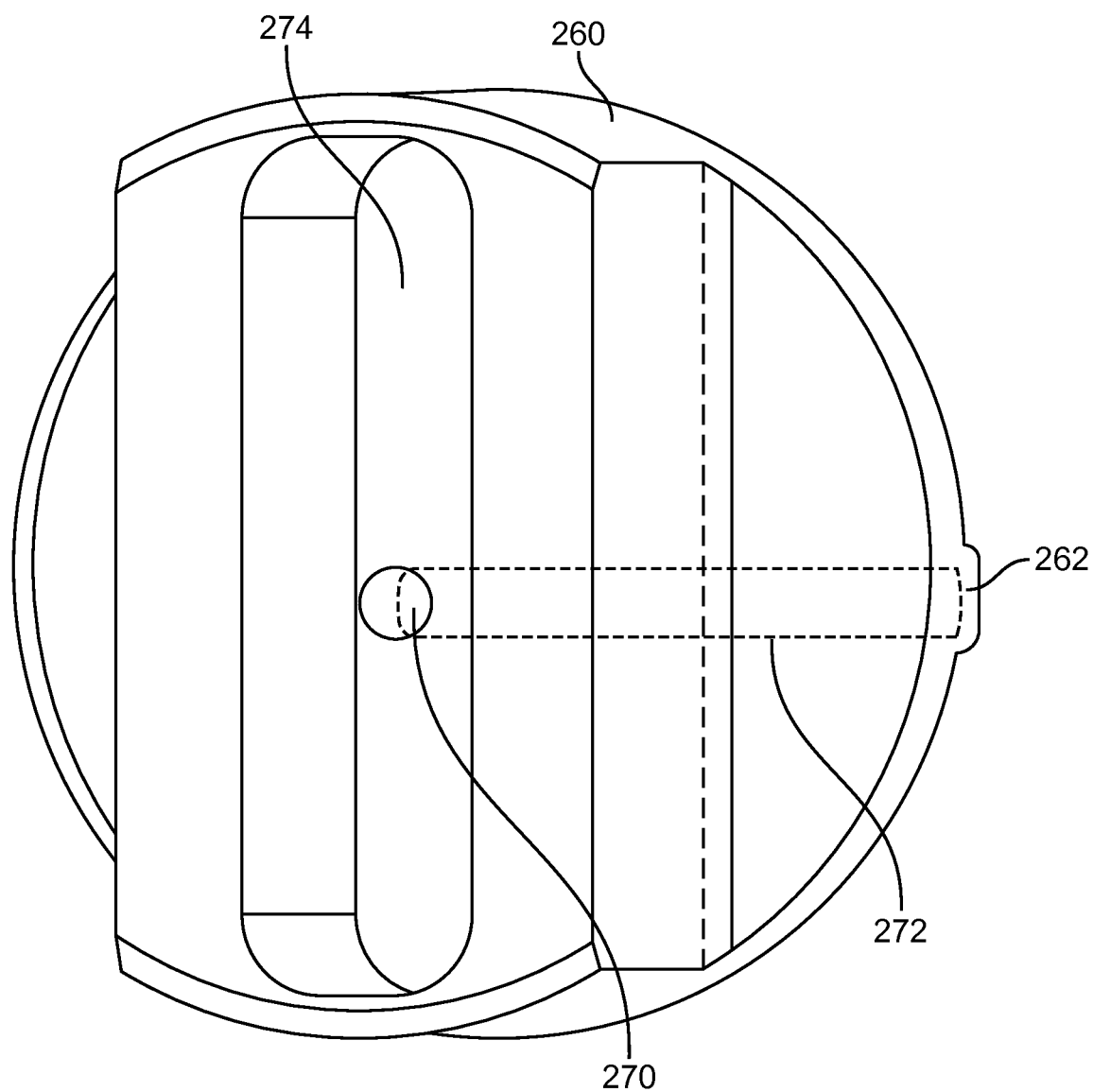
Figure 16D:
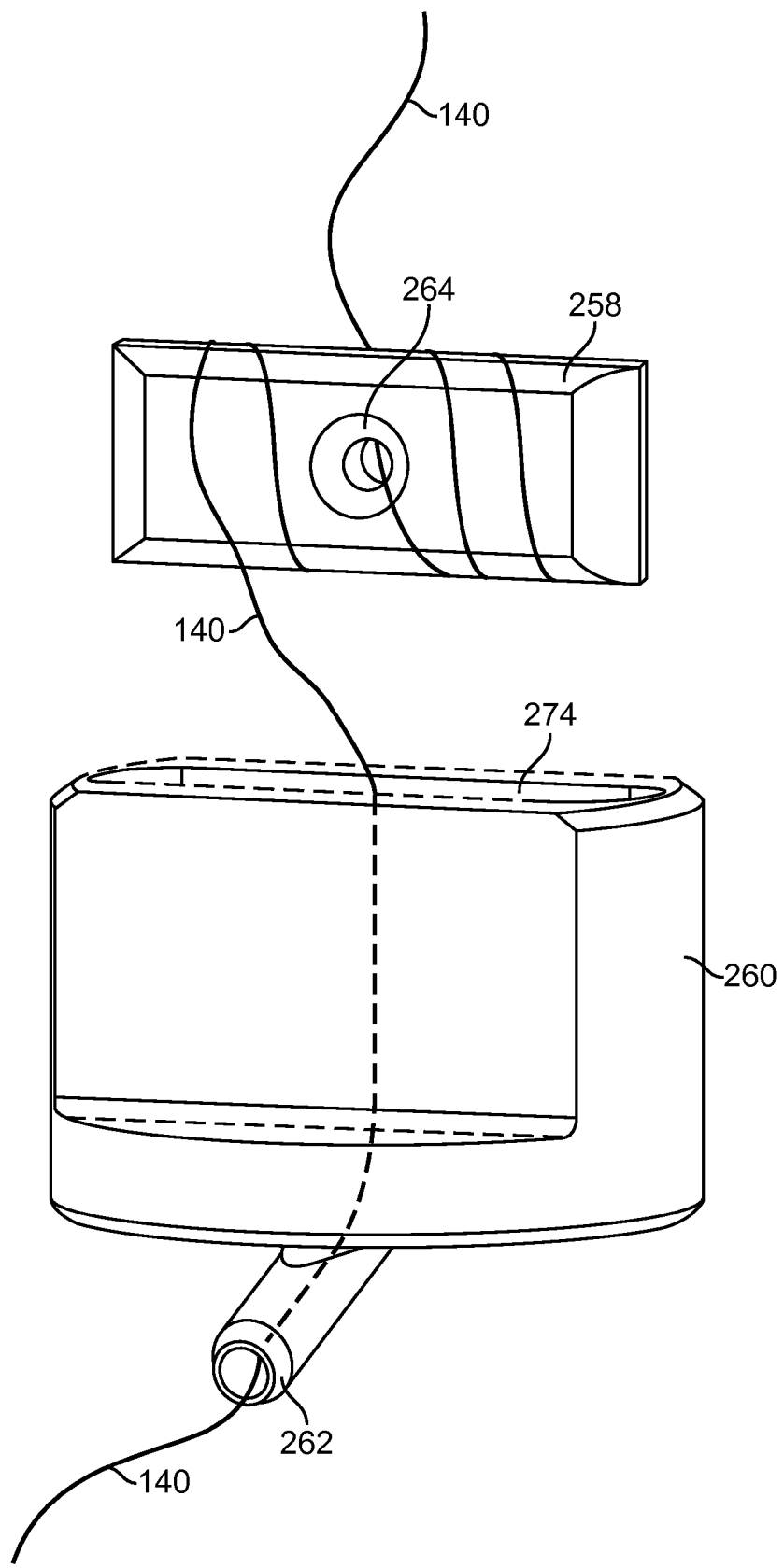
Figure 16E:
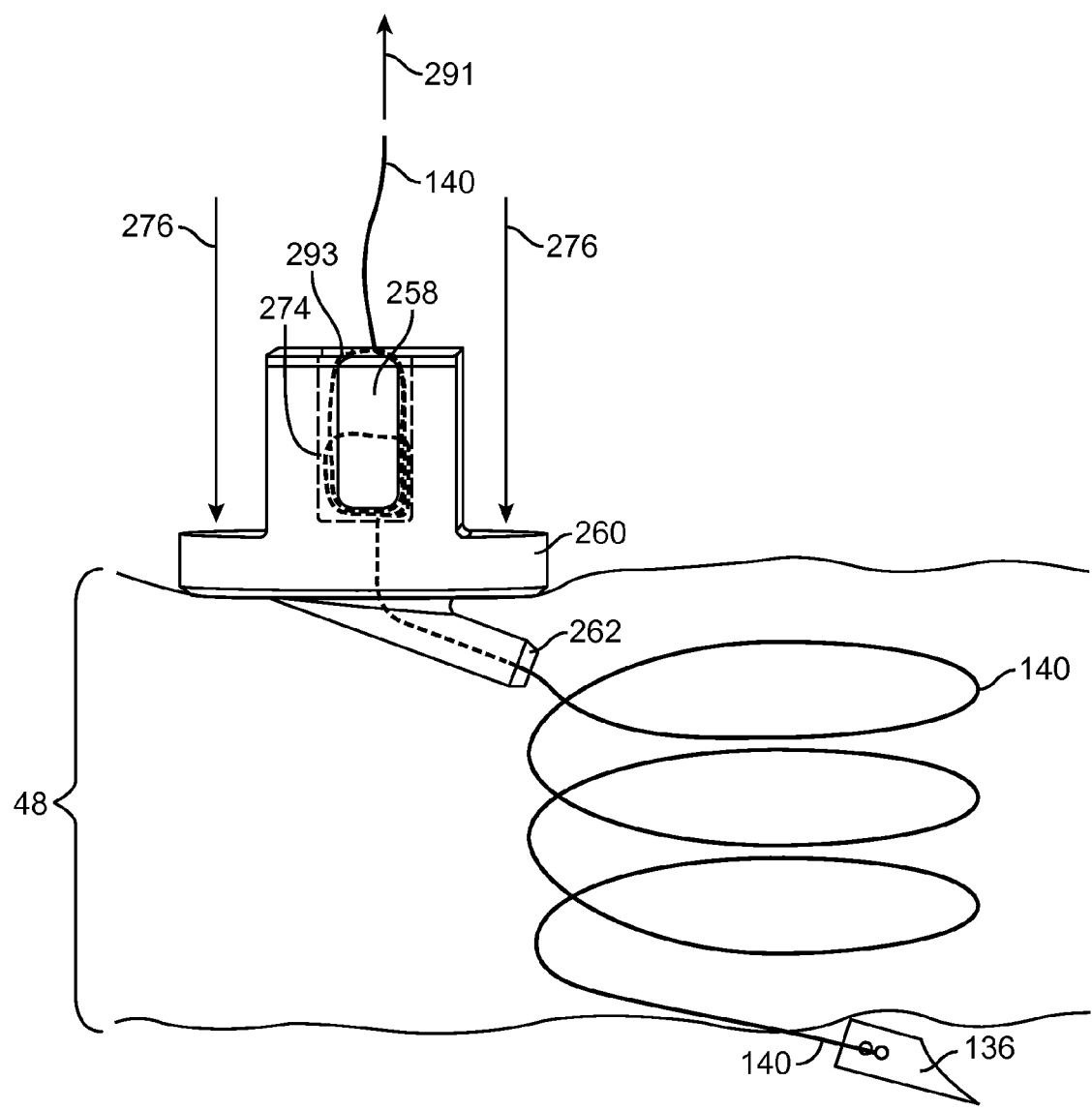

As described above in reference to FIGS. 10B and 11B, for example, small fasteners may be utilized to maintain tension on deployed sutures. Referring to FIGS. 16A-16E, one embodiment of a buckle type fastener assembly (256) is depicted wherein a winding block (258) is configured to be deposited into a block cavity (274) of a buckle body member (260). The winding block (258) comprises an aperture (264) through which suture material may be passed and/or fastened, and is configured to have suture material wound around it and passed down through a distal outlet to access nearby tissue structures. FIG. 16B shows that the distal outlet (262) may be positioned at an angle (268) relative to a vertical line (266), the angle selected to accommodate a helical pitch of a deployed helical suture—so that tension applied through the associated suture is applied at least somewhat parallel to the path of the suture, and is more likely to retain the helical pattern of the suture deployment (and less likely to cause shearing or cutting loads in nearby tissue as would suture loads that are more perpendicular to the helical pattern; such perpendicular loads are more likely to be present without some redirecting of the suture tensile loading). In other words, the angulation (268) of the suture pathway through the buckle body serves as a force re-director. FIG. 16C depicts a top orthogonal view showing the suture pathway (272) through the lower buckle body (260). Referring to FIG. 16D, in application and before complete deployment, a suture (140) leads from a proximal location, helically around the winding block (258) and through the aperture (264) thereof, into the block cavity (274), through the distal outlet (262), and into contact with the subject tissue structure. Referring to FIG. 16E, one deployment scenario is depicted to further illustrate use of the depicted configuration. As shown in FIG. 16E, a suture (140) has been helically deployed with an anchor (136) at its distal end on the opposite surface of a tissue structure, such as a left ventricular wall (48). The buckle body (260) may be slid over the suture distal outlet first (262), along with the winding block (258) with winding loops of suture around it. With a compressive load (276) to press the buckle body (260) against the tissue structure (48), a containment member (293) to retain the winding block (258) within the block cavity (274), and a tensile load (291) upon the proximal end of the suture (140), the suture may be locked into tension. The looping pattern of suture around the winding block (258), along with the physical confinement of the winding block in the block cavity (274) and the related engagement loads, result in a one-way tightening mechanism such that the slack may be pulled out with proximal tension, but movement of the suture in the other direction is prevented by the buckle assembly.

Figure 17A:
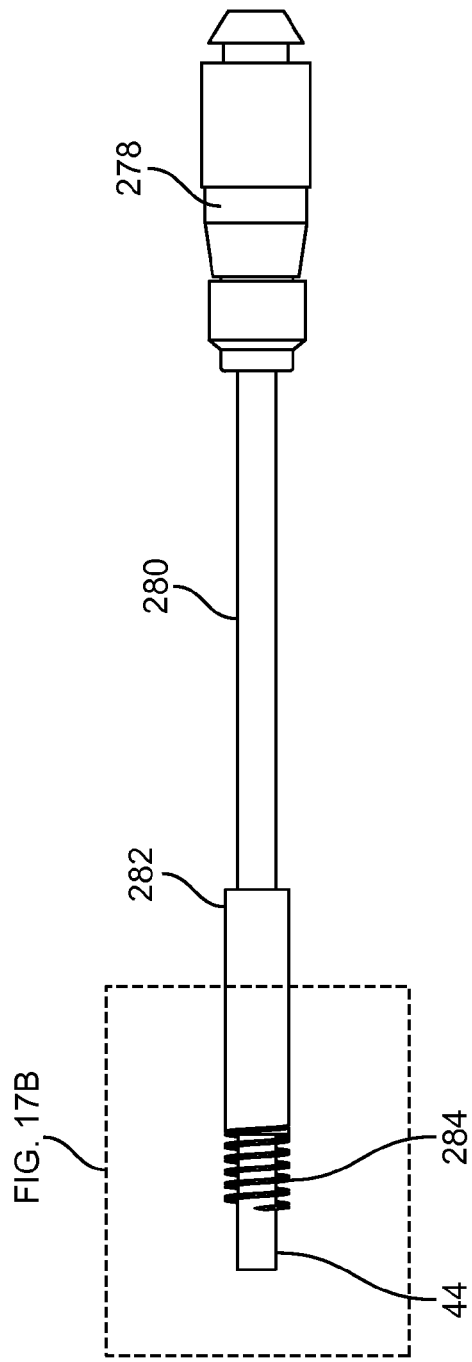
FIGS. 17A-17E illustrate aspects of a helical suture member deployment paradigm.
Figure 17B:
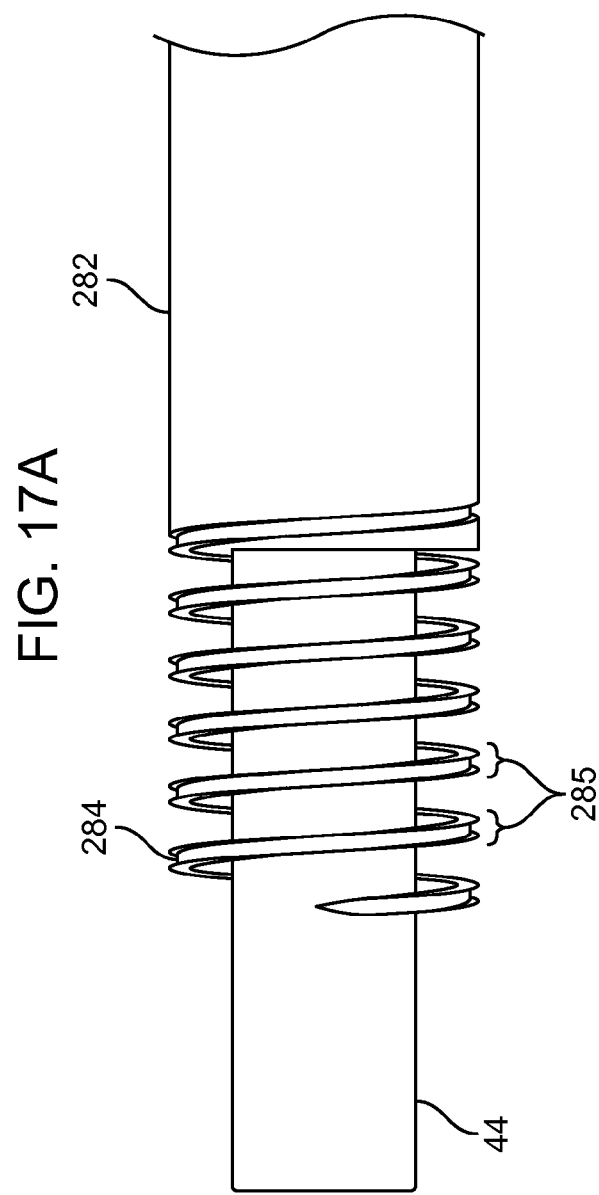
Figure 17C:
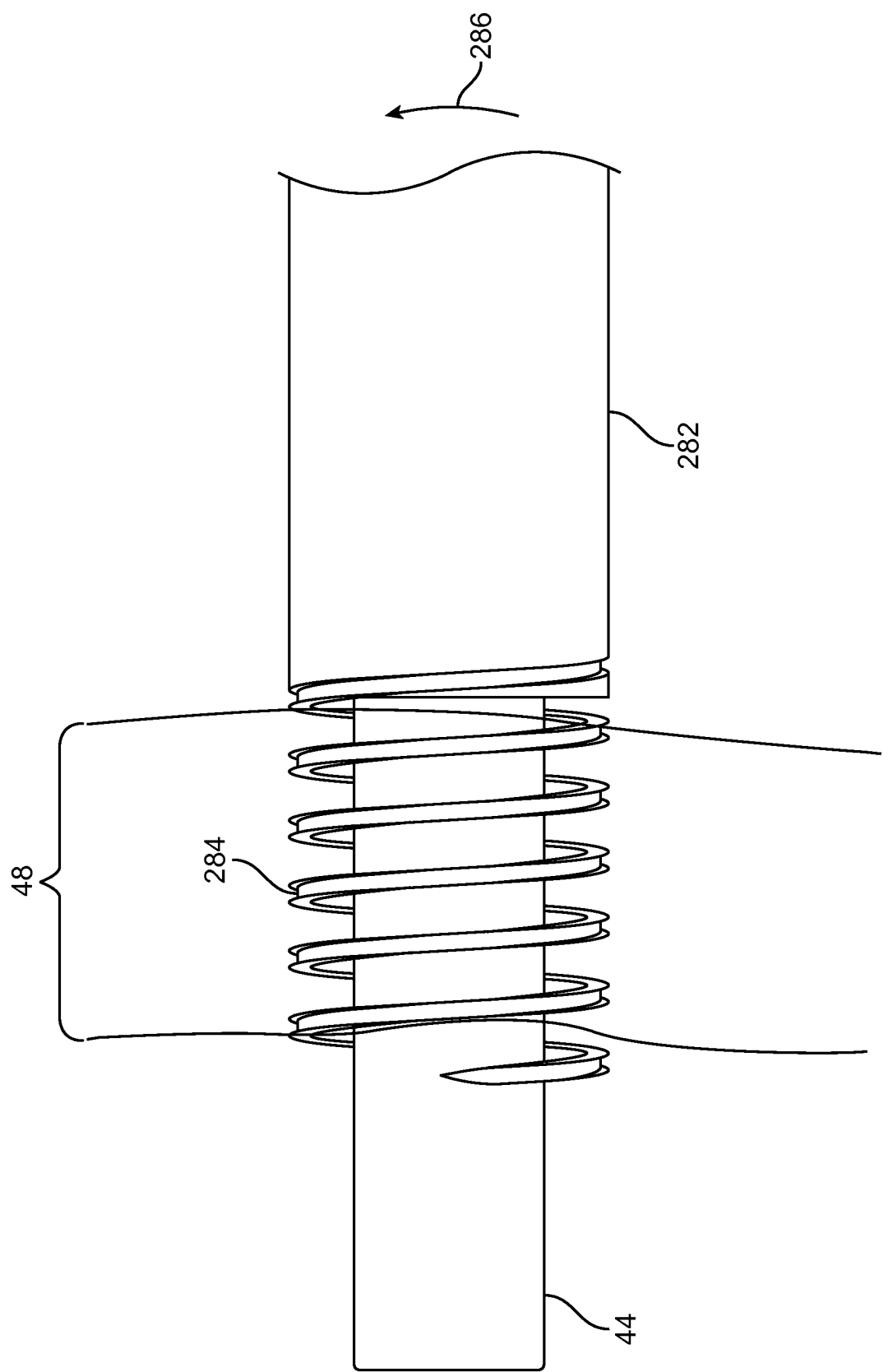
Figure 17D:
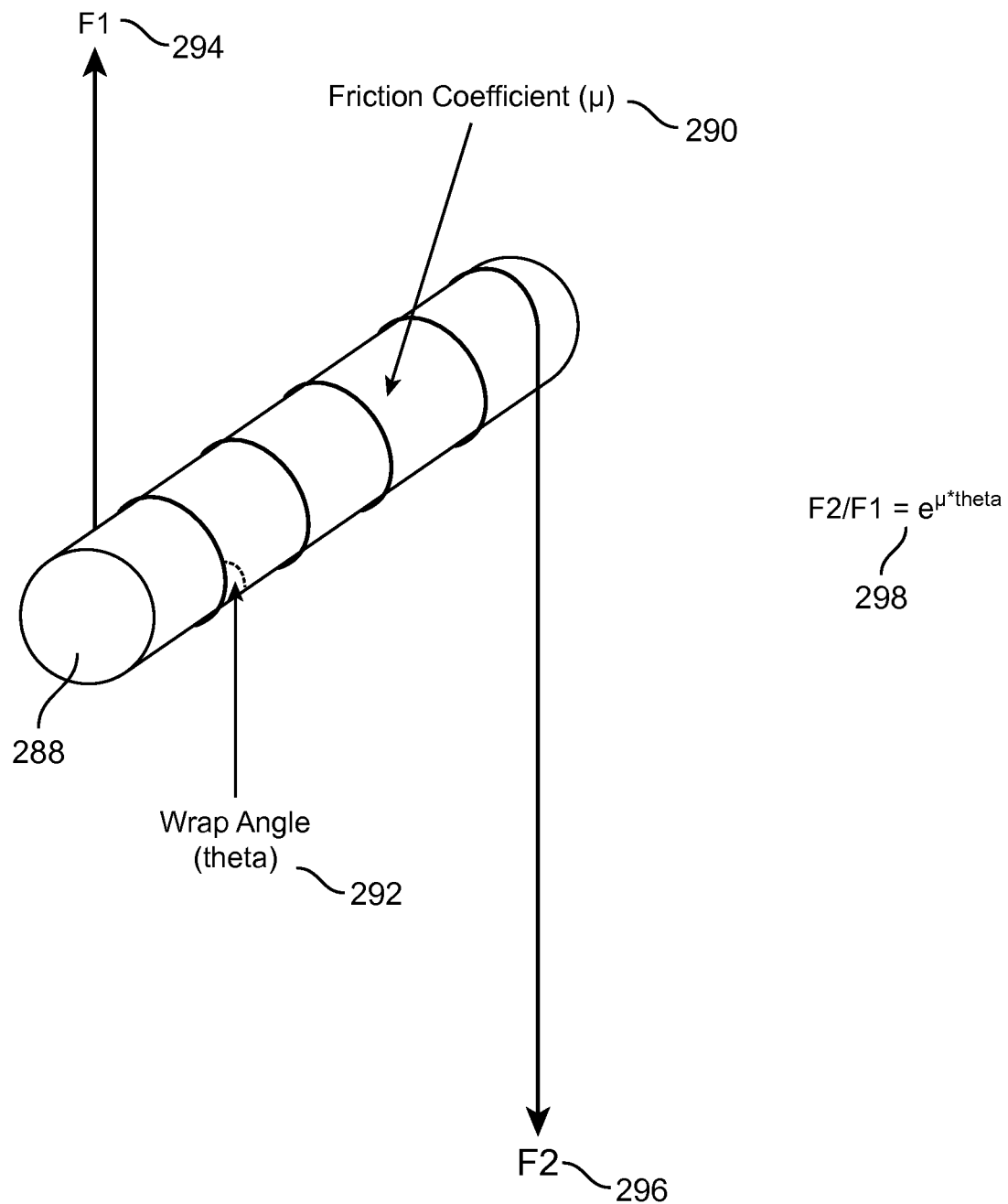
Figure 17E:
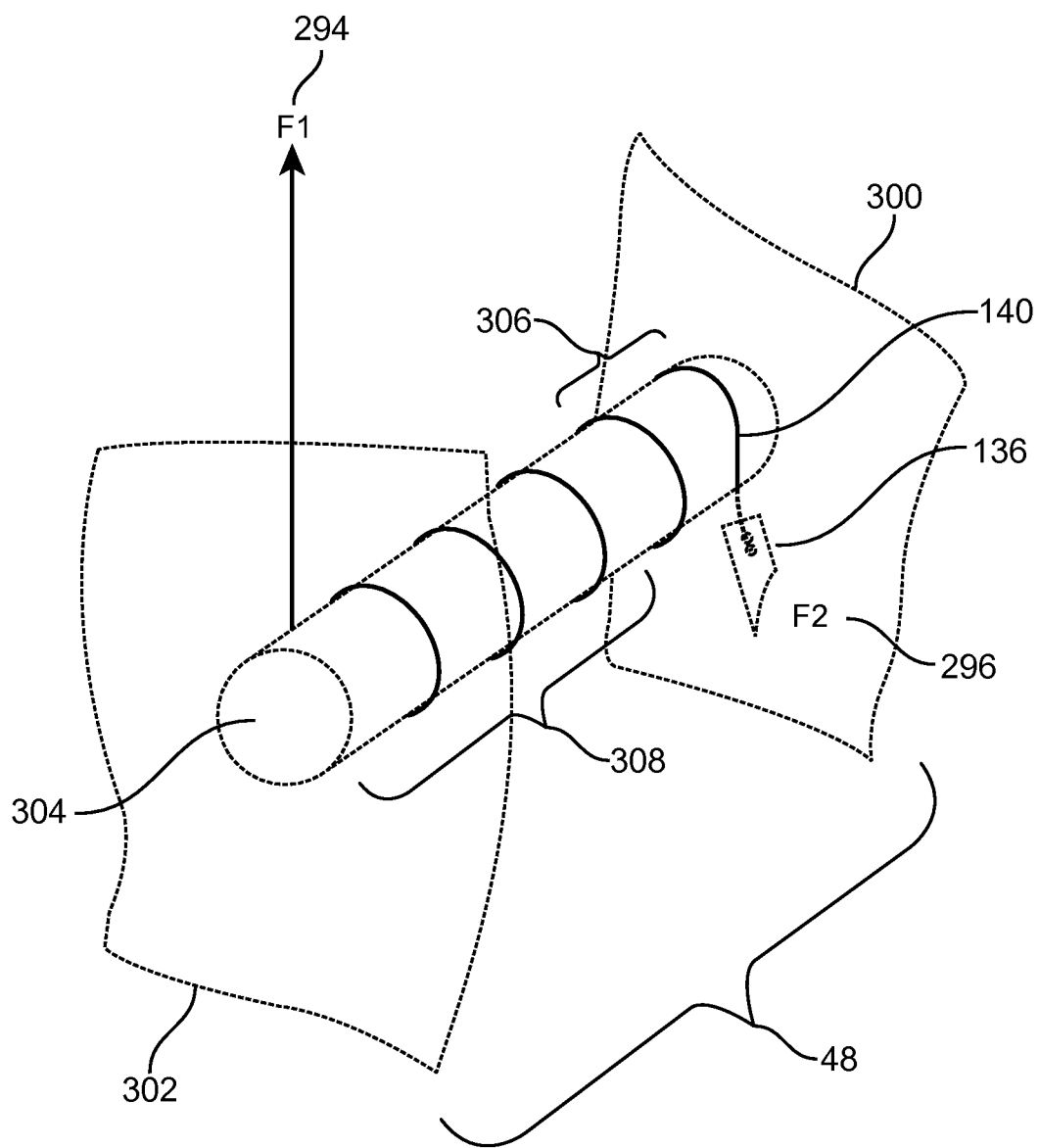

Referring to FIGS. 17A-17E, a helical suture deployment embodiment is depicted wherein the suture material may be carried upon an outer rail (285) of a helical needle (284) and deployed away from the needle with counter-rotation action of the helical needle, such as by manual rotation of a proximal handle (278) from outside of the patient's body. The handle (278) may be coupled to the helical needle (284) with an elongate instrument shaft (280) and helical needle coupler (282), which may also be coupled to a portion of an instrument such as an introducer sheath (44). The suture rails (285) are shown in further detail in the close up view of FIG. 17B. Referring to FIG. 17C, in use, the helical needle (284) may be rotated (286) into a tissue structure such as a left ventricular wall (48) to deposit a suture with distal anchor (not shown). One of the challenges in deploying a suture from such a rail configuration is tightening the helical suture once it has been helically positioned, since friction becomes a significant factor, and nonlinearities of the viscoelastic tissue can magnify this. When a suture or other tensile member is helically wrapped around a shaft, as shown in FIG. 17D, for example, we have determined that the maximum ratio of loads that may be applied (F2 to F1—elements 296 and 294, respectively) may be calculated with the depicted formula (298), wherein theta (292) is the helical wrap angle on the shaft, and mu (290) is the static friction coefficient between the tensile member material and the shaft (288). Referring to FIG. 17E, these relationships may be applied to a helical suture (140) deployed in situ through a left ventricular wall (48) between two surfaces (300, 302) of the heart, wherein a "shaft" or "column" of tissue (304) is effectively captured by the helical winding pattern which may be formed by a helical needle with rail-deployment. An anchor on the opposite side of the distal surface (300) creates F2 (296), while a proximal pull creates F1 (294). We have found in experiments that in certain configurations, with a proximal pull (294), we are only able to tighten the distal few windings (306) of the helically deployed suture, while the proximal windings (308) may stay relatively slack. This is a result of the equation (298) of FIG. 17D at work—the friction formed by the large surface of windings is too great to be entirely tensioned by the applied loads. As a result, we have created techniques to sequentially tighten portions of the helical suture, as described further in reference to FIGS. 18B and 18C.

Figure 18A:
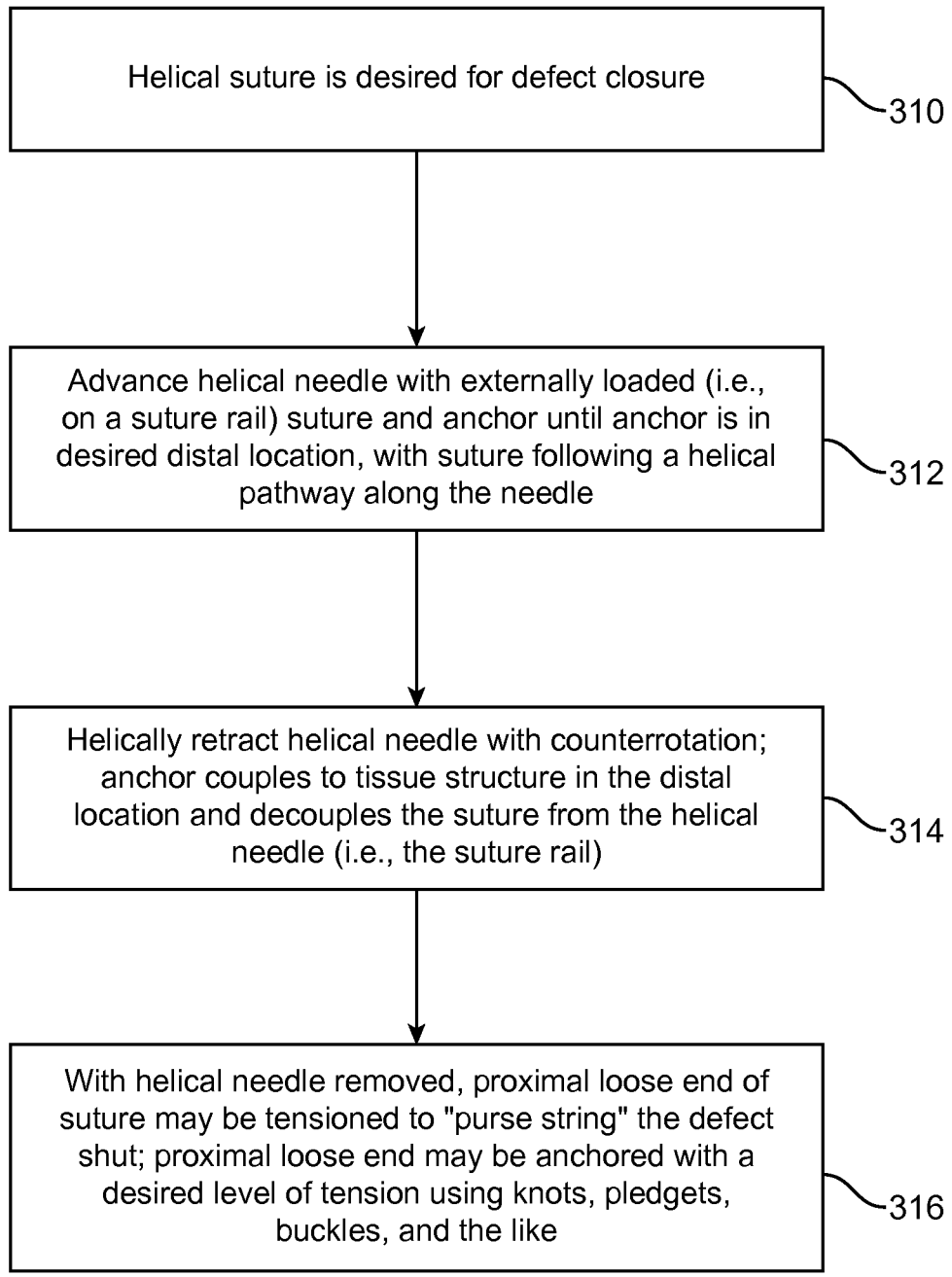
FIGS. 18A-18C illustrate methods for utilizing helical needle embodiments to close tissue defects with a purse string suturing effect.

Referring to FIG. 18A, in a simple configuration, a helical suture is desired for a defect closure (310), a helical needle with rail configuration is driven to place an anchor at a desired distal location (312), and the needle may be helically retracted to decouple the suture from the needle suture rail (314) after which it may be tensioned proximally to create a purse-string closure of the wound, and fastened to retain tension (316). The helical winding angle, friction surfaces, and number of windings may be selected to allow for complete tensioning with proximal loading.

Figure 18B:
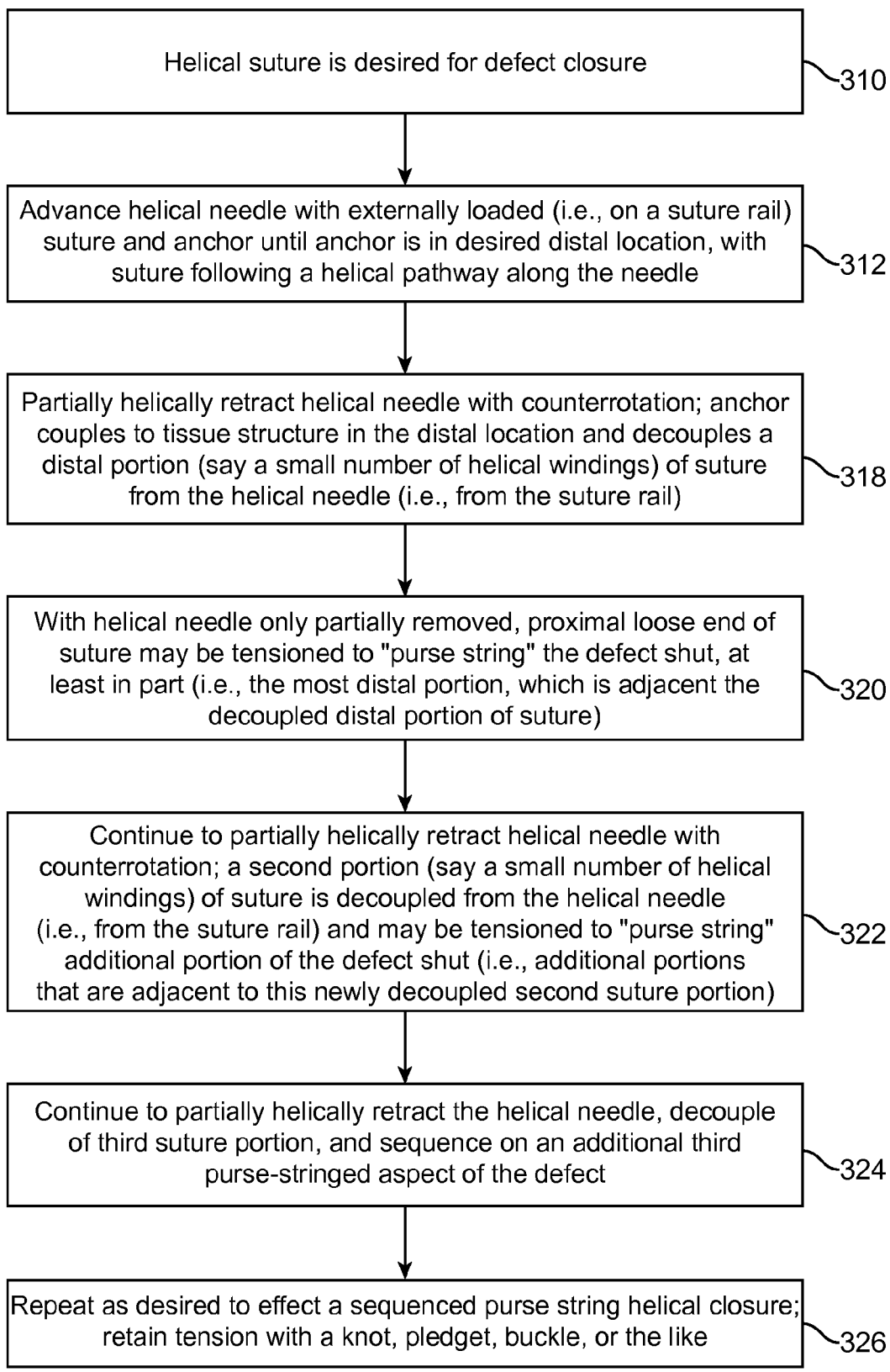
Figure 18C:
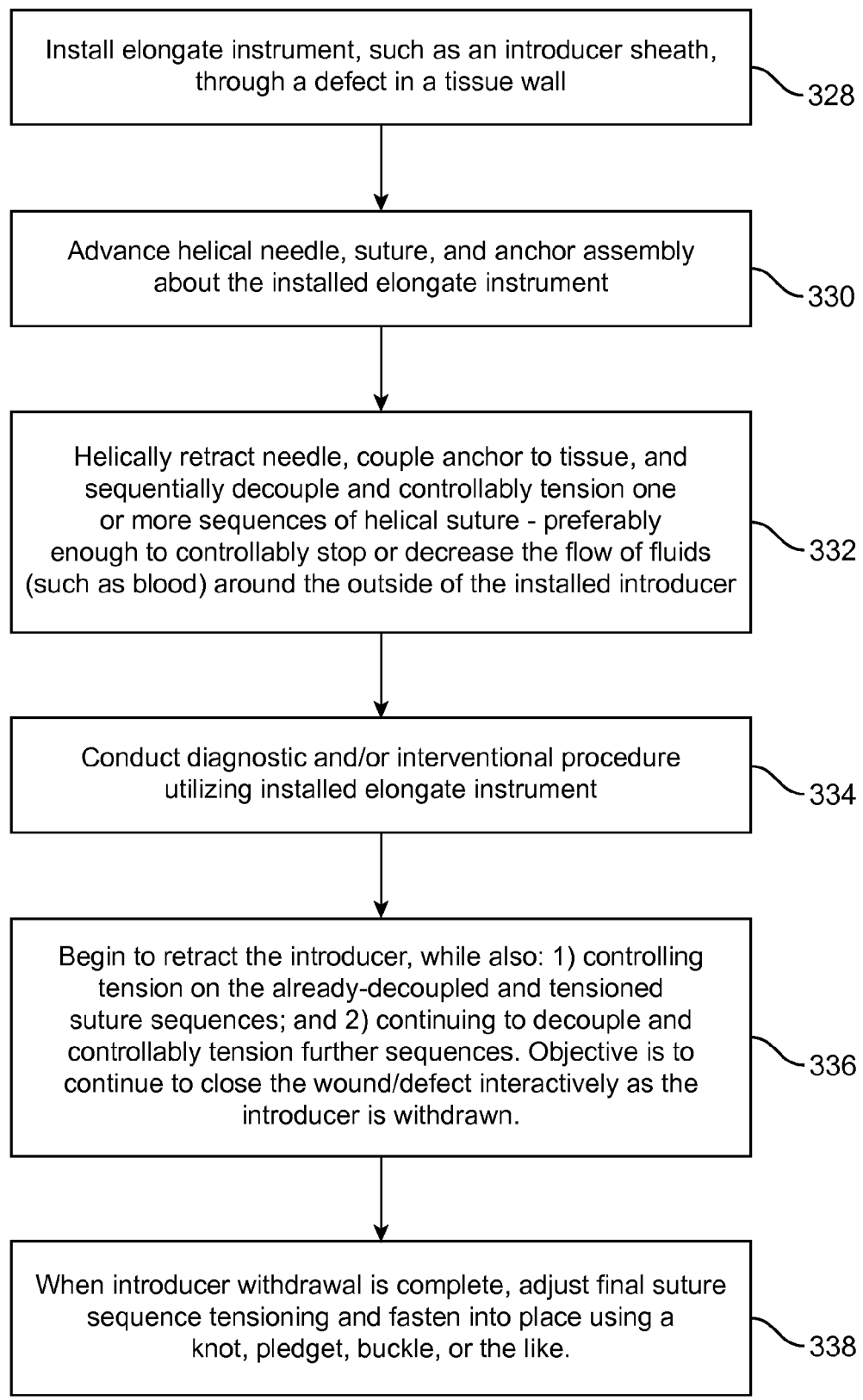

Referring to FIG. 18B, in another embodiment, after a similar two steps (310, 312), the helical needle may only be partially retracted (318), followed by a proximal tensioning to place this first portion of helically deployed suture into tension (320). Then a pledget or other tension-retaining member may be advanced into place, and the process of tensioning the next proximally adjacent helical suture sequence (322) may be conducted—and repeated (324) as necessary to effectively form a serial chain of tensioned helical sutures which may ultimately be proximally fastened to retain tension (326). Such a configuration may be utilized to provide a very robust helical tightening and wound closure. Referring to FIG. 18C, a similar sequential tightening may be utilized around an elongate instrument, such as an introducer, to prevent leakage during use, and to close sequentially after use. As shown in FIG. 18C, an elongate instrument may be installed, creating a defect in a tissue structure (328). A helical needle and suture assembly may be advanced over the elongate instrument (330) and tensioned to prevent leakage around the instrument during use (332). After conducting a diagnostic and/or interventional procedure with the elongate instrument (334), the instrument may be sequentially withdrawn as the helical suture is also sequentially tightened—both around the portions of the instrument still in place, and also to bring the tissue into apposition/closure in the places where the instrument has been withdrawn away (336). The sequence may be repeated until the defect is closed and the suture fastened in place to retain tension.

Figure 19A:
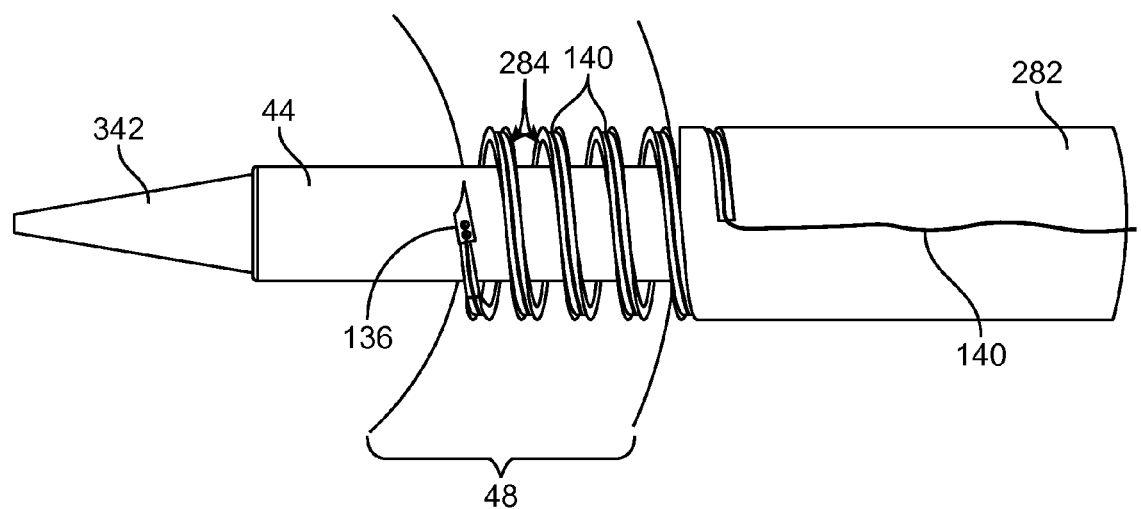
FIGS. 19A-19G illustrate aspects of a deployment process utilizing a helical needle assembly.
Figure 19B:
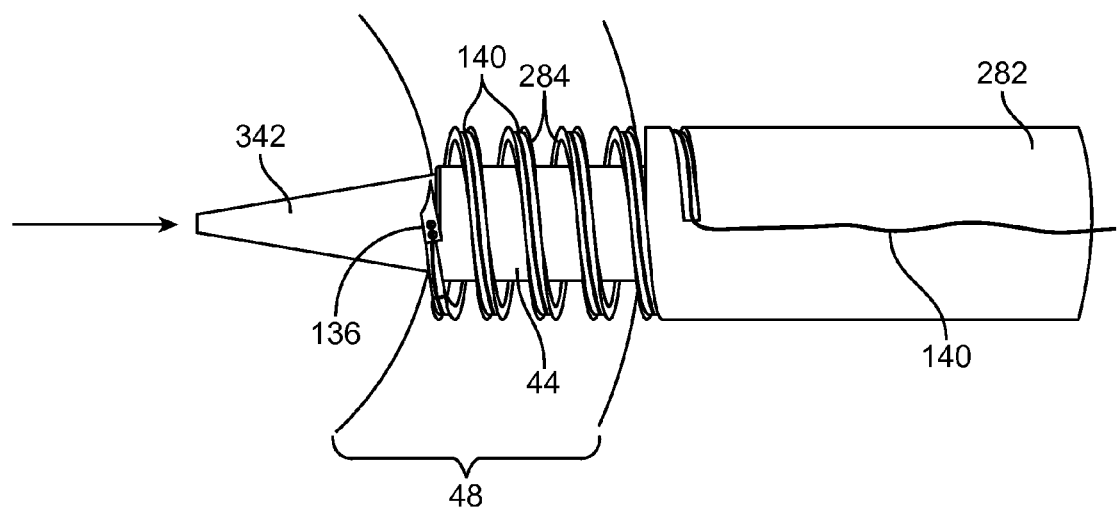
Figure 19C:
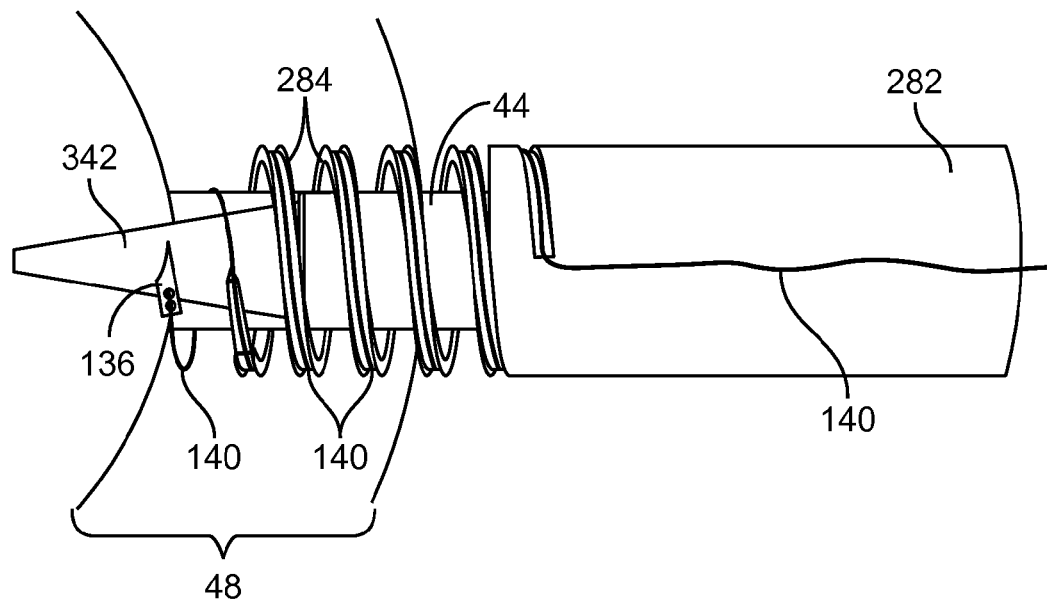
Figure 19D:
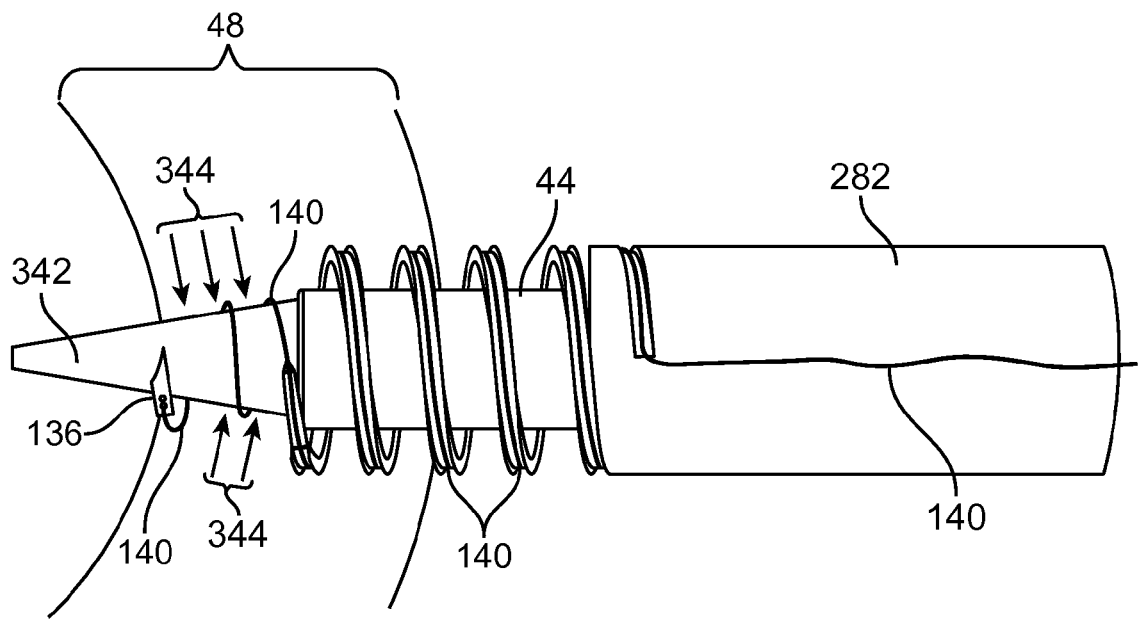
Figure 19E:
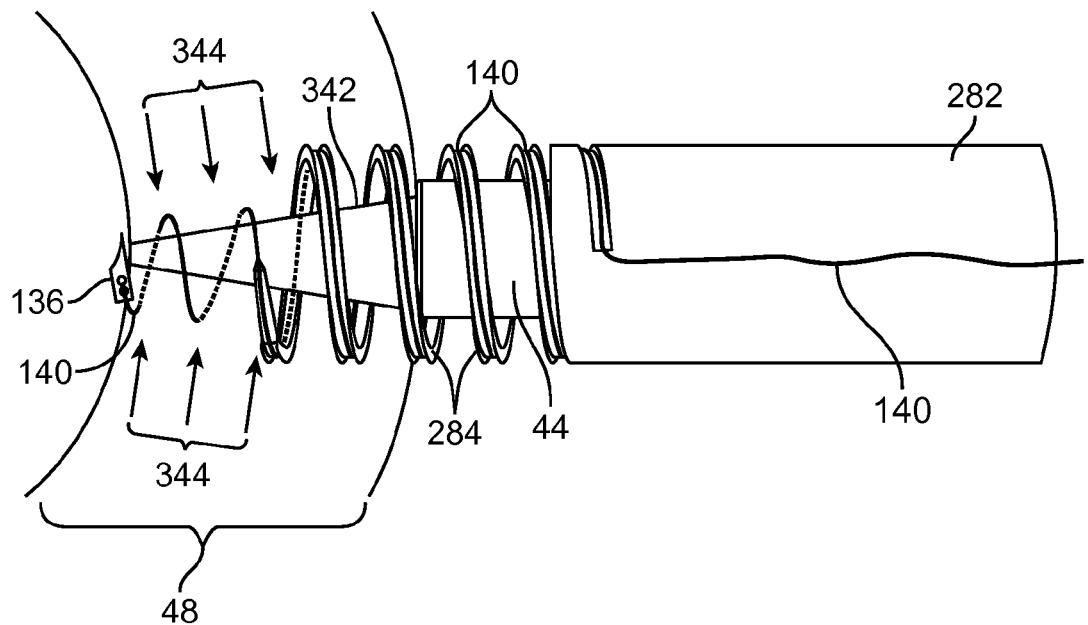
Figure 19F:
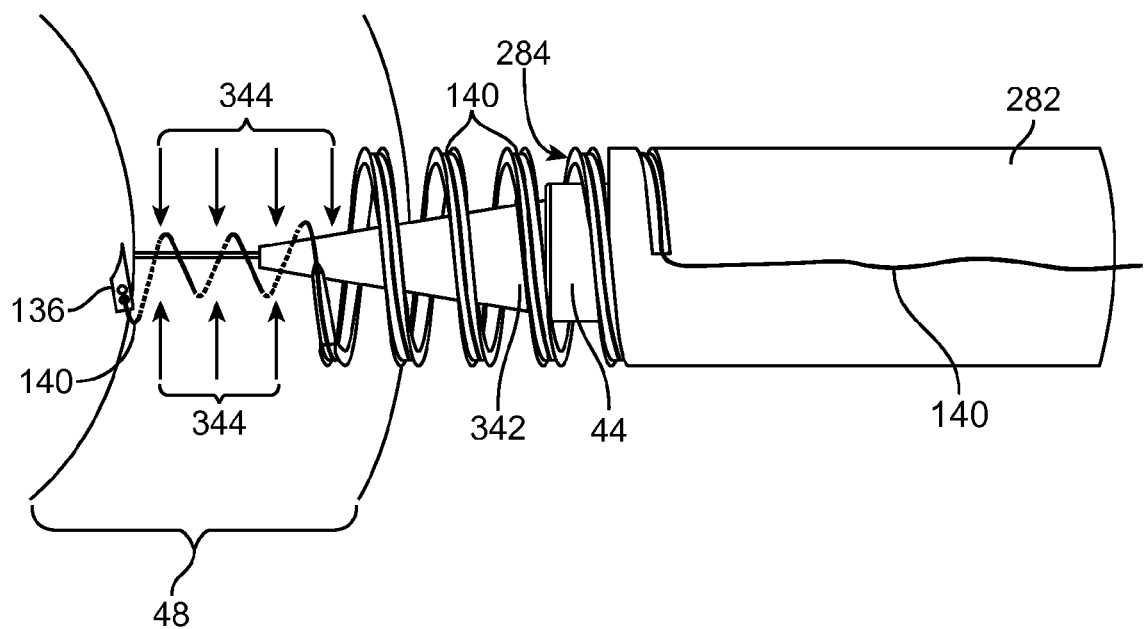
Figure 19G:
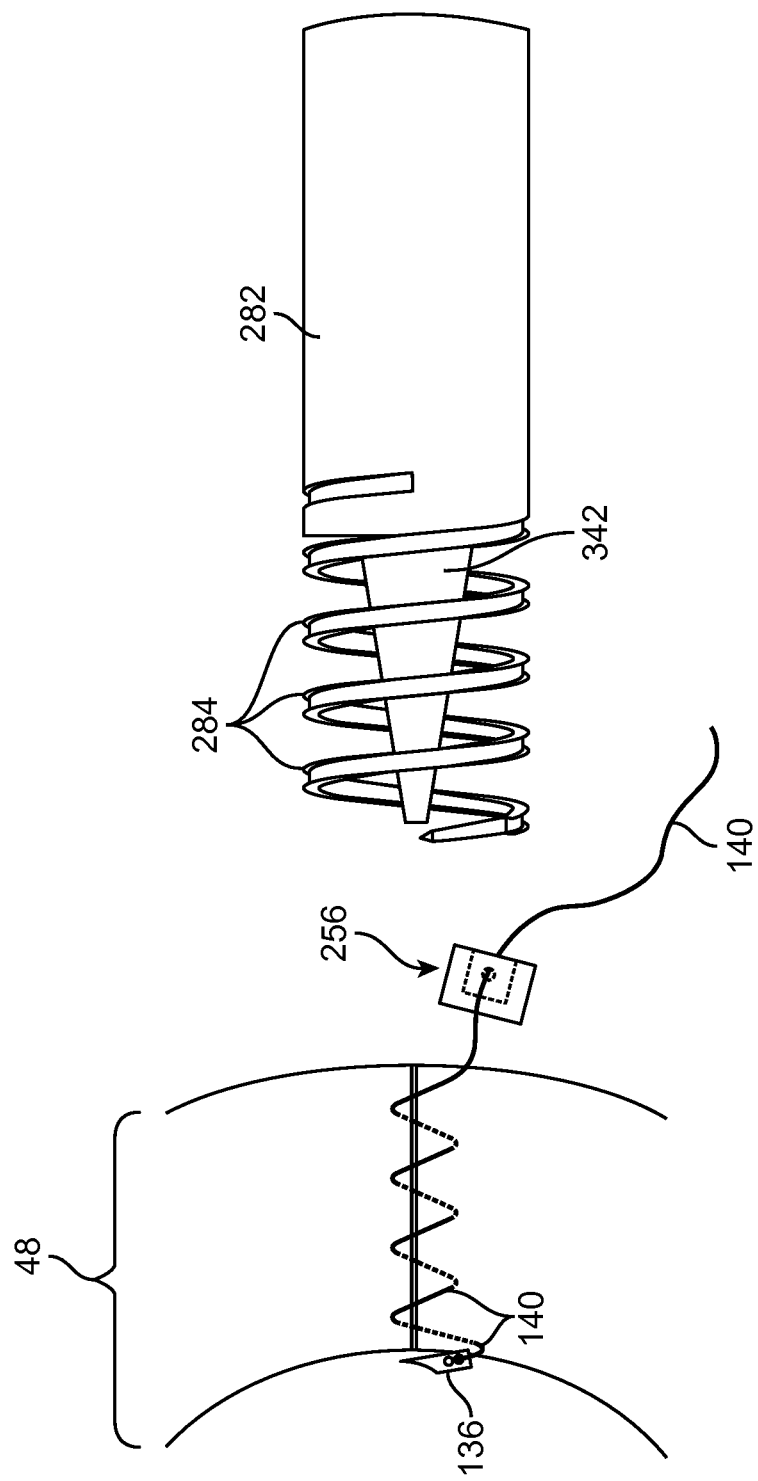

Referring to FIGS. 19A-19G, a helical suture deployment is depicted around a wound formed by insertion of an introducer (44) and dilator (342) instrument set. Referring to FIG. 19A, a dilator (342) is shown inserted through the working lumen of an introducer catheter (44), both of which are inserted through a tissue structure wall such as a left ventricular wall (48). As described above, a helical needle coupler (282) has been rotatably inserted across the wall as well (i.e., over the introducer 44) to position an anchor member (136) carried at the distal end of the helical needle (284) across the ventricular wall (48). An elongate suture member (140) extends proximally from the anchor member (136), around a helical pattern formed in a recess (140, in the depicted embodiment having a "U" or half-circle cross sectional shape that runs helically with the needle shape, as depicted) in the helical needle (284), and then proximally to a position wherein it may be manually manipulated either proximal or distal to the chest wall access port. Referring to FIG. 19B, an operator has started to withdraw the introducer/dilator assembly (44, 342), leaving the helical needle assembly in place. Referring to FIG. 19C, withdrawal of the introducer/dilator assembly (44, 342) is continued, and the operator begins to helically back out the helical needle (284) with the needle coupler (282) or other coupled member, while continually letting out slack in the suture member (140) to allow the distal anchor member (136) to remain in place. Referring to FIG. 19D, continued rotational backing out of the helical needle (284), withdrawal of the introducer/dilator assembly (44, 342), and provision of slack in the suture member (140) enables the compressed viscoelastic tissue to compress (344) the wound shut as the bulk of the instrumentation exits. As described in reference to FIGS. 18B and 18C, the slack may sequentially be taken out and the suture member (140) tensioned to form series purse-string tensioning configurations within the deployed suture member (140). For example, referring to FIG. 19E, with further withdrawal of the helical needle (284) and introducer/dilator assembly (44, 342), tension may be applied in the suture member (140) to create a purse string effect in the one or two most distal loops of the suture (immediately adjacent the anchor member 136), and with a let-up in tension, slack reforms in the most proximal helical loops, but the most distal loops retain the purse string type tension. Referring to FIG. 19F, this may be repeated after further withdrawal of the helical needle (284) and introducer/dilator assembly (44, 342) to purse-string-close the next set of loops immediately proximal to the previously tensioned loops. Further repetition may be utilized to create a very robust closure, as depicted in FIG. 19G, wherein after complete withdrawal of the helical needle (284) and introducer/dilator assembly (44, 342) from the wall (48), a suture buckle assembly (256) may be advanced to retain tension of the deployed and tightened helical suture member portions, as described, for example, in reference to FIG. 16E.

Referring to FIGS. 20A-22K, embodiments are depicted wherein an expandable or inflatable member may be utilized to assist with leak prevention around the outside of a deployed introducer or other similar member. Such device may further be utilized to assist in closure of the associated wound or defect, as described in reference to FIGS. 22E-22K.

Figure 20A:
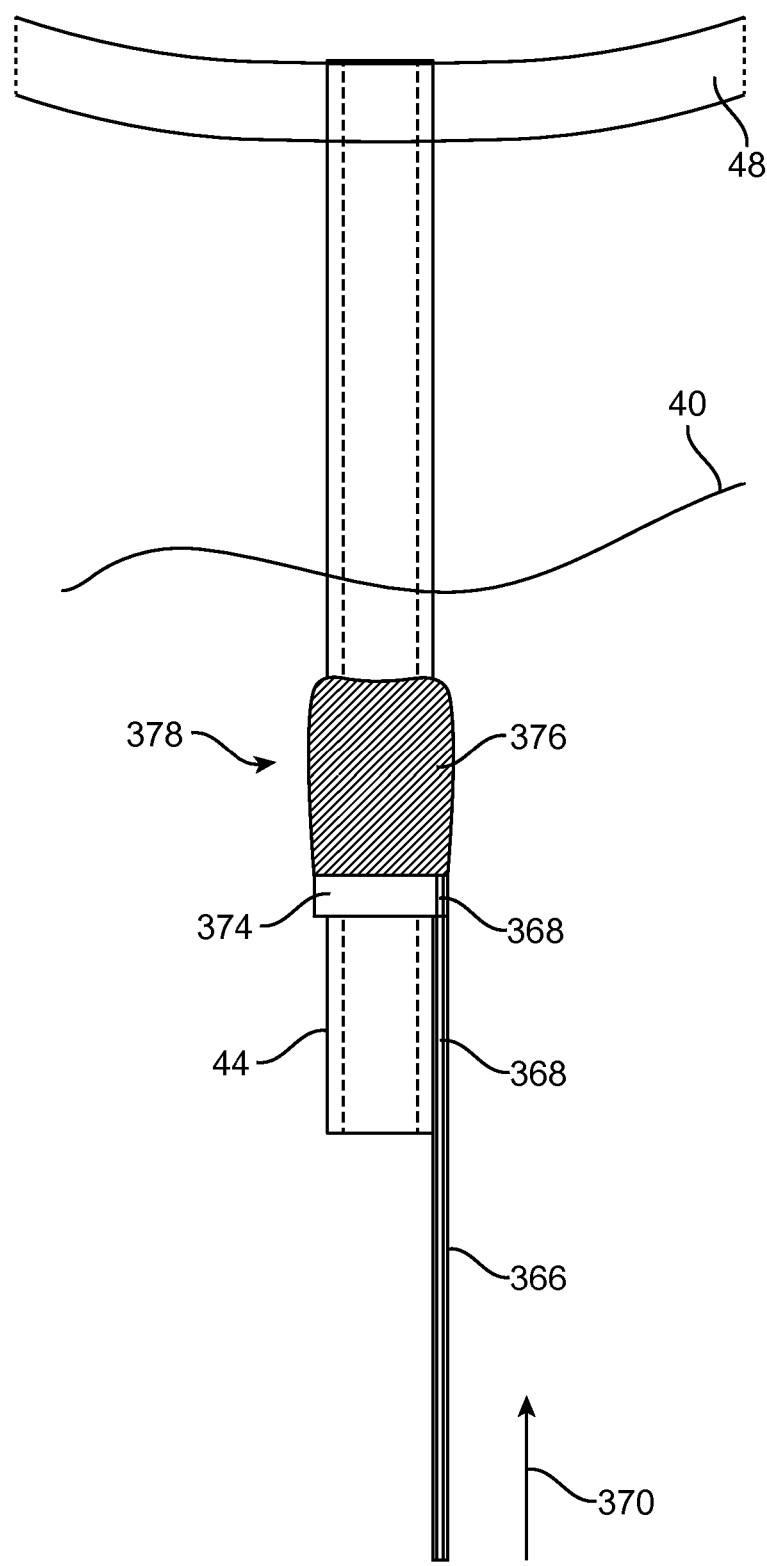
FIGS. 20A-20G illustrate aspects of a leak prevention assembly deployment wherein an inflatable member may be utilized to prevent leakage around an intersection of an introducer or similar member and a tissue wall.
Figure 20B:
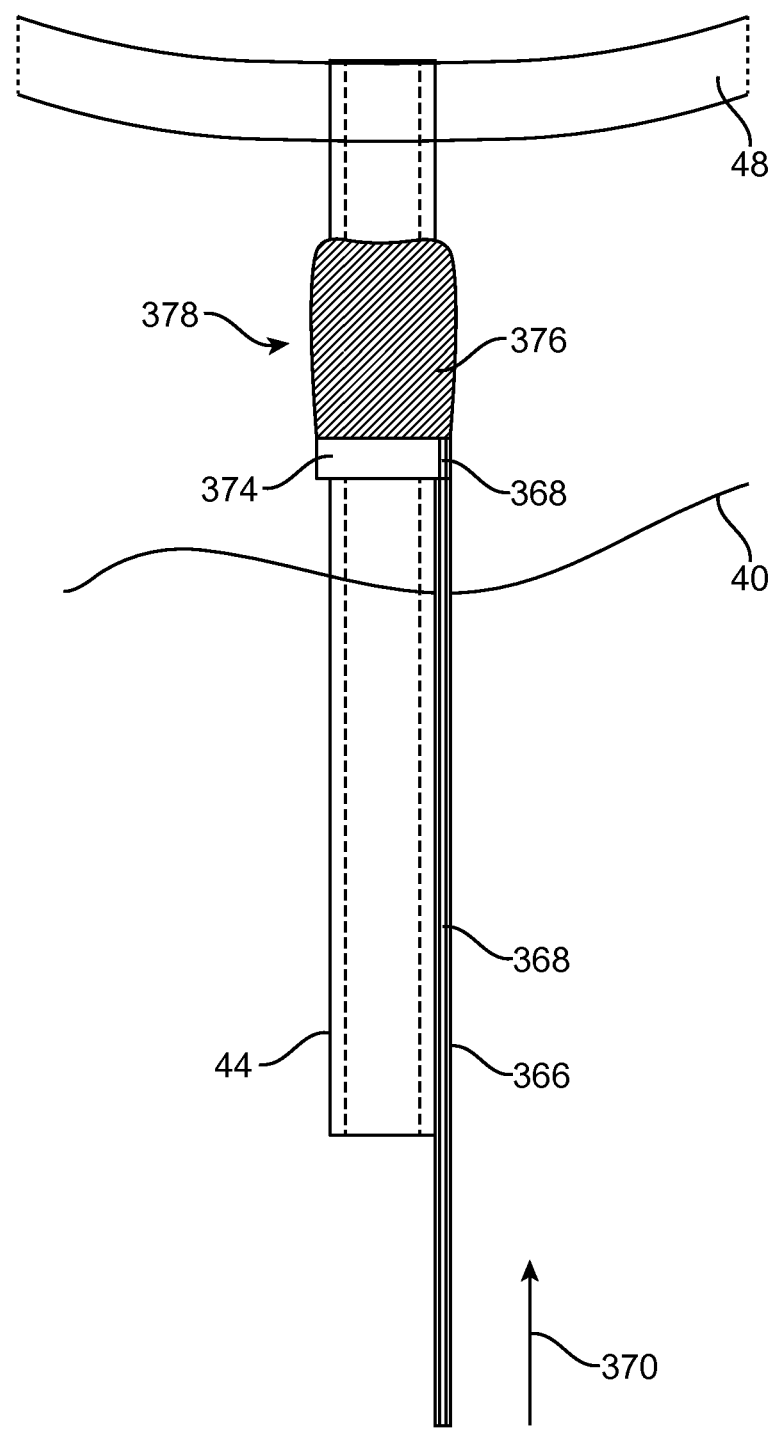
Figure 20C:
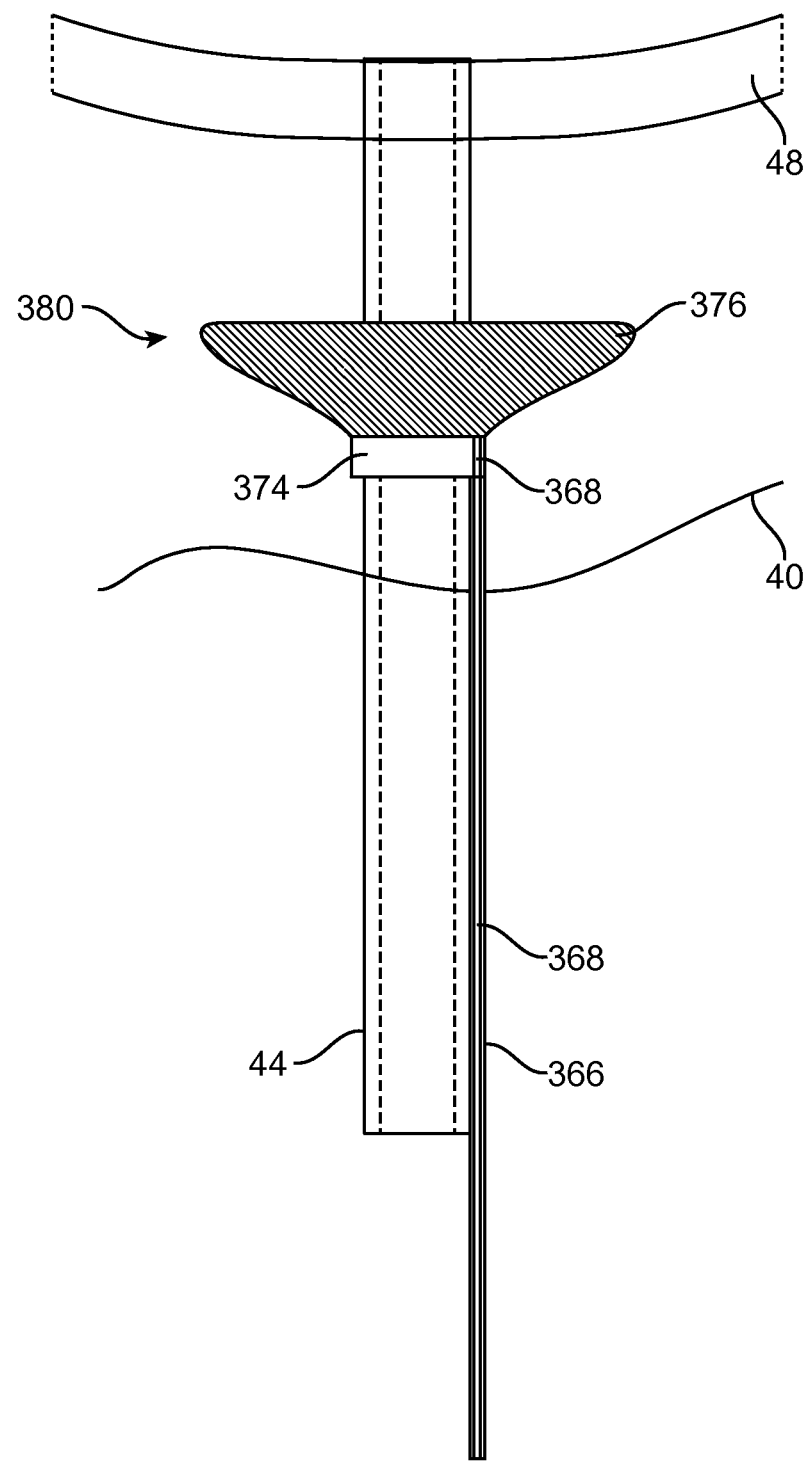
Figure 20D:
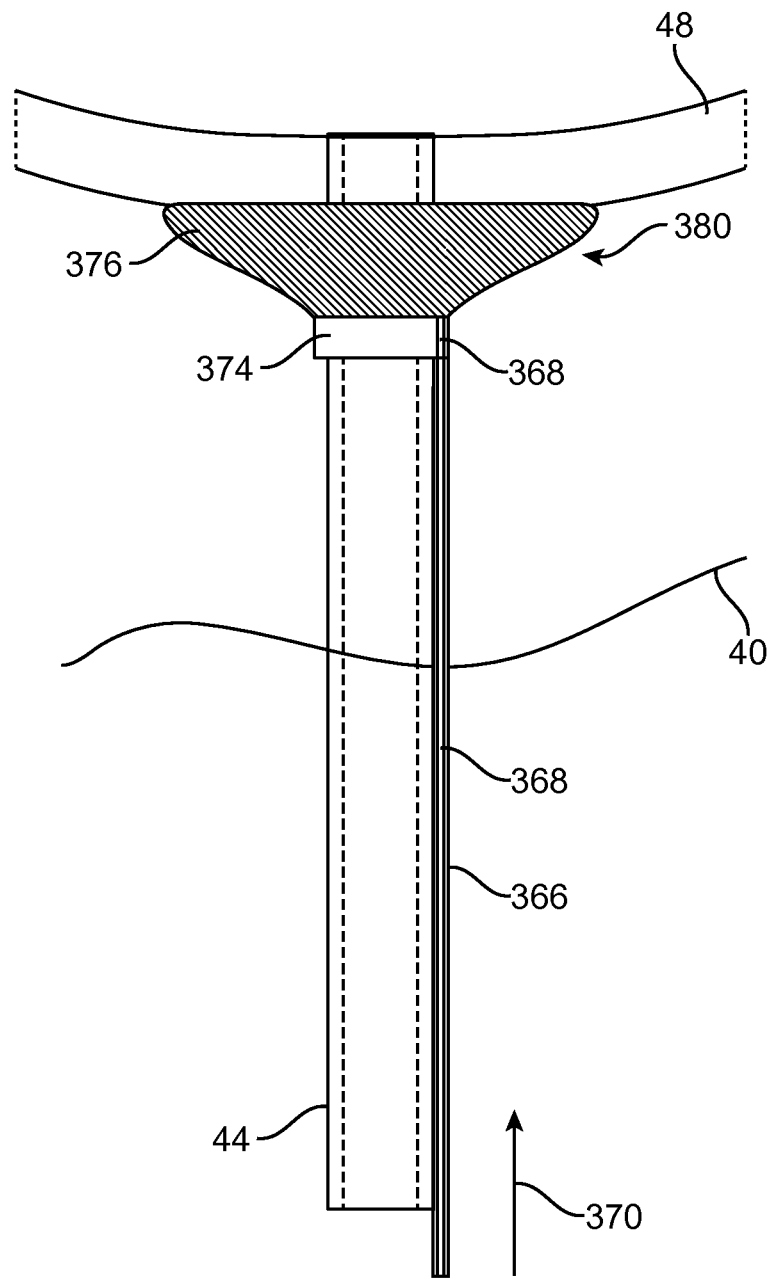
Figure 20E:
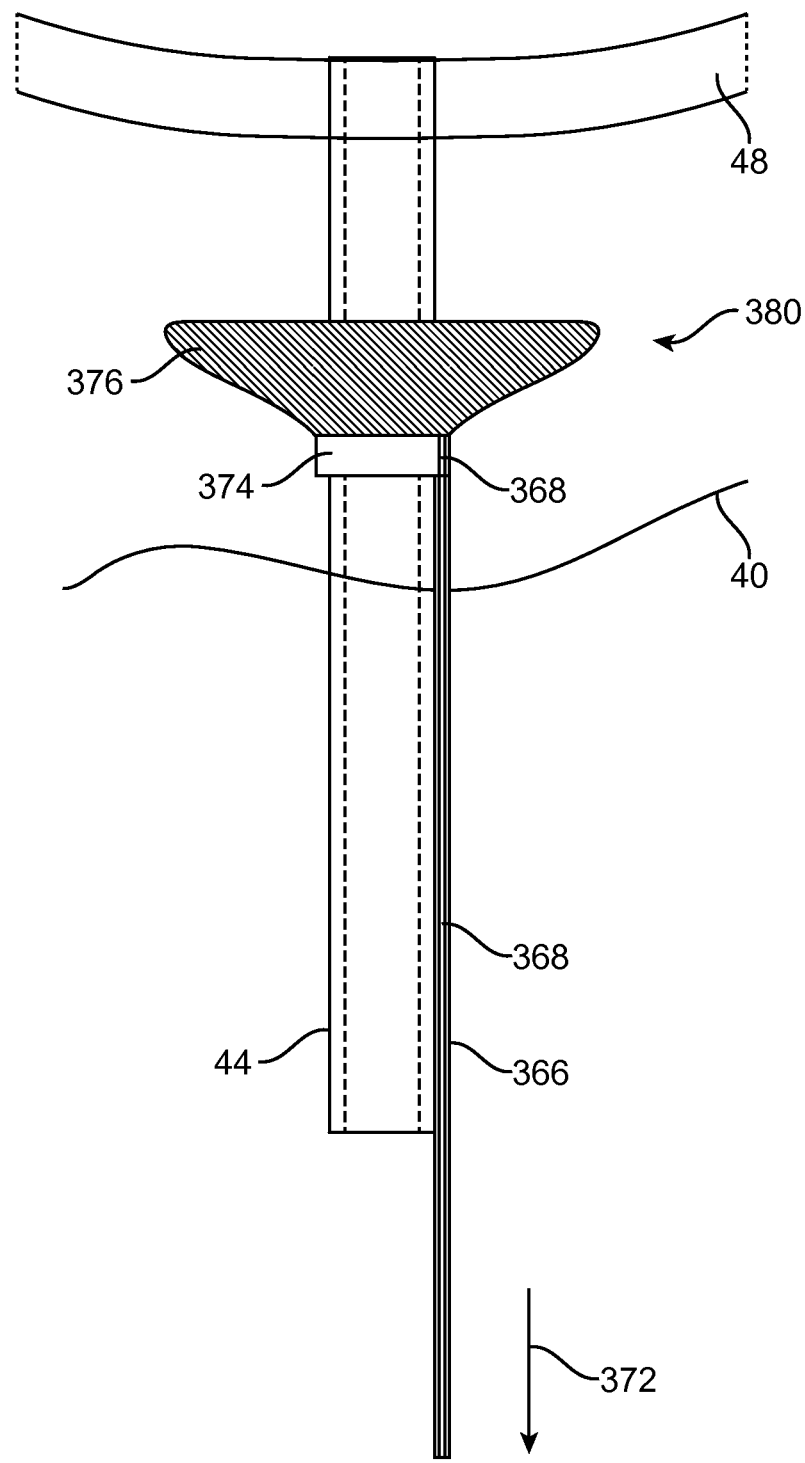
Figure 20F:
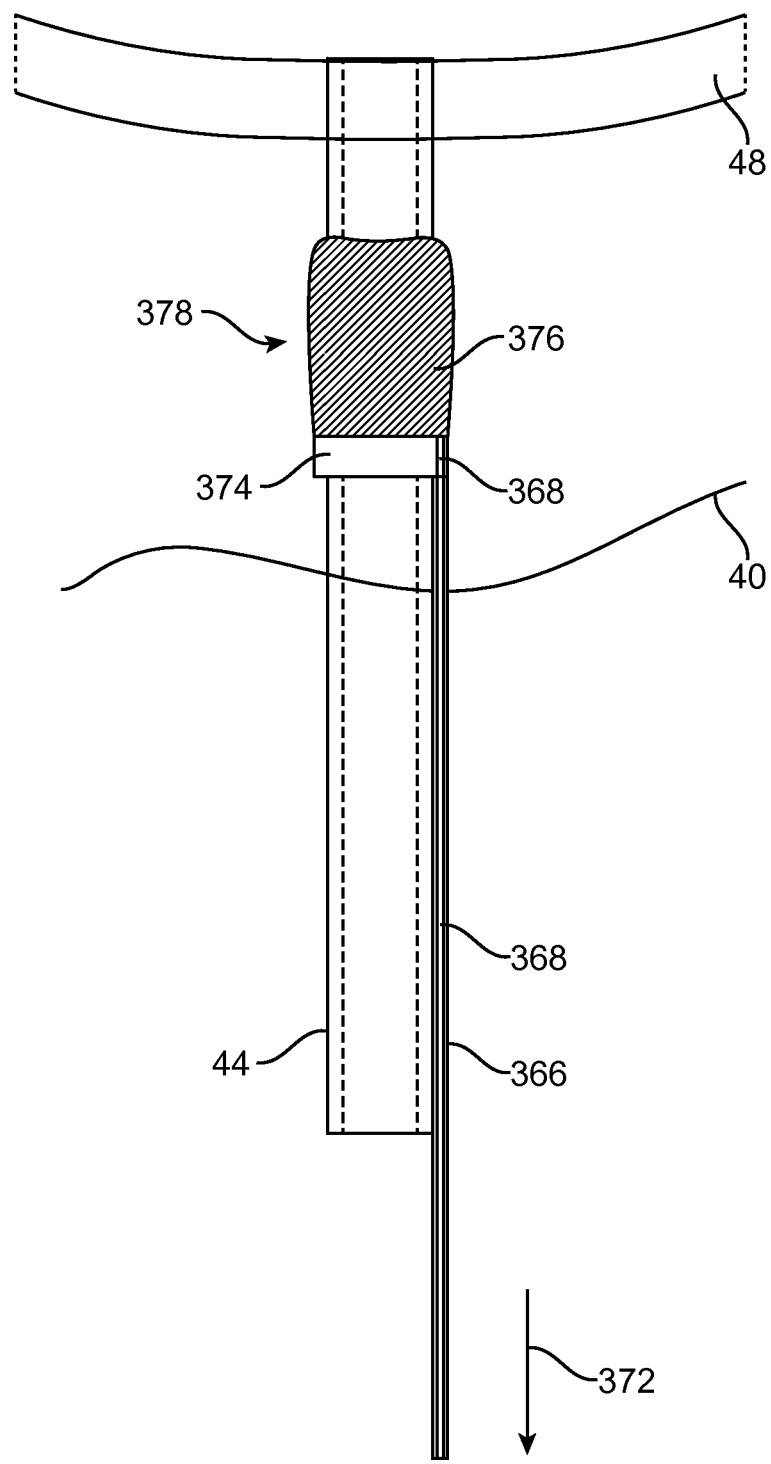
Figure 20G:
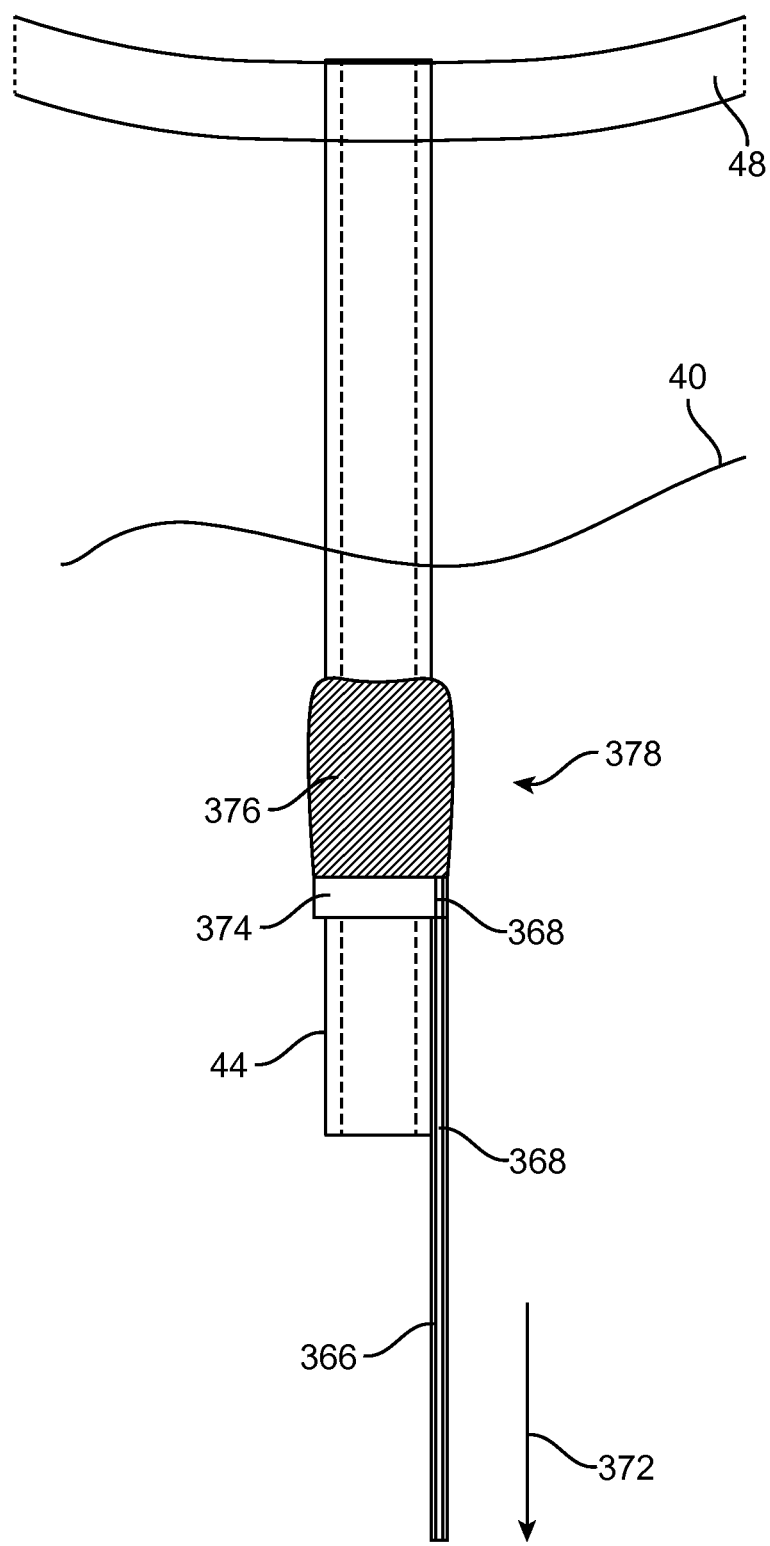

Referring to FIG. 20A, to prevent fluid leakage at the interface between a deployed introducer (44) or other similar structure and a left ventricular wall (48) or other similar structure, an inflatable member (376) coupled to a rigid proximal collar member (374), which preferably is slidably and rotatably coupled around the outer aspect of the introducer (44), may be advanced (370) over the introducer (44). The proximal collar member (374) preferably is coupled to a structural manipulation member (366) which may comprise an elongate rod or slender structure member, and which preferably defines a lumen (368) therethrough which preferably extends through the proximal collar (374) to the inflatable member (376) to facilitate controlled inflation of the inflatable member (376), which may comprise a balloon or similar bladder construct configured to have a collapsed configuration (378), such as that depicted in FIG. 20A, and an expanded configuration (380), such as that depicted in FIG. 20C. The proximal end of the manipulation member may be manipulated manually by the operator, or may be coupled to another member which may be so manipulated, to control insertion, inflation, and roll rotation of the inflatable member (376) and collar member (374) relative to the introducer (44). Referring to FIG. 20B, the assembly has been further inserted (370) relative to the introducer and tissue structures with the inflatable member (376) in a collapsed state (378) to more easily cross the chest wall (40) access port. Referring to FIG. 20C, the inflatable member (376) has been inflated using the inflation lumen (368) to its expanded state (380), which resembles a compliant frustoconical shape, as illustrated. Referring to FIG. 20D, the expanded (380) inflatable member (376) may be urged against the intersecting introducer (44) and tissue wall (48) region to prevent leakage of fluids such as blood past such intersection. Referring to FIG. 20E, the assembly may subsequently be retracted (372), returned to its collapsed expandable member (376) state (378) as in FIG. 20F, and withdrawn (372) in the collapsed state (378), as depicted in FIG. 20G.

Figure 21A:
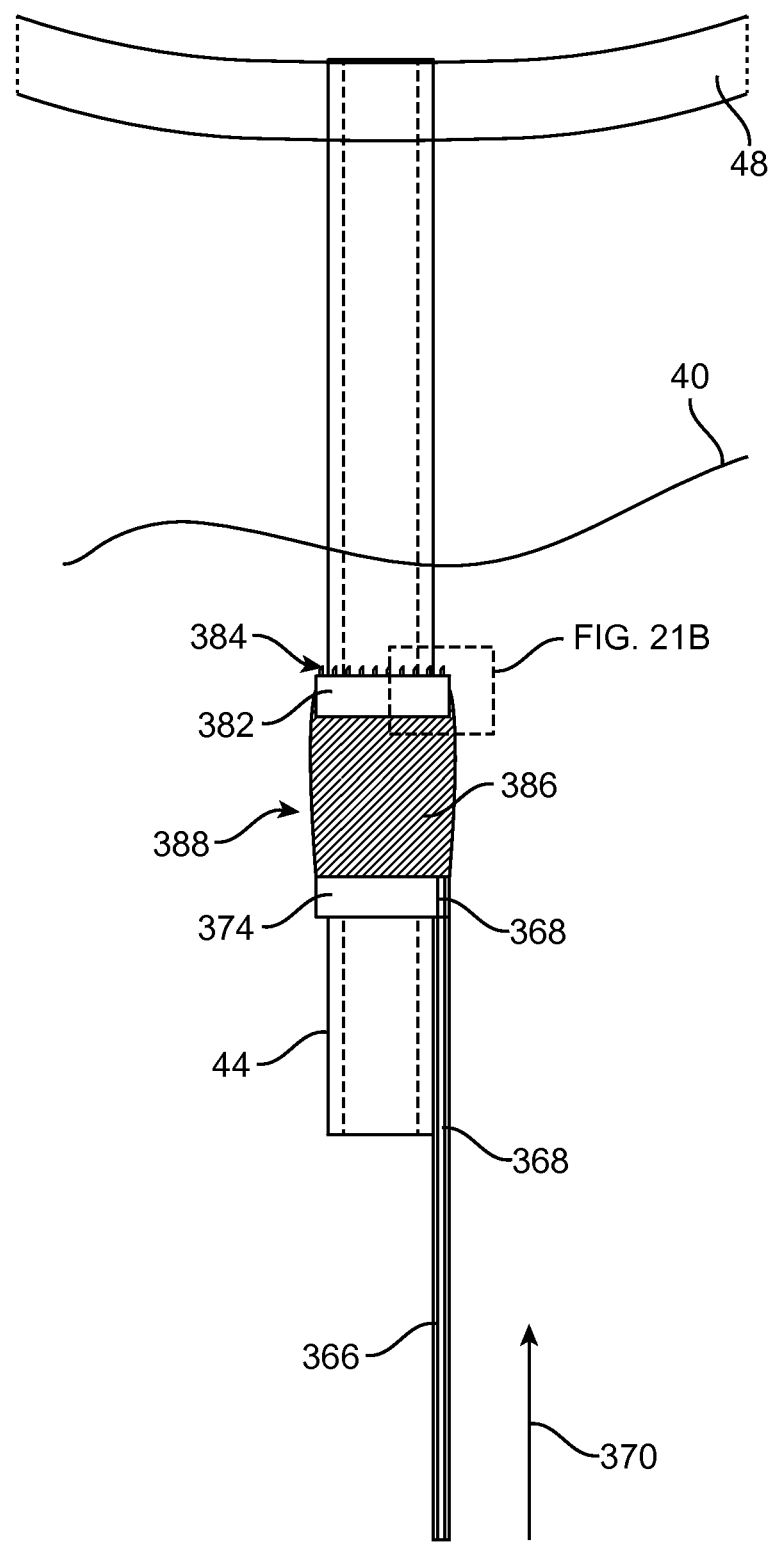
FIGS. 21A-21J illustrate aspects of a leak prevention assembly deployment wherein an inflatable member with distal collar member may be utilized to prevent leakage around an intersection of an introducer or similar member and a tissue wall.
Figure 21B:
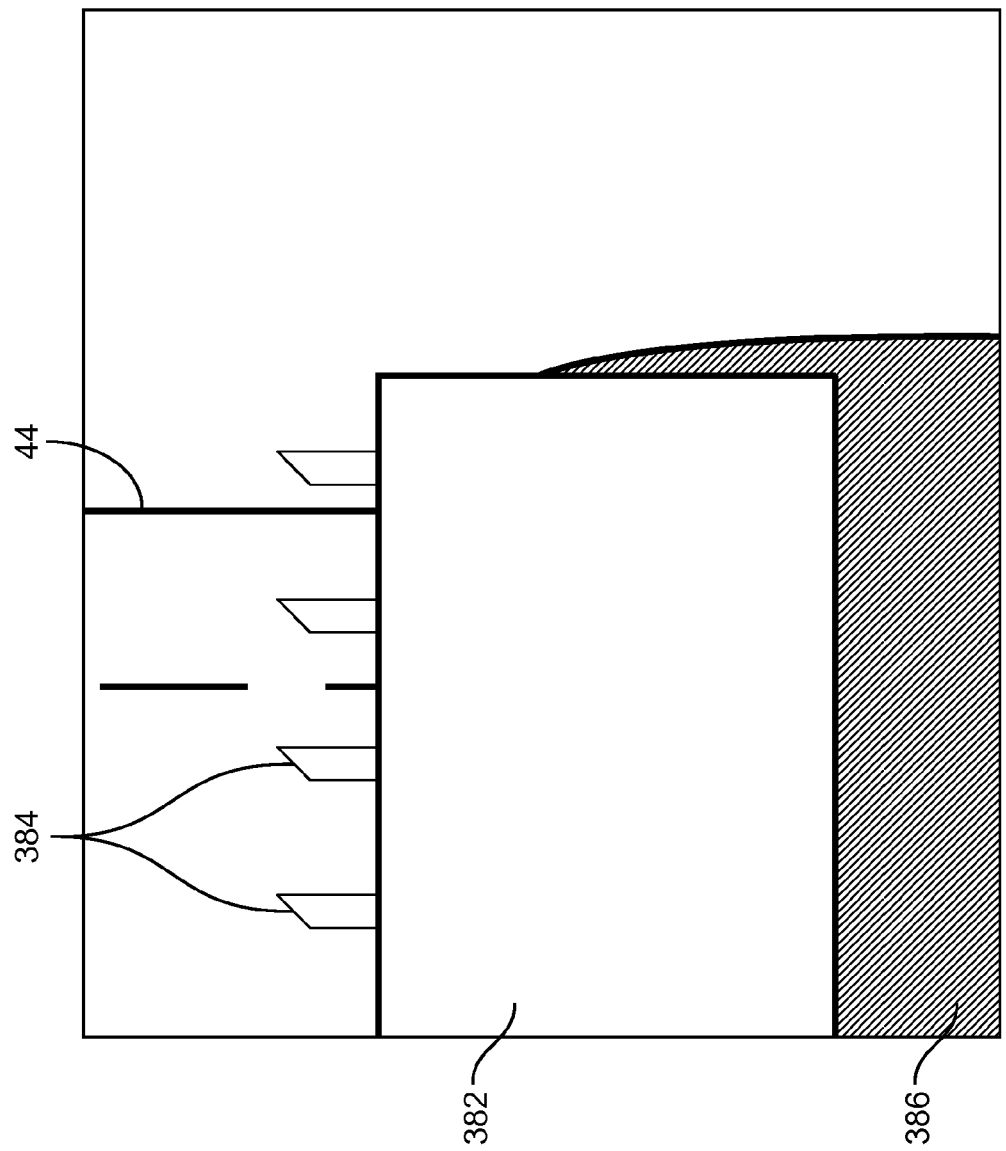
Figure 21C:
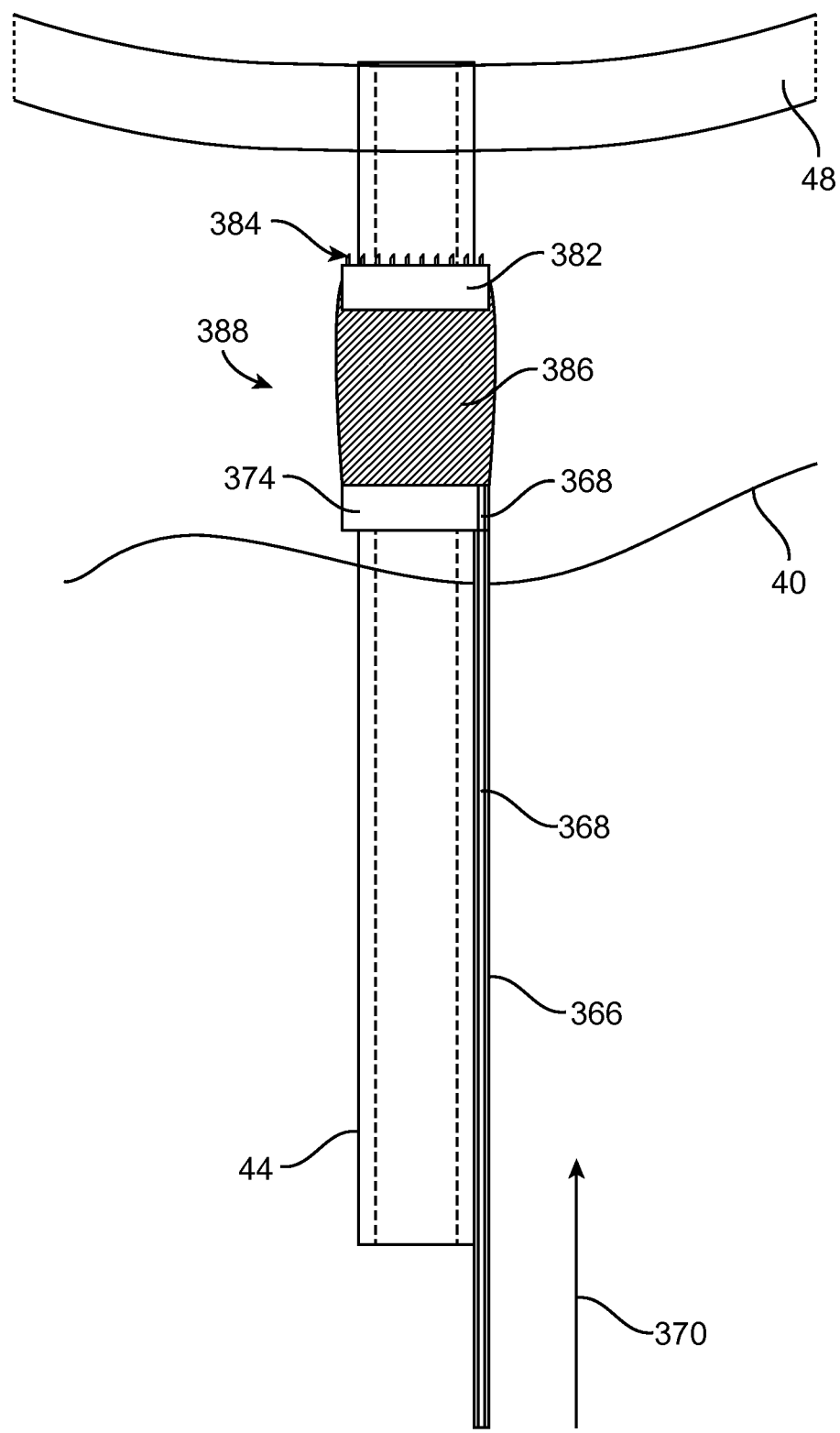
Figure 21D:
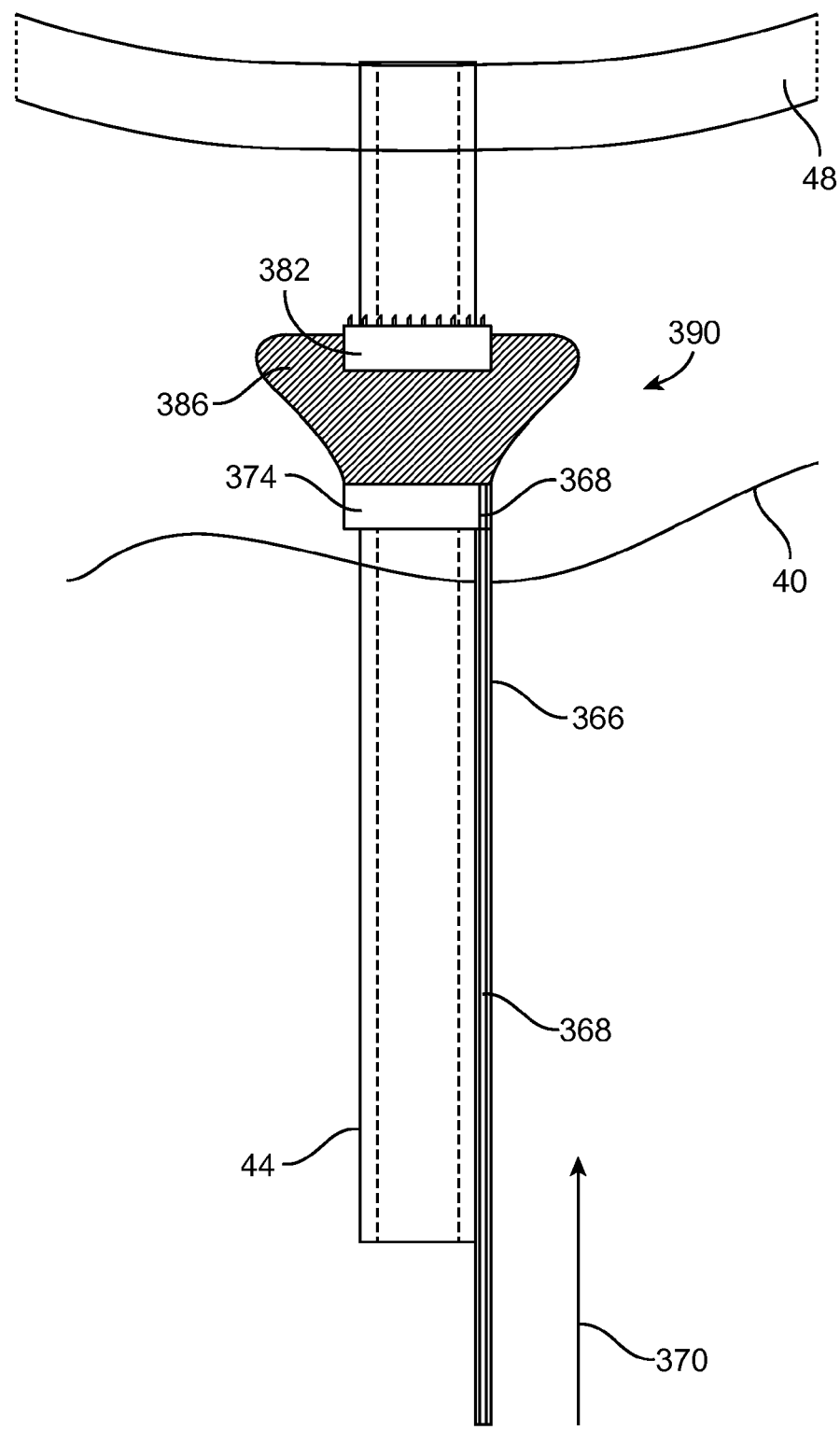
Figure 21E:
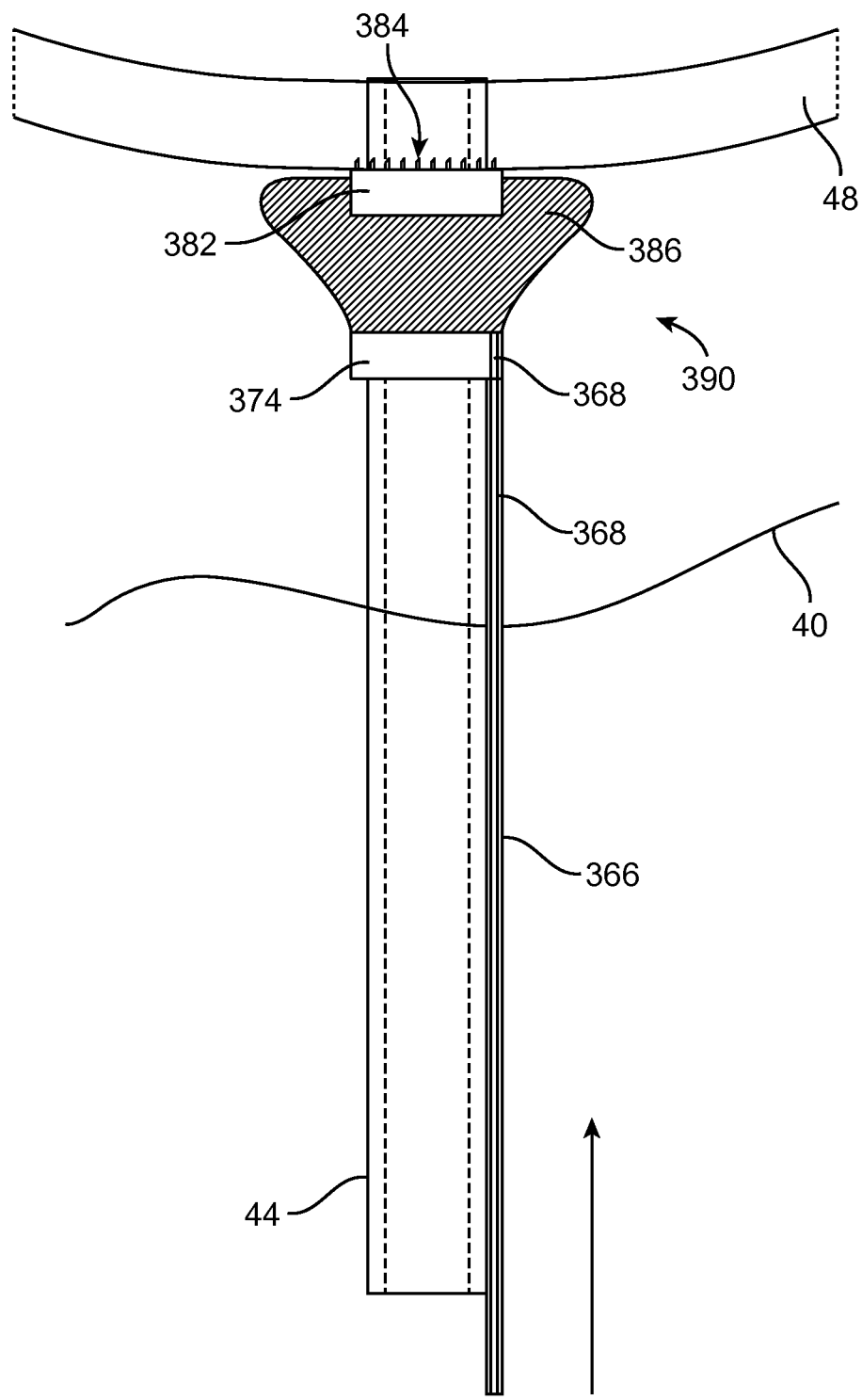
Figure 21F:
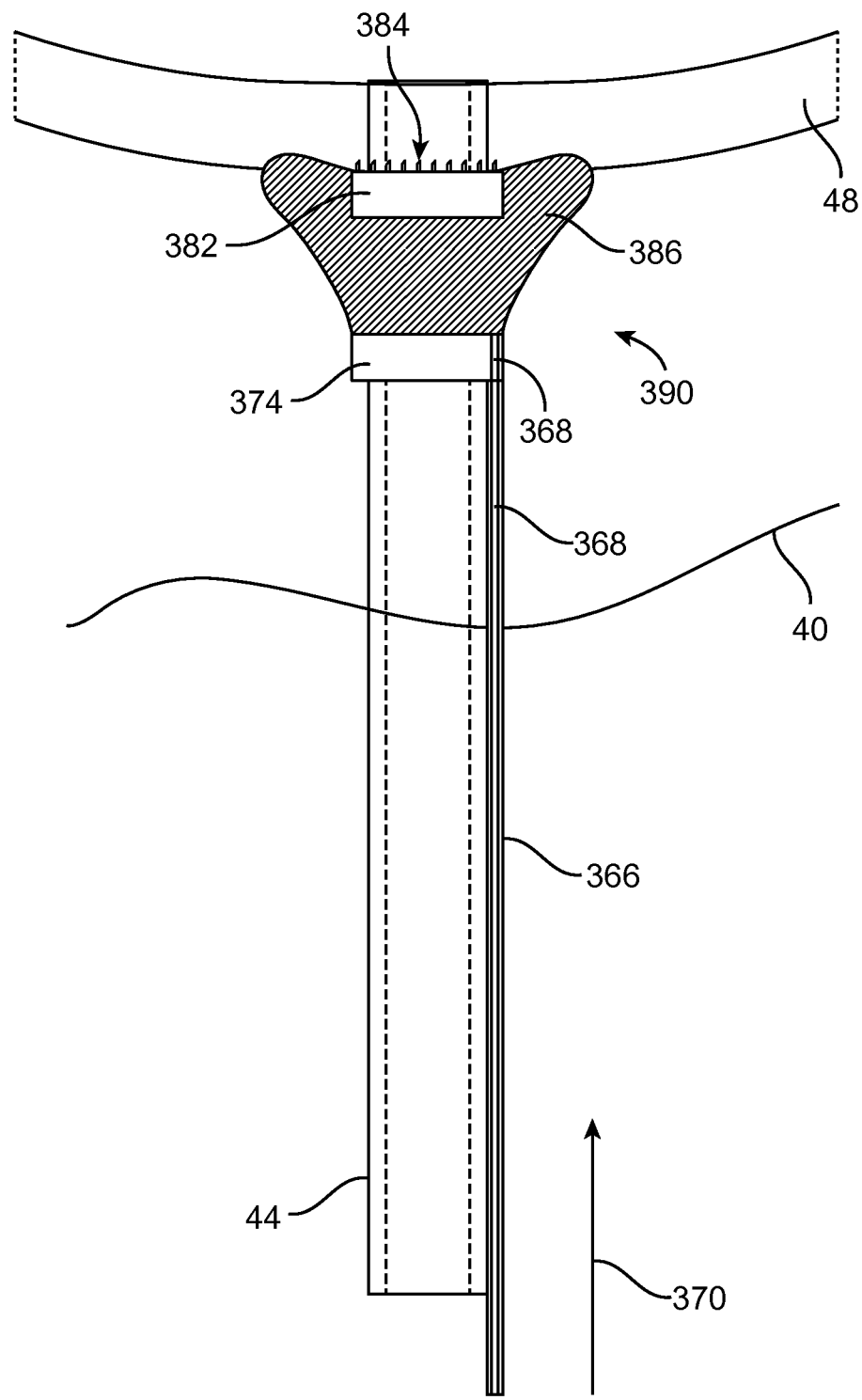
Figure 21G:
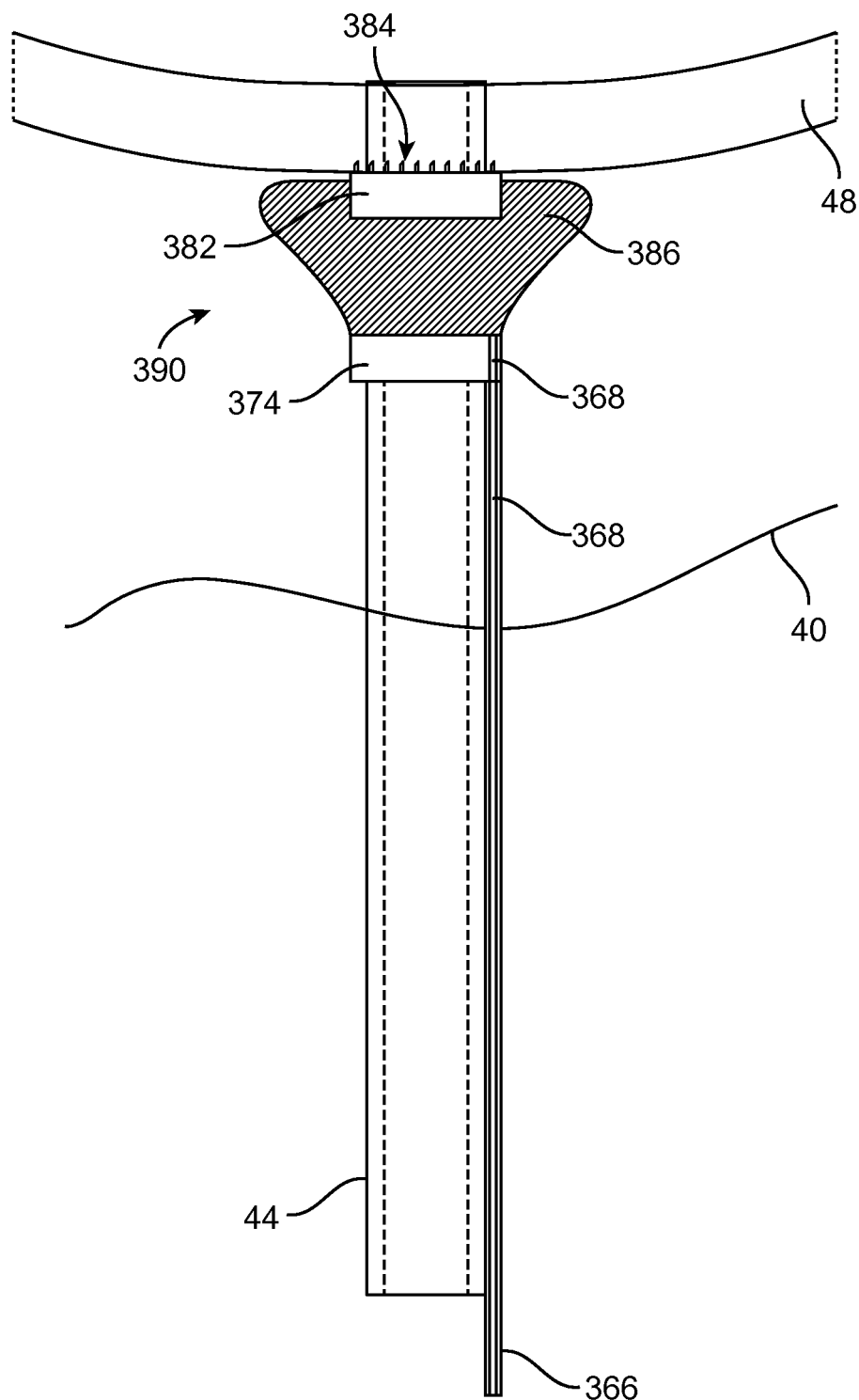
Figure 21H:
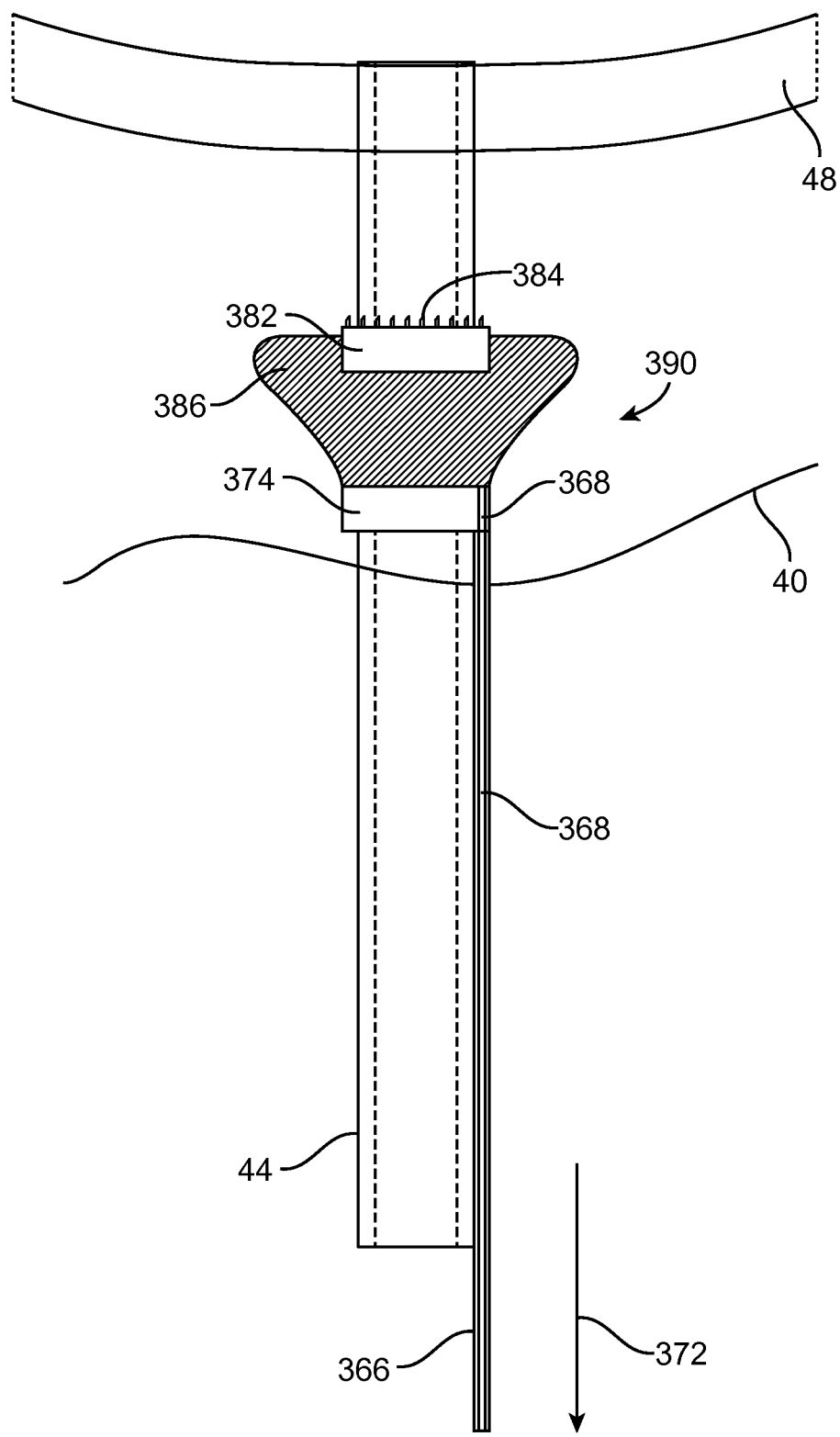
Figure 21I:
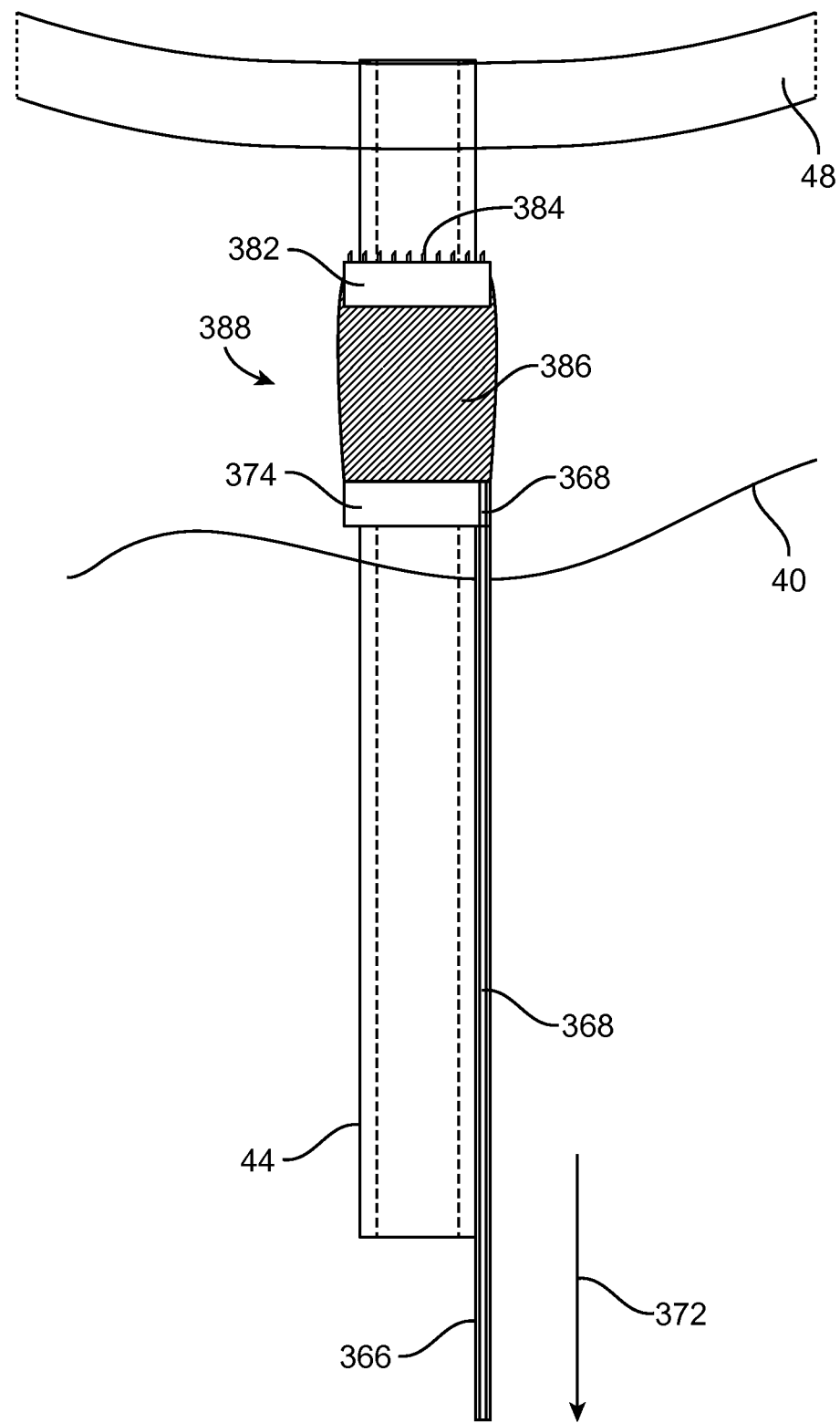
Figure 21J:
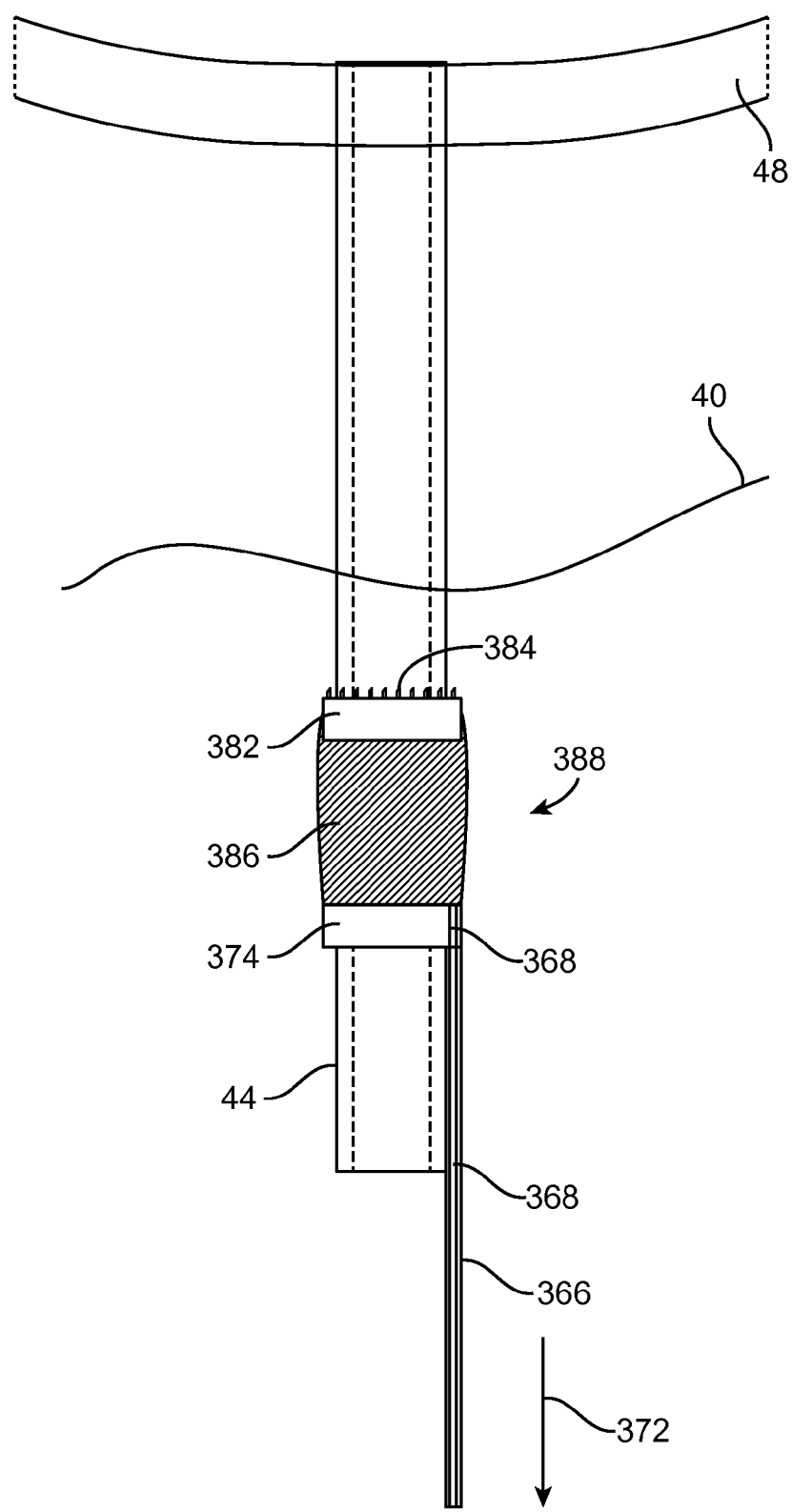

Referring to FIGS. 21A-21J, another embodiment is depicted wherein the wound or defect temporary sealing assistance assembly comprises a distal collar member (382) coupled to the proximal collar member (374) by the inflatable member (386). As with the inflatable member of FIGS. 20A-20G (376), the inflatable member of FIGS. 21A-21J, and the inflatable member of FIGS. 22A-22K may comprise an elastomeric medical balloon type material, such as polyurethane, configured to be quite expandable and malleable when in a final expanded shape, or may comprise a relatively inelastic medical balloon type material, such as polytetrafluoroethylene or polyethylene terepthalate, configured to assume a final shape and not expand much beyond such final shape. Referring to the close-up view of FIG. 21B, the distal collar of the depicted embodiment features a distal surface with small spike-like contact elements (384) configured to prevent slipping between the distal collar surface and tissues against which it is urged. Referring to FIG. 21C, the assembly is advanced across the chest wall (40) in a collapsed state (388). Referring to FIG. 21D, the expandable member (386) may be expanded with inflation through the lumen (368) to the expanded state (390), wherein the expandable member (386) forms a shoulder-like reinforcing shape around the distal collar (382) which is suspended and supported by the expandable member (386). Referring to FIG. 21E, the assembly is further inserted to urge the distal collar member (382) against the tissue surrounding the intersection of the introducer (44) and tissue wall (48) to prevent leakage of fluids, such as blood, around the introducer (44). The contact elements (384) retain the tissue position relative to the introducer (44) and distal collar (382) in such configuration. Referring to FIG. 21F, additional insertion loads and/or inflation of the inflatable member (386) may be utilized to create additional sealing of the intersection between the introducer (44) and tissue wall (48); such additional loading may be pulsed over time to prevent desanguination and/or lysis of any of the associated tissues (FIG. 21G shows the configuration again without the additional loading pulsed on). Referring to FIG. 21H, the assembly may be withdrawn relative to the introducer (44) and tissue wall (48), returned to the collapsed inflatable member state (388) as in FIG. 21L, and withdrawn as in FIG. 21J.

Figure 22A:
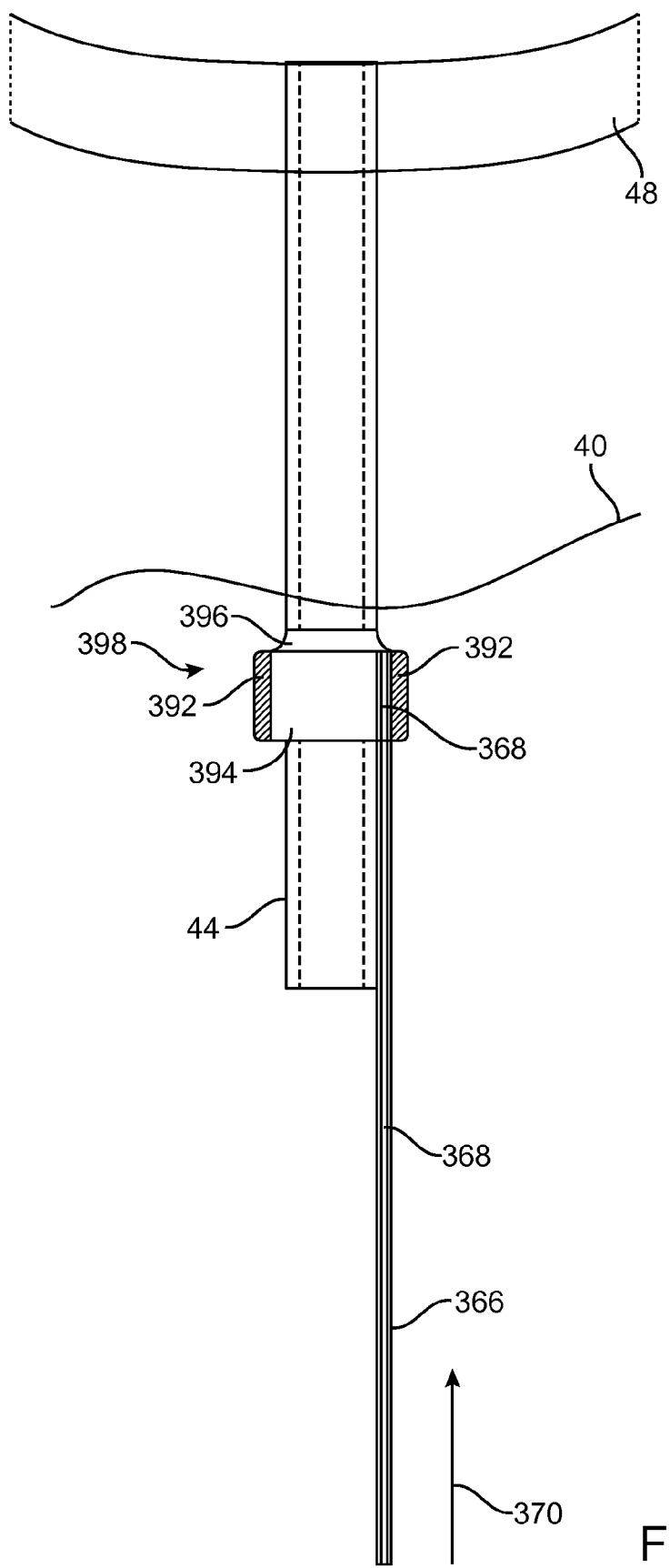
FIGS. 22A-22k illustrate aspects of a leak prevention assembly deployment wherein an inflatable member and tapered distal member may be utilized to prevent leakage around an intersection of an introducer or similar member and a tissue wall, and to close the wound that remains after withdrawal of the introducer or similar member.
Figure 22B:
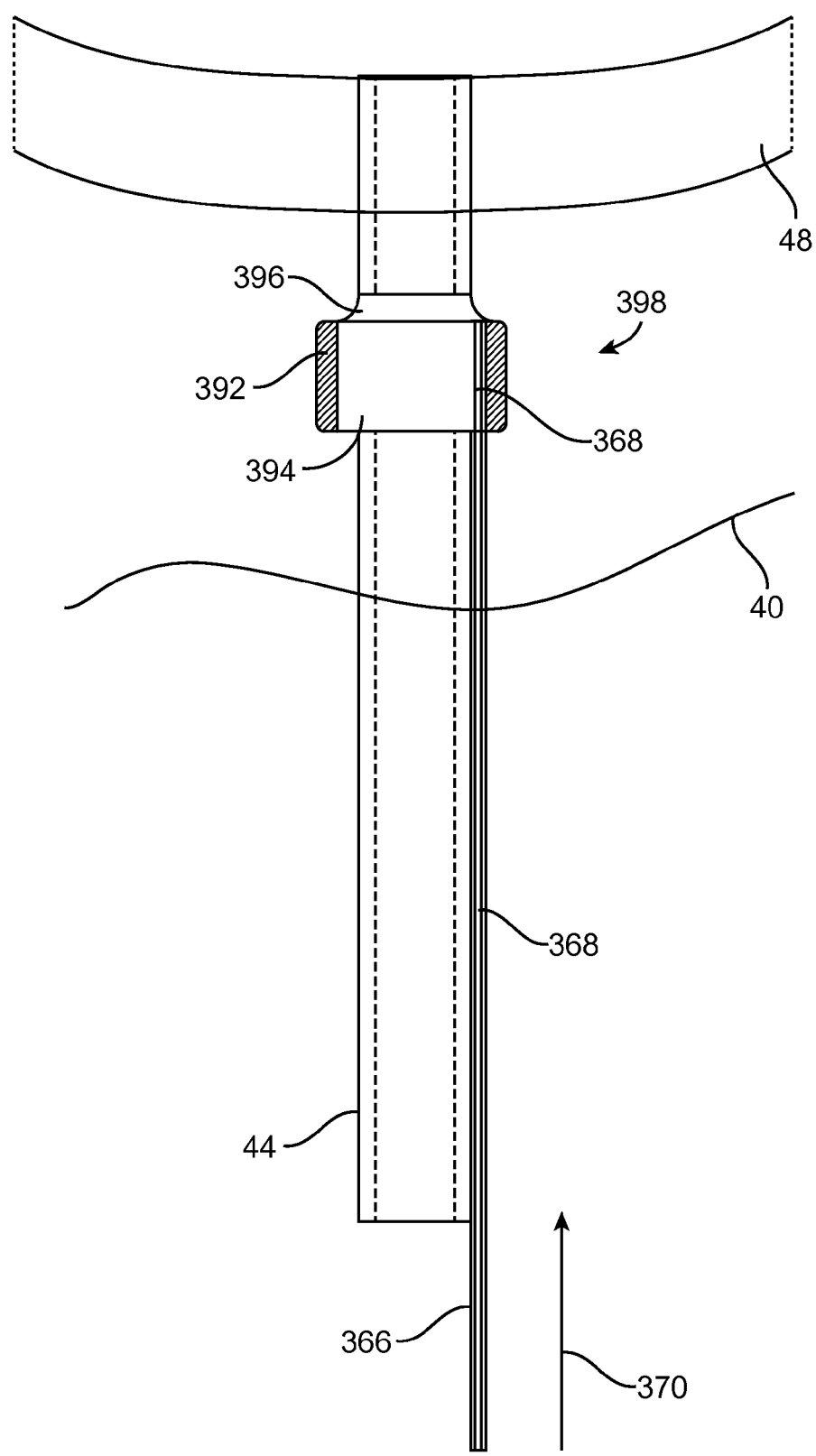
Figure 22C:
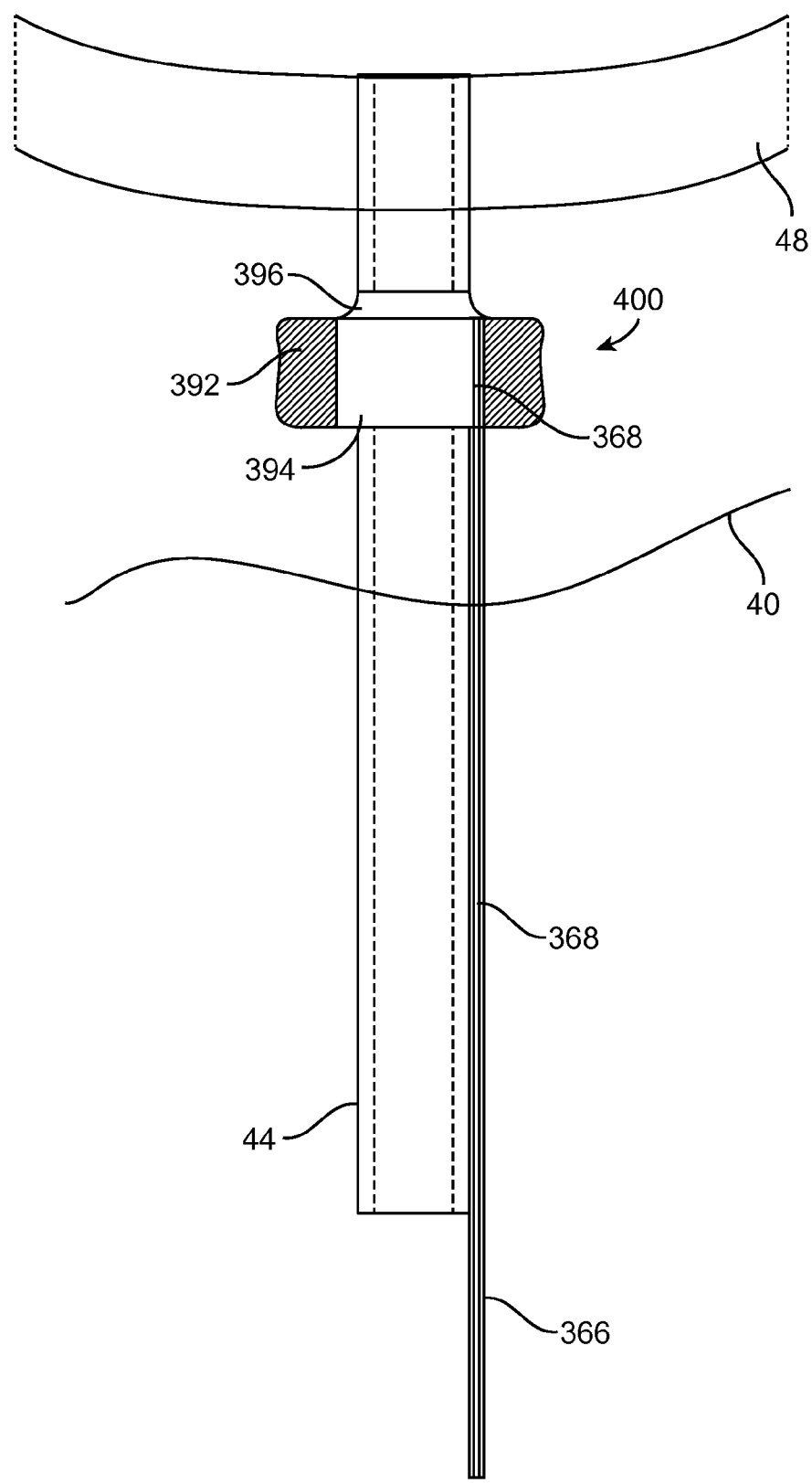
Figure 22D:
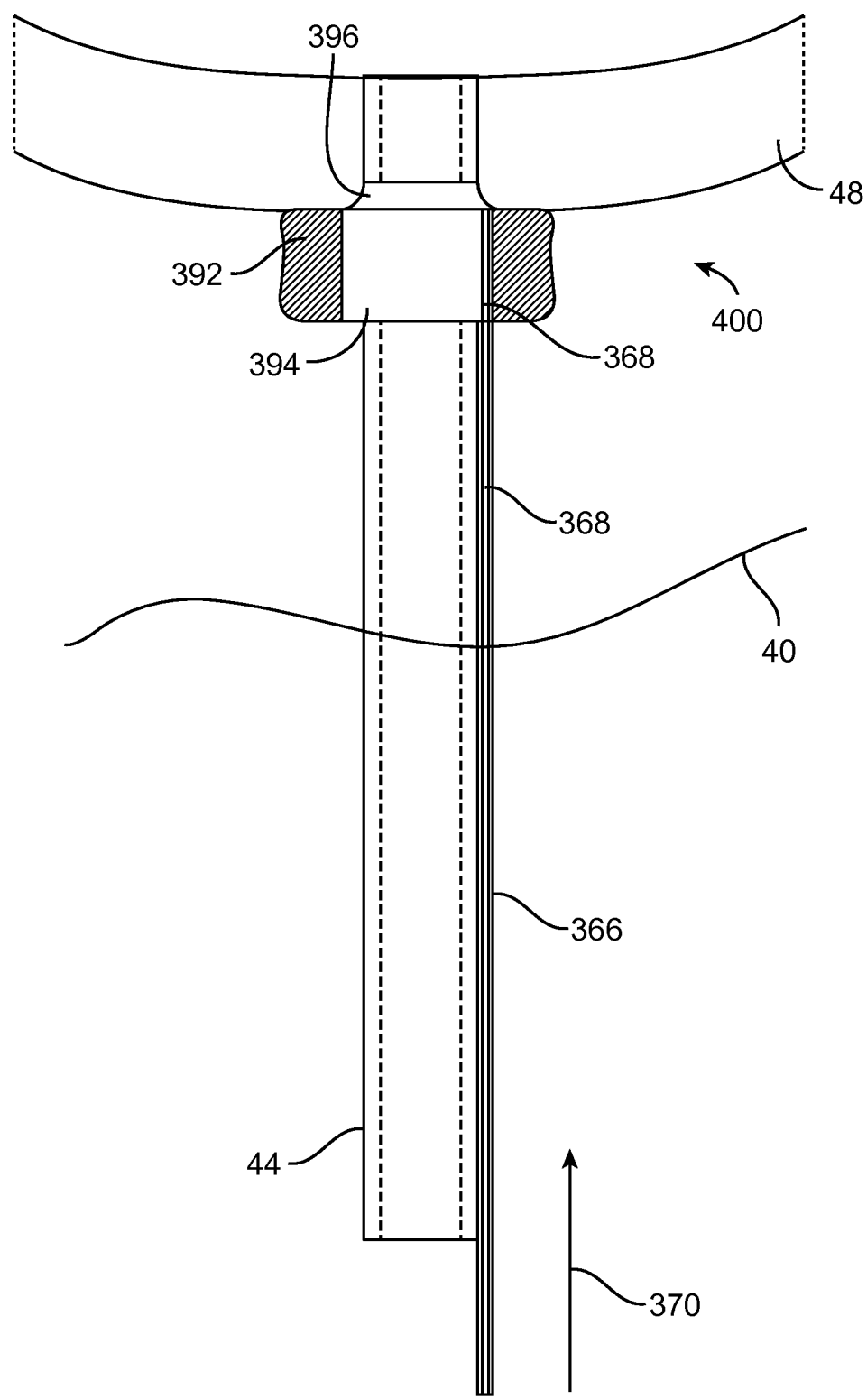
Figure 22E:
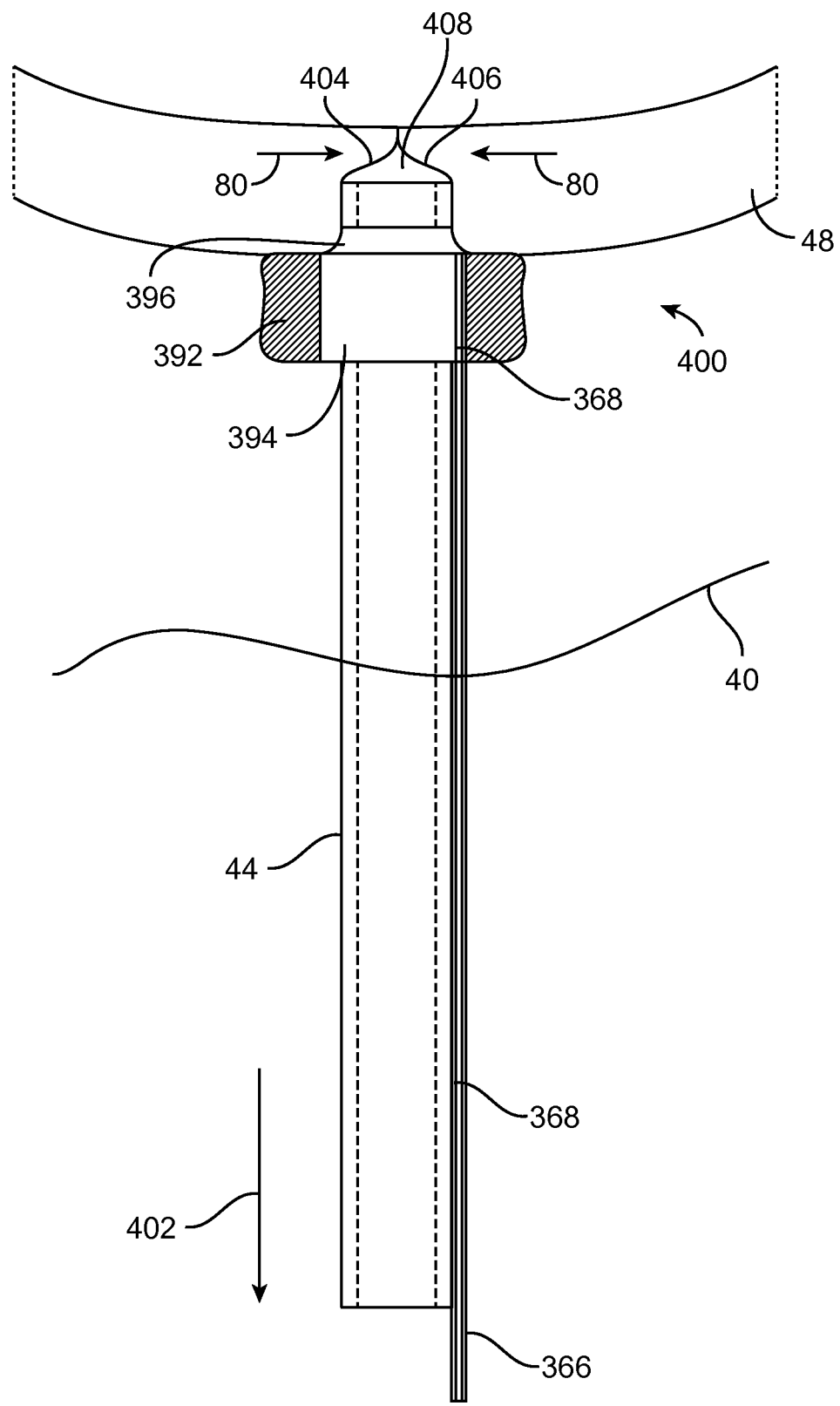
Figure 22F:
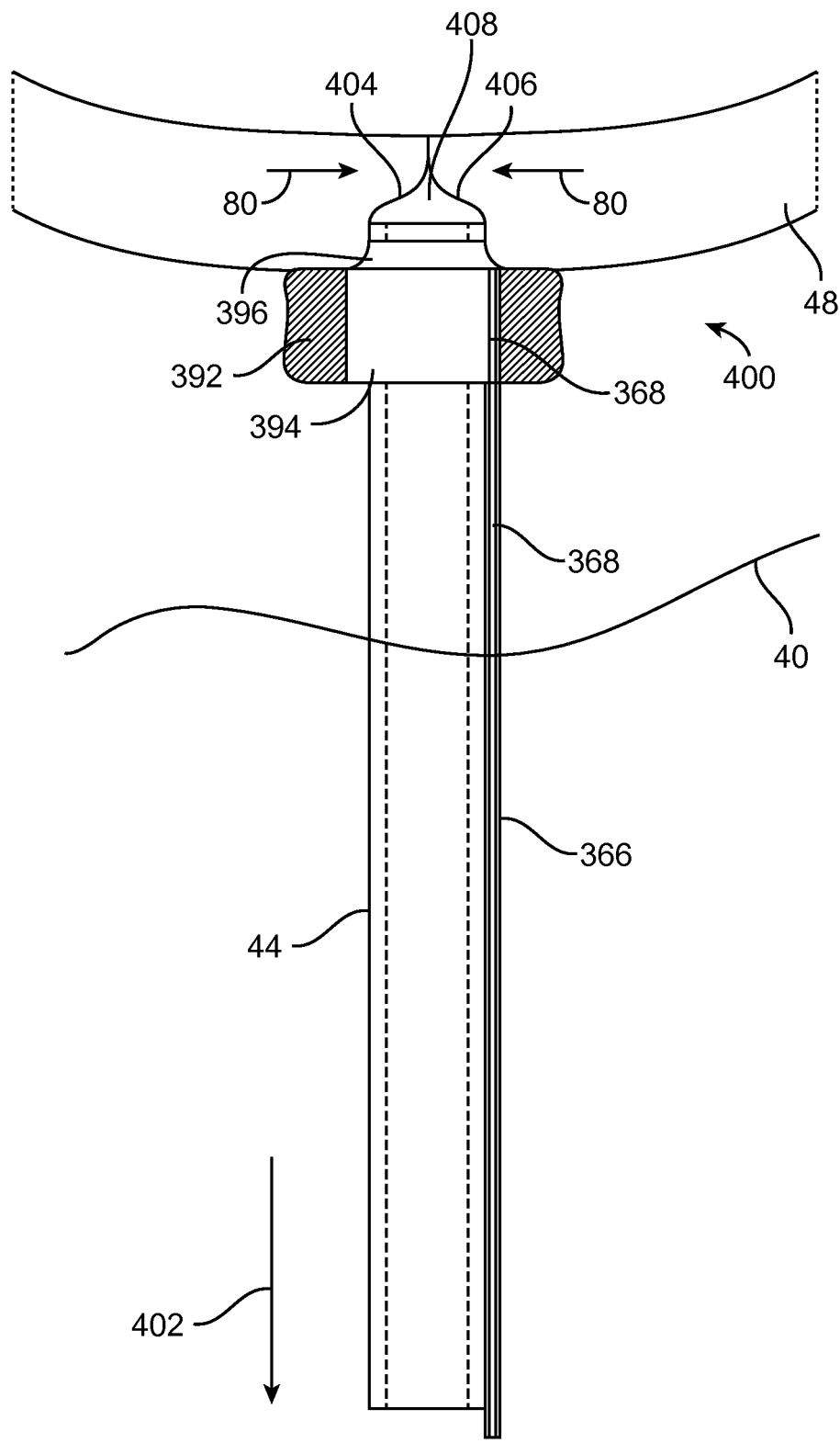
Figure 22G:
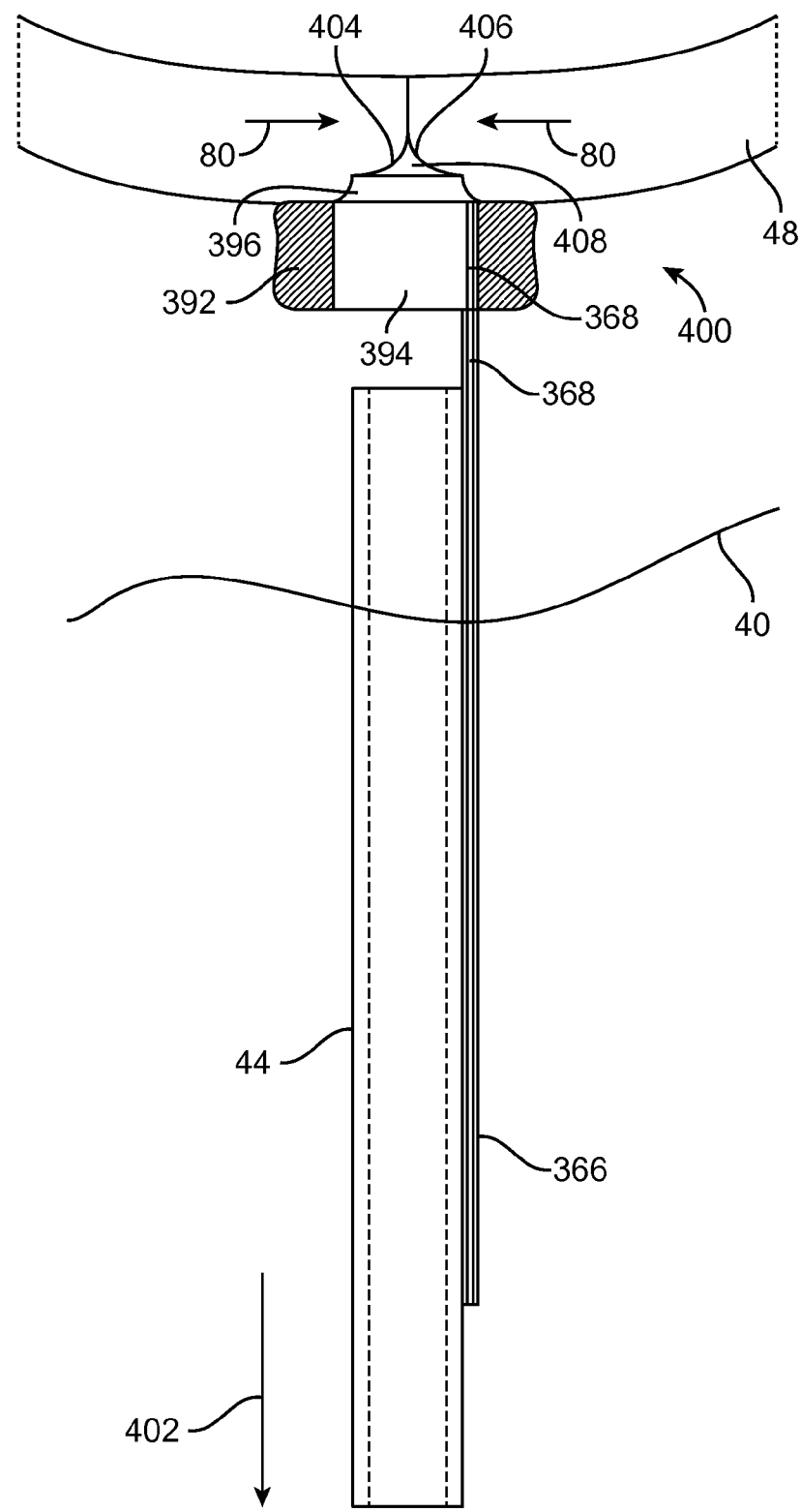
Figure 22H:
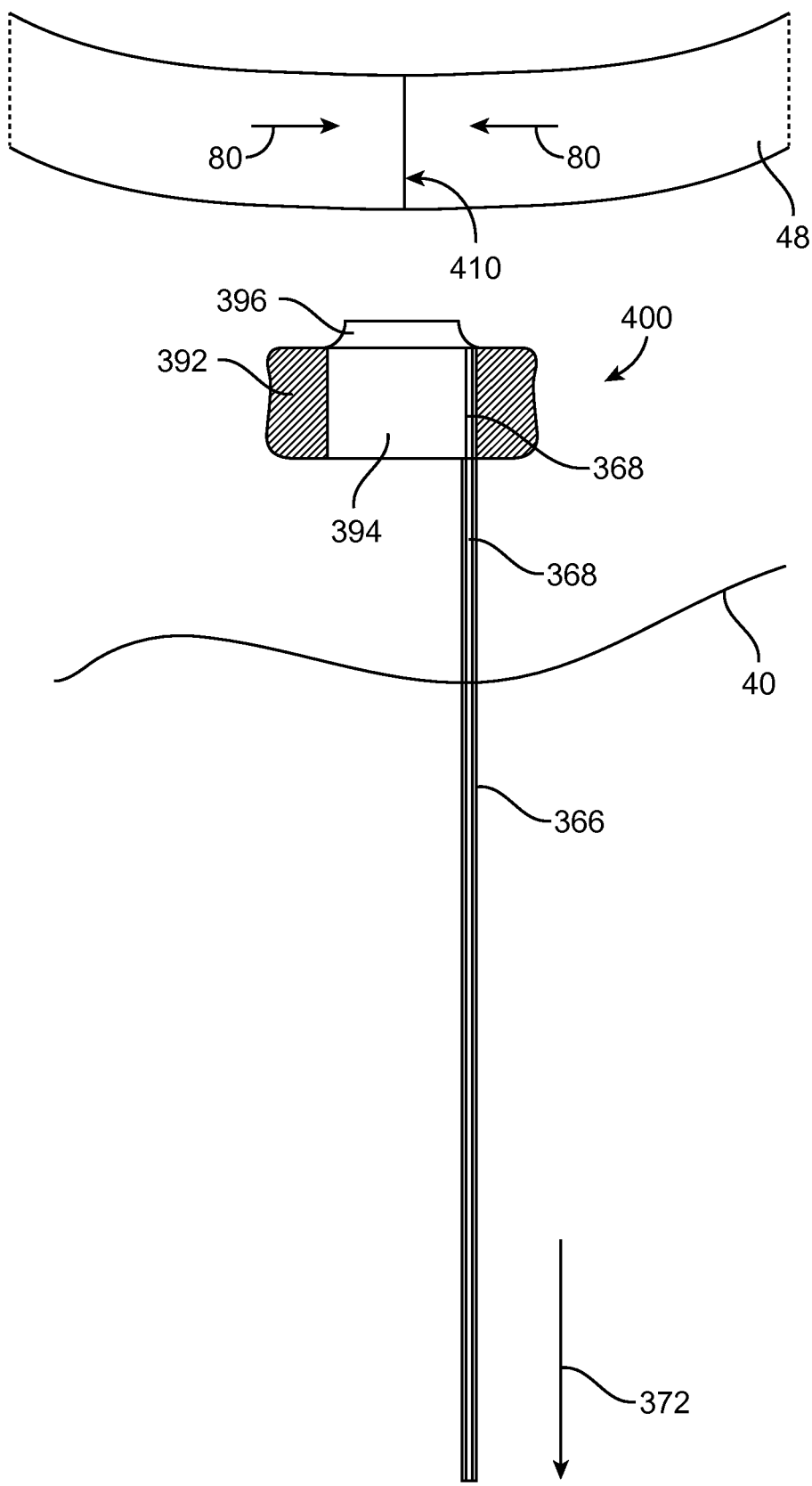
Figure 22I:
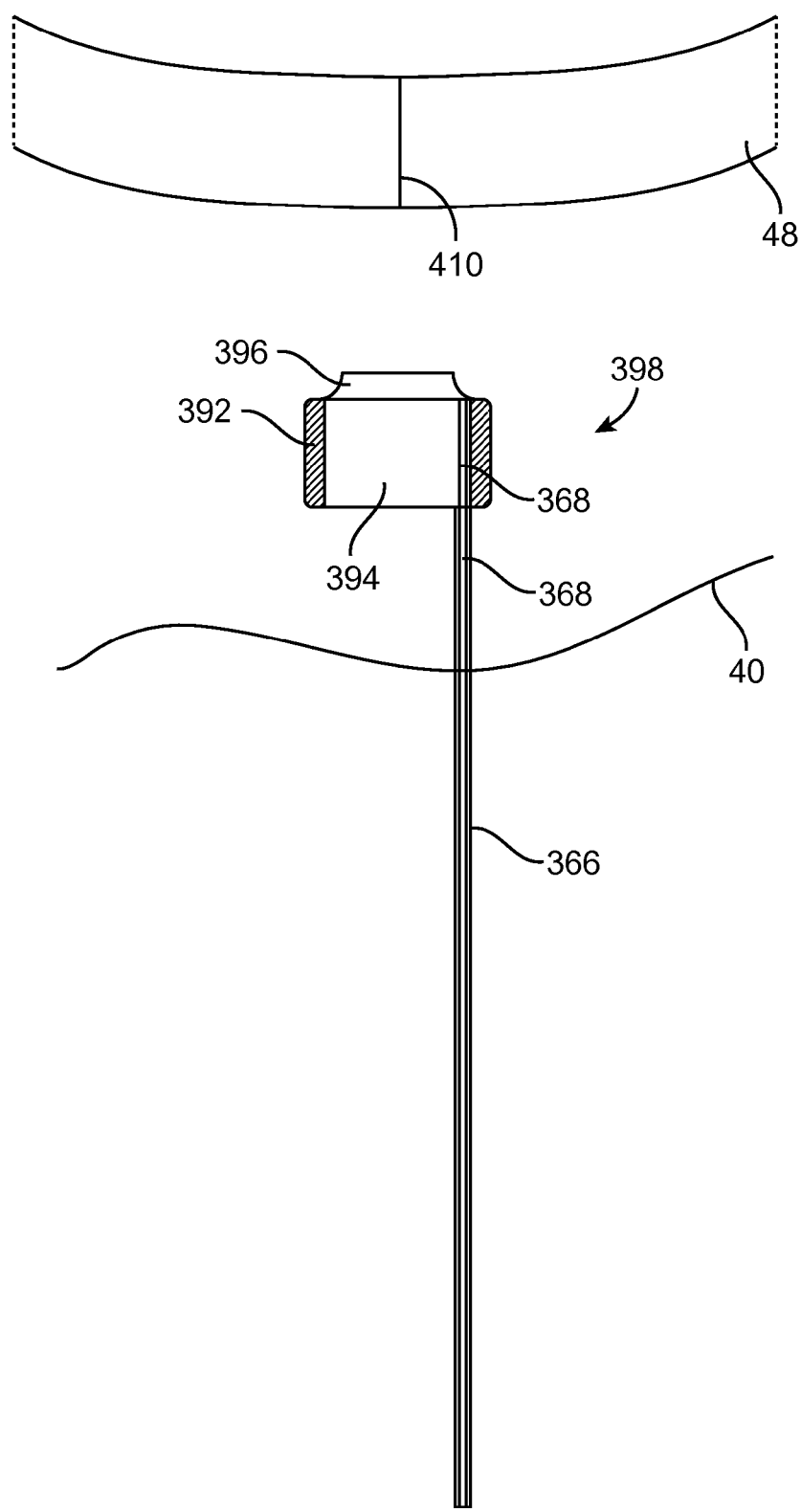
Figure 22J:
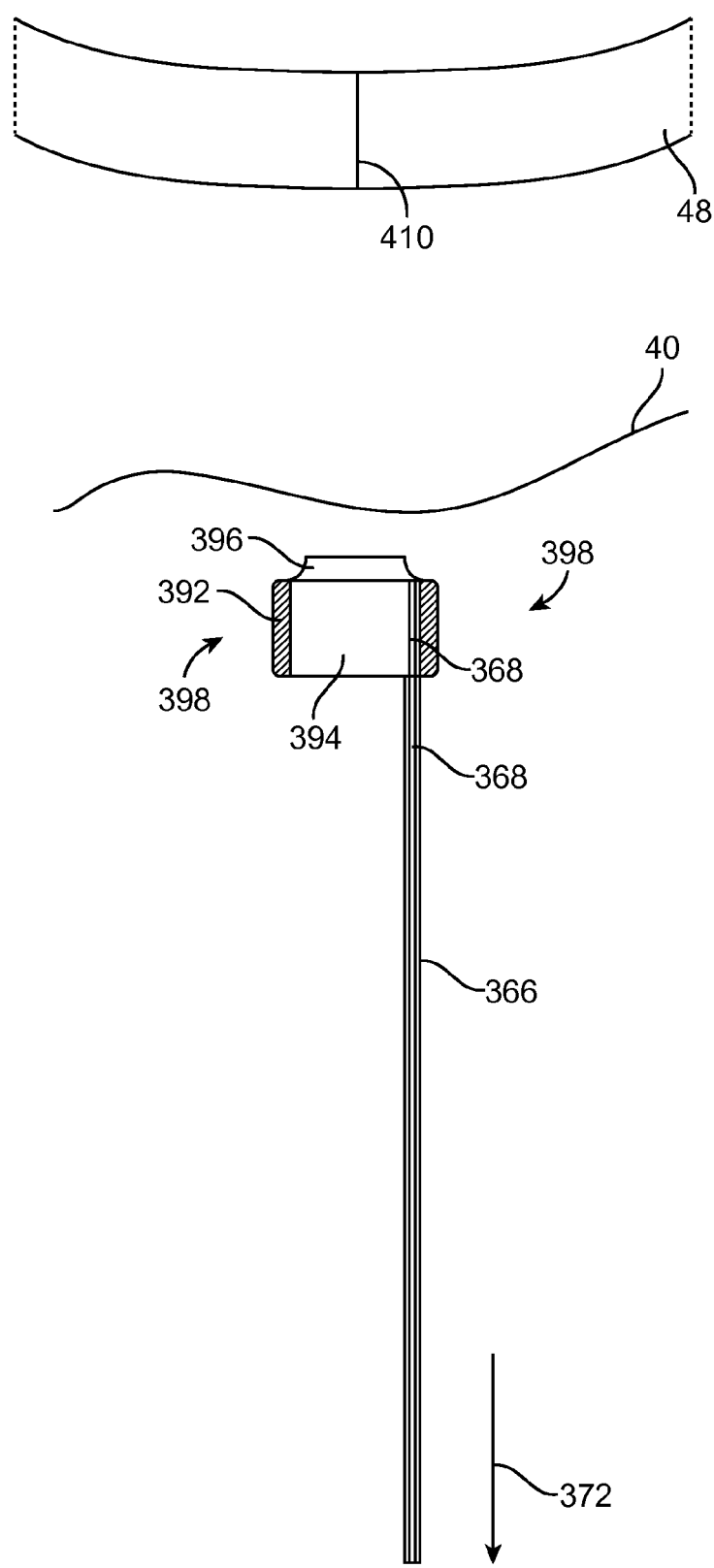
Figure 22K:
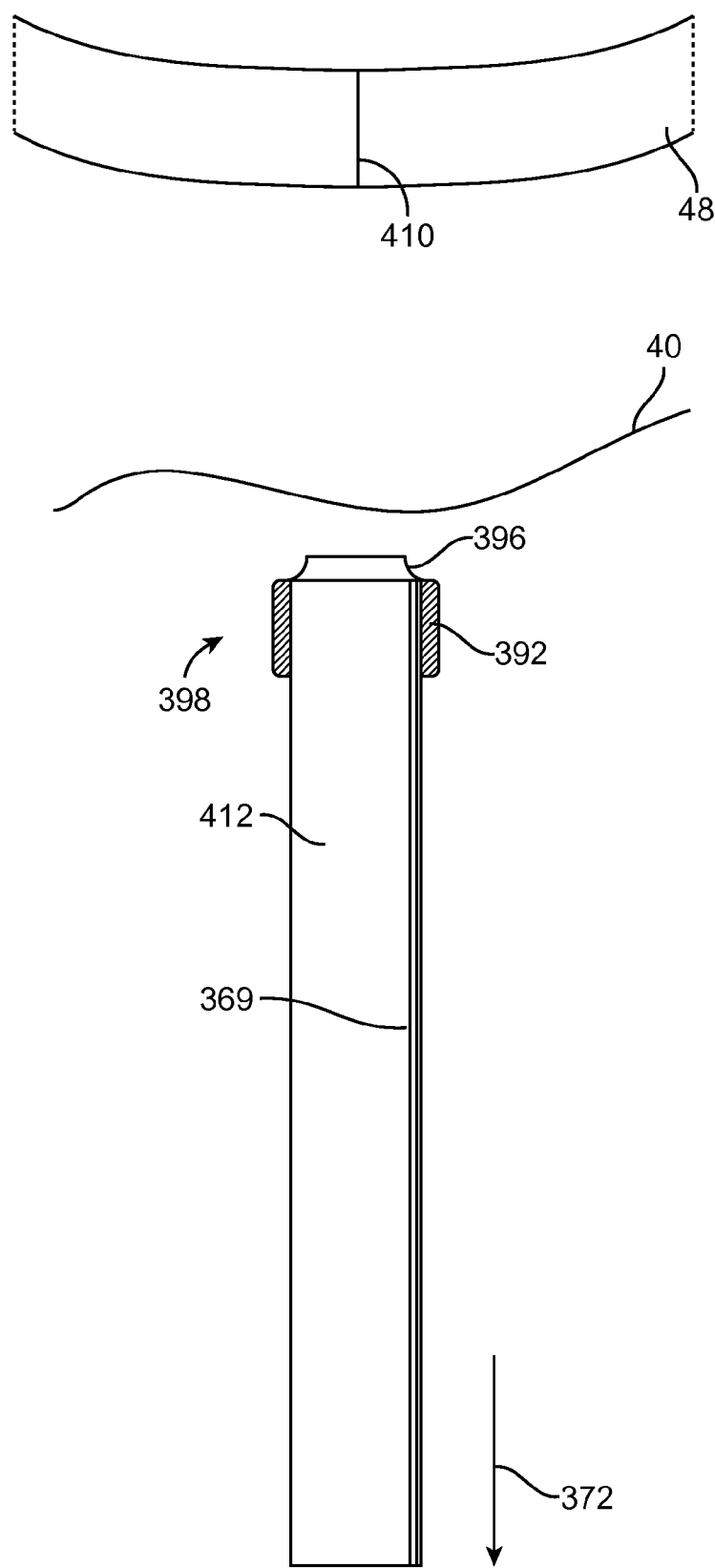

Referring to FIGS. 22A-22K, another embodiment is depicted wherein a tubular support member (394) is coupled to a tapered distal tip member (396) and circumferential (i.e., like a donut shape around the tubular support member; akin to an angioplasty balloon assembly) inflatable member (392), shown in its compressed state (398) in FIG. 22A. Referring to FIG. 22B, the tubular support member (394) and associated inflatable member (392) and distal tip member (396) may be advanced past the chest wall (40) with the inflatable member (392) in its collapsed configuration. Referring to FIG. 22C, the inflation lumen (368) may be utilized to controllably inflate the inflatable member (392) to its expanded state (400). Referring to FIG. 22D, the expanded assembly may be urged against the defect or wound at the intersection of the introducer (44) and left ventricular wall (48), with the tapered distal tip member (396) advanced slightly into the wound or defect to assist with the prevention of leakage of fluids such as blood past the introducer (44)/tissue wall (48) intersection. In one embodiment, the introducer may be left in place as in FIGS. 20G and 21J, and a closure configuration such as those described above (for example, in reference to FIGS. 3A-3Z-3, or FIGS. 9A-11B) utilized to ultimately close the defect or wound left by the introducer. In the embodiment depicted in FIGS. 22E-22K, the defect or wound may be closed utilizing the assistance of the leak prevention assembly described in reference to FIGS. 22A-22D. Referring to FIG. 22E, with the leak prevention assembly remaining in place as in the configuration of FIG. 22D, retraction (402) of the introducer (44) may be started, with the tissue margins (404, 406) collapsing around a void (408) left behind after the introducer is withdrawn, allowing the compressed viscoelastic tissue to re-expand (80) to its natural position. Referring to FIG. 22F, introducer withdrawal (402) is continued with the leak prevention assembly remaining in place as in the configuration of FIG. 22D. Similarly, in FIG. 22G, the introducer withdrawal (402) is continued, and the leak prevention assembly remains in place, while the tissue wall wound margins (404, 406) continue to collapse around the void (408) left by the exiting introducer (44). Referring to FIG. 22H, with adequate time and clot formation, the wound becomes closed (410) and the leak prevention assembly may be withdrawn. Referring to FIG. 22I, the inflatable member (394) may be returned to its collapsed state (398), and the assembly may be withdrawn (372) past the chest wall (40), as in FIG. 22J. Referring to FIG. 22K, in another embodiment, a similar procedure may be accomplished with a more substantial proximal construct: in place of the tubular support member (394) and structural manipulation member (366) of the embodiments of FIGS. 22A-22J, a single elongate tubular support member (412), also defining an inflation lumen (369) therethrough as well as a working lumen through which an introducer may be slidably disposed, may be utilized in a similar procedure.

Figure 23:
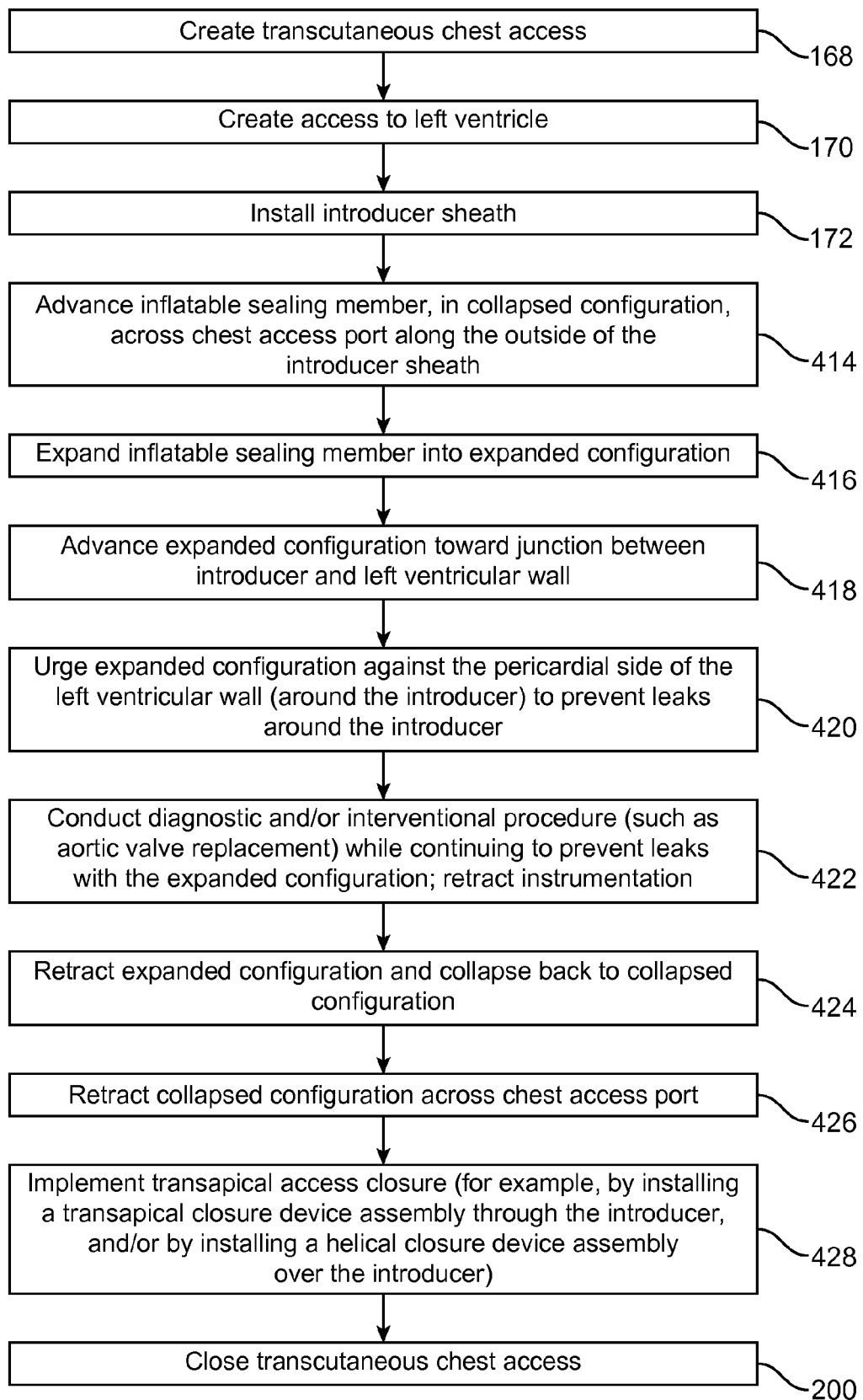
FIGS. 23-25 illustrate various aspects of deployment paradigms similar to those described in reference to FIGS. 20A-22K.
Figure 24:
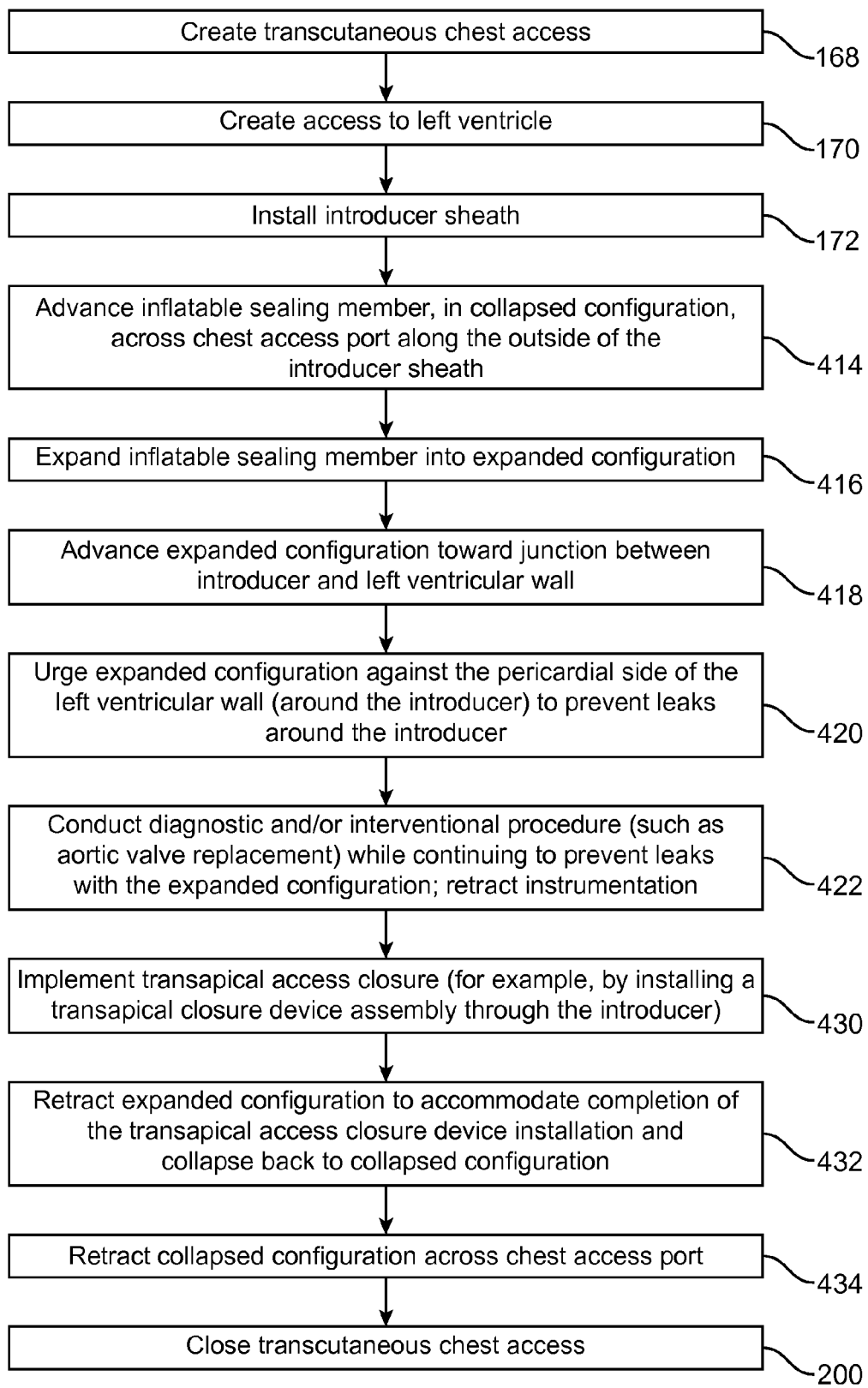
Figure 25:
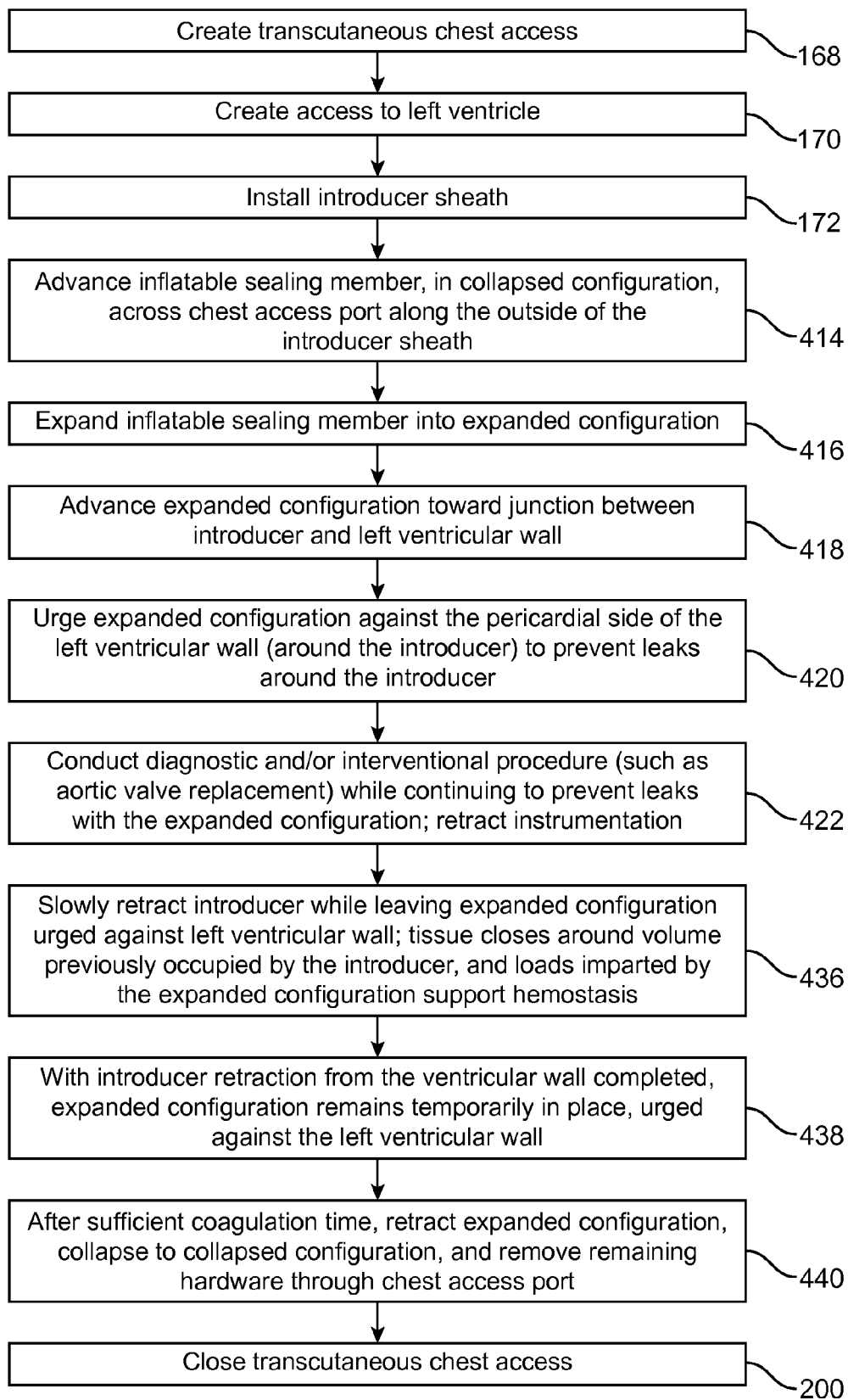

Referring to FIGS. 23-25, various procedural embodiments are depicted with similarities to those described in reference to FIGS. 20A-22K. Referring to FIG. 23, chest access may be created (168) along with access to the left ventricle (170). An introducer sheath may be installed (172). An inflatable sealing member may be advanced in an collapsed configuration across the chest access port along the outside of the introducer (414). An inflatable sealing member may be expanded to an expanded configuration (416). The expanded configuration may be advanced toward the junction between the introducer and the left ventricular wall (418). The expanded configuration may be urged against the pericardial side of the left ventricular wall (around the introducer) to prevent leaks around the introducer (420). A diagnostic and/or interventional procedure may be conducted, while leak prevention is continued with the associated assembly, and the diagnostic/interventional hardware may be withdrawn (422). The expanded leak prevention configuration may be partially withdrawn and collapsed back to the collapsed configuration (424). The collapsed configuration may be withdrawn across the chest wall (426), and a transapical access closure may be implemented (428) utilizing the introducer which remains in place (428). After the closure is completed, the chest access port may be closed (200).

Referring to FIG. 24, an embodiment similar to that depicted in FIG. 23 is shown, but after the step of conducting a diagnostic and/or interventional procedure and removing the associated instrumentation (422), before withdrawal of the leak prevention assembly, at least the first portion of a transapical access closure may be conducted from the inside of the heart first (430), followed by retraction of the expanded leak prevention assembly to accommodate completion of the closure device installation on the proximal (i.e., pericardial) side (432), retraction of a collapsed configuration of the leak prevention apparatus (434), and closure of the chest access (200).

Referring to FIG. 25, an embodiment similar to that depicted in FIG. 23 is shown, but after the step of conducting a diagnostic and/or interventional procedure and removing the associated instrumentation (422), the introducer is slowly retracted while leaving the expanded leak prevention assembly in place (436), until the introducer is fully retracted (438). After sufficient coagulation time, the leak prevention assembly is collapsed and retracted (440), and the chest access closed (200).

Any of the aforementioned deployed structures, including sutures, anchor members, and ratcheting closure device assembly components, may comprise resorbable materials in addition to the aforementioned nonresorbable materials—to facilitate combinations and permutations which may be completely resorbed, leaving behind a biologically healed transapical access wound.

Various exemplary embodiments of the invention are described below. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

Any of the devices described for carrying out the subject interventions may be provided in packaged combination for use in executing such interventions. These supply "kits" further may include instructions for use and be packaged in sterile trays or containers as commonly employed for such purposes.

The invention includes methods that may be performed using the subject devices. The methods may comprise the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally know or appreciated by those with skill in the art. For example, one with skill in the art will appreciate that one or more lubricious coatings (e.g., hydrophilic polymers such as polyvinylpyrrolidone-based compositions, fluoropolymers such as tetrafluoroethylene, hydrophilic gel or silicones) may be used in connection with various portions of the devices, such as relatively large interfacial surfaces of movably coupled parts, if desired, for example, to facilitate low friction manipulation or advancement of such objects relative to other portions of the instrumentation or nearby tissue structures. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The invention claimed is:

1. A system for providing surgical access across a wall of a tissue structure, comprising:
   a. a delivery member having proximal and distal ends;
   b. a plurality of helical members, each having proximal and distal ends and a helical shape, each proximal end coupled to the delivery member distal end, each distal end extending distally of the delivery member distal end;
   c. a plurality of anchor members removably coupled to the helical member distal ends; and
   d. a plurality of suture members coupled distally to a portion of one of the anchor members and extending proximally to a position wherein at least a portion of each may be freely manipulated by an operator;
   wherein upon rotation of the delivery member in a first direction, the helical members and coupled anchor members are advanced across at least a portion of the wall of the tissue structure, pulling along the distal portions of the suture members in a deployed suture pattern which remains coupled to the anchor member; and
   wherein upon rotation of the delivery member in a second direction opposite to the first direction, a reverse load is applied to the delivery member and coupled plurality of helical members which causes the plurality of anchor members to become decoupled from the helical members, such that further rotation in the second direction causes removal of the helical members and delivery member while the anchor members and suture member distal portions remain positioned across the portion of the wall of the tissue structure.

2. The system of claim 1, wherein the deployed suture pattern is characterized in that in the aggregate it represents a number of helical loops encapsulated by the wall of the tissue structure that is greater than about one and one-half helical loops, and is less than about four helical loops.

3. The system of claim 2, wherein the deployed suture pattern is characterized in that in the aggregate it represents a number of helical loops encapsulated by the wall of the tissue structure that is greater than about one and one-half helical loops, and is less than about two and one-half helical loops.

4. The system of claim 1, wherein the plurality of helical members comprises two, the plurality of anchor members comprises two, and the plurality of suture members comprises two.

5. The system of claim 1, wherein at least one anchor member has at least one shape feature that is configured to slide past nearby tissue structures during inward insertion loading associated with rotation of a first helical member in the first direction, and to resist movement relative to the nearby tissue structures upon application of outward extraction loading associated with rotation of the first helical member in the second direction.

6. The system of claim 1, wherein the helical members and coupled anchor members are advanced in a substantially helical pathway.

7. The system of claim 1, wherein a distal end of at least one of the plurality of helical members comprises a sharpened tip configured to easily dive into and cross portions.

8. The system of claim 7, wherein at least one helical member defines an inner helix diameter that is substantially constant across the length of the helical member.

9. The system of claim 7, wherein the inner helix diameters of the first and second helical members are substantially equal.

10. The system of claim 7, wherein the inner helix diameters of the first and second helical members are substantially unequal.

11. The system of claim 7, wherein the first and second helical members define longitudinal axes that are substantially coaxial.

12. The system of claim 1, wherein at least one of the plurality of helical members comprises a tubular construct.

13. The system of claim 1, wherein at least one of the plurality of helical members comprises stainless steel.

14. The system of claim 1, wherein at least one of the plurality of suture members is coupled to an eyelet coupled to an anchor member.

15. The system of claim 1, wherein the deployed suture pattern is configured to provide circumferential slack to facilitate relative movement of the elongate instrument therethrough.

* * * * *